(12) United States Patent
Townley et al.

(10) Patent No.: US 10,695,557 B1
(45) Date of Patent: Jun. 30, 2020

(54) SYSTEMS AND METHODS FOR THERAPEUTIC NASAL NEUROMODULATION

(71) Applicant: Neurent Medical Limited, Oranmore, Galway (IE)

(72) Inventors: David Townley, County Clare (IE); Brian Shields, County Galway (IE)

(73) Assignee: Neurent Medical Limited, Oranmore, Galway (IE)

( * ) Notice: Subject to any disclaimer, the term of this patent is extended or adjusted under 35 U.S.C. 154(b) by 0 days.

(21) Appl. No.: 16/701,902

(22) Filed: Dec. 3, 2019

Related U.S. Application Data

(60) Provisional application No. 62/896,845, filed on Sep. 6, 2019, provisional application No. 62/832,914, filed on Apr. 12, 2019, provisional application No. 62/832,917, filed on Apr. 12, 2019, provisional application No. 62/832,918, filed on Apr. 12, 2019, provisional application No. 62/832,920, filed on Apr. 12, 2019, provisional application No. 62/832,923, filed on Apr. 12, 2019, provisional application No. 62/832,925, filed on Apr. 12, 2019, provisional application No. 62/832,927, filed on Apr. 12, 2019, provisional application No. 62/832,928, filed on Apr. 12, 2019, provisional application No. 62/778,233, filed on Dec. 11, 2018.

(51) Int. Cl.
| | |
|---|---|
| *A61B 18/12* | (2006.01) |
| *A61N 1/05* | (2006.01) |
| *A61B 18/14* | (2006.01) |
| *A61B 18/00* | (2006.01) |

(52) U.S. Cl.
CPC ........ *A61N 1/0546* (2013.01); *A61B 18/1206* (2013.01); *A61B 18/14* (2013.01); *A61B 2018/00166* (2013.01); *A61B 2018/00214* (2013.01); *A61B 2018/00327* (2013.01); *A61B 2018/00577* (2013.01); *A61B 2018/1407* (2013.01); *A61B 2018/1475* (2013.01)

(58) Field of Classification Search
CPC .. A61N 1/0546; A61B 18/14; A61B 18/1206; A61B 2018/1407; A61B 2018/00577; A61B 2018/00214; A61B 2018/00166; A61B 2018/1475
See application file for complete search history.

(56) References Cited

U.S. PATENT DOCUMENTS

| | | | | |
|---|---|---|---|---|
| 6,352,533 | B1 * | 3/2002 | Ellman | A61B 18/1482 606/41 |
| 2003/0212394 | A1 * | 11/2003 | Pearson | A61B 18/1477 606/41 |
| 2005/0080409 | A1 * | 4/2005 | Young | A61B 18/1482 606/41 |
| 2005/0171536 | A1 * | 8/2005 | Phan | A61B 18/1492 606/49 |
| 2015/0164571 | A1 * | 6/2015 | Saadat | A61N 7/022 600/109 |
| 2016/0331459 | A1 * | 11/2016 | Townley | A61N 7/00 |
| 2017/0151014 | A1 * | 6/2017 | Perfler | A61B 18/1492 |

* cited by examiner

*Primary Examiner* — Daniel W Fowler
(74) *Attorney, Agent, or Firm* — Brown Rudnick LLP; Adam M. Schoen

(57) ABSTRACT

The invention generally relates to systems and methods for therapeutically modulating nerves in or associated with a nasal region of a patient for the treatment of a rhinosinusitis condition.

10 Claims, 18 Drawing Sheets

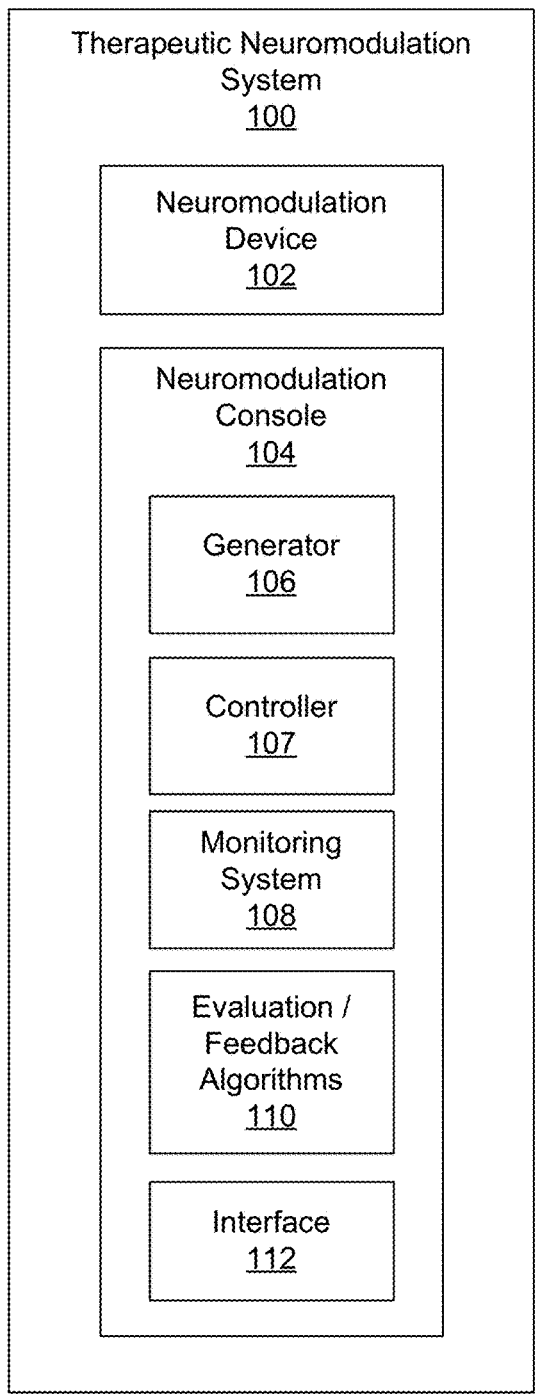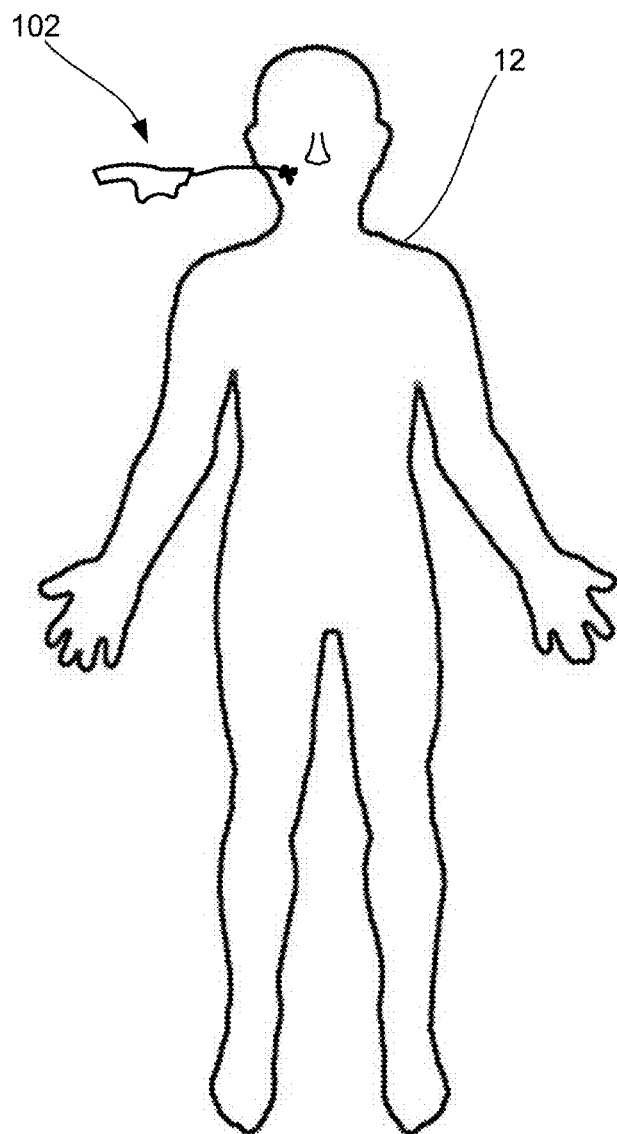
FIG. 1A
FIG. 1B

*400*

┌─────────────────────────────────────────────────────┐
│ Advance a multi-segment end effector within the nasal cavity │ ─── 410
│ of the patient, the multi-segment end effector including a first │
│ segment spaced apart from a second segment │
└─────────────────────────────────────────────────────┘
                            │
                            ▼
┌─────────────────────────────────────────────────────┐
│ Deploy the first and second segments at respective first and │ ─── 420
│ second locations within the nasal cavity │
└─────────────────────────────────────────────────────┘
                            │
                            ▼
┌─────────────────────────────────────────────────────┐
│ Deliver energy, via the first and second segments, to tissue at │ ─── 430
│ one or more target sites with respect to the first and second │
│ locations │
└─────────────────────────────────────────────────────┘

```
┌─────────────────────────────────────────────────────────────┐
│ Provide a treatment device comprising a multi-segment end   │──610
│ effector, including a proximal segment that is spaced apart │
│ from a distal segment, and a visual marker                  │
└─────────────────────────────────────────────────────────────┘
                              ↓
┌─────────────────────────────────────────────────────────────┐
│ Advance, under image guidance, the proximal segment and the │──620
│ distal segment through a nasal cavity of a patient and past │
│ a middle turbinate                                          │
└─────────────────────────────────────────────────────────────┘
                              ↓
┌─────────────────────────────────────────────────────────────┐
│ Deploy the distal segment from a retracted configuration to │──630
│ an expanded configuration                                   │
└─────────────────────────────────────────────────────────────┘
                              ↓
┌─────────────────────────────────────────────────────────────┐
│ Align, under the image guidance and with reference to the   │──640
│ visual marker, the proximal segment with respect to the     │
│ middle turbinate                                            │
└─────────────────────────────────────────────────────────────┘
                              ↓
┌─────────────────────────────────────────────────────────────┐
│ Deploy the proximal segment around the middle turbinate and │──650
│ advance the deployed proximal segment toward the middle     │
│ turbinate to establish contact and secure the proximal      │
│ segment to the middle turbinate                             │
└─────────────────────────────────────────────────────────────┘
                              ↓
┌─────────────────────────────────────────────────────────────┐
│ Deliver energy, via the proximal segment, to the middle     │──660
│ turbinate to treat a condition.                             │
└─────────────────────────────────────────────────────────────┘
```

FIG. 15

SYSTEMS AND METHODS FOR THERAPEUTIC NASAL NEUROMODULATION

CROSS-REFERENCE TO RELATED APPLICATIONS

This application claims priority to, and the benefit of, U.S. Provisional Application No. 62/778,233, filed Dec. 11, 2018, U.S. Provisional Application No. 62/832,914, filed Apr. 12, 2019, U.S. Provisional Application No. 62/832,917, filed Apr. 12, 2019, U.S. Provisional Application No. 62/832,918, filed Apr. 12, 2019, U.S. Provisional Application No. 62/832,920, filed Apr. 12, 2019, U.S. Provisional Application No. 62/832,923, filed Apr. 12, 2019, U.S. Provisional Application No. 62/832,925, filed Apr. 12, 2019, U.S. Provisional Application No. 62/832,927, filed Apr. 12, 2019, U.S. Provisional Application No. 62/832,928, filed Apr. 12, 2019, U.S. Provisional Application No. 62/896,845, Sep. 6, 2019, the contents of each of which are incorporated by reference herein in their entireties.

FIELD OF THE INVENTION

The invention generally relates to systems and methods for treating medical conditions, and, more particularly, to therapeutically modulating nerves in a nasal region of a patient for the treatment of a rhinosinusitis condition.

BACKGROUND

Rhinitis is an inflammatory disease of the nose and is reported to affect up to 40% of the population. It is the fifth most common chronic disease in the United States. The most common and impactful symptoms of rhinitis are congestion and rhinorrhea. Allergic rhinitis accounts for up to 65% of all rhinitis patients. Allergic rhinitis is an immune response to an exposure to allergens, such as airborne plant pollens, pet dander or dust. Non-allergic rhinitis is the occurrence of common rhinitis symptoms of congestion and rhinorrhea. As non-allergic rhinitis is not an immune response, its symptoms are not normally seasonal and are often more persistent. The symptoms of rhinitis include a runny nose, sneezing, and nasal itching and congestion.

Allergen avoidance and pharmacotherapy are relatively effective in the majority of mild cases, but these medications need to be taken on a long-term basis, incurring costs and side effects and often have suboptimal efficacy. For example, pharmaceutical agents prescribed for rhinosinusitis have limited efficacy and undesirable side effects, such as sedation, irritation, impairment to taste, sore throat, dry nose, and other side effects.

There are two modern surgical options: the delivery of thermal energy to the inflamed soft tissue, resulting in scarring and temporary volumetric reduction of the tissue to improve nasal airflow; and microdebrider resection of the inflamed soft tissue, resulting in the removal of tissue to improve nasal airflow. Both options address congestion as opposed to rhinorrhea and have risks ranging from bleeding and scarring to the use of general anesthetic.

SUMMARY

The invention recognizes that a problem with current surgical procedures is that such procedures are not accurate and cause significant collateral damage in order to treat rhinitis. The invention solves that problem by providing devices having a unique multi-stage end effector and a handle architecture that provides a high level of precise control and feedback to an operator during use of the devices of the invention. The multi-stage end effector is configured to complement anatomy at multiple different locations within the nasal cavity. The handle is configured with multiple ergonomic and functional features that improve device use and feedback, such as independent control of deployment of the end effector and energy delivery and a shape associated with the architecture of the end effector in the deployed configuration. The handle may also include one or more markings that provide a user with a spatial orientation of the end effector while the end effector is in a nasal cavity. In that manner, the present invention provides devices that are capable of highly conforming to anatomical variations within a nasal cavity while providing unprecedented control and guidance to an operator so that an operator can perform an accurate, minimally invasive, and localized application of energy to one or more target sites within the nasal cavity to cause multi-point interruption of neural signal without causing collateral damage or disruption to other neural structures.

Unlike other surgical treatments for rhinitis, the devices of the invention are minimally invasive. Accordingly, a procedure can be performed in an office environment under local anesthetic. The multi-stage end-effector allows for targeting the autonomic supply to the nasal turbinates and will have a positive impact on both allergic and non-allergic rhinitis. Using this approach, it is expected that devices of the invention will be able to provide long-term symptom relief (e.g., years instead of months). Since the treatment is accurate with minimal collateral damage to the surrounding tissue, patients will begin to feel symptom relief immediately following the treatment. It is fully expected that patients will be removed from their pharmacotherapies following this therapy.

The systems and methods of the present invention include a handheld device comprising a retractable and expandable multi-segment end effector that, once delivered to the one or more target sites within the nasal cavity, can expand to a specific shape and/or size corresponding to anatomical structures within the nasal cavity and associated with the target sites. In particular, the end effector includes at least a first flexible segment and a second flexible segment, each of which includes a specific geometry when in a deployed configuration to complement anatomy of respective locations within the nasal cavity. Once deployed, the first and second segments contact and conform to a shape of the respective locations, including conforming to and complementing shapes of one or more anatomical structures at the respective locations. In turn, the first and second segments become accurately positioned within the nasal cavity to subsequently deliver, via one or more electrodes, precise and focused application of RF thermal energy to the one or more target sites to thereby therapeutically modulate associated neural structures. More specifically, the first and second segments have shapes and sizes when in the expanded configuration that are specifically designed to place portions of the first and second segments, and thus one or more electrodes associated therewith, into contact with target sites within nasal cavity associated with postganglionic parasympathetic fibers that innervate the nasal mucosa.

The handheld device further includes a shaft operably associated with the end effector and a handle operably associated with the shaft. The shaft may include a predefined shape (i.e., bent or angled at a specific orientation) so as to assist the surgeon (or other medical professional) for placement of the end effector at the target sites. The handle includes an ergonomically-designed grip portion which provides ambidextrous use for both left and right handed use and conforms to hand anthropometrics to allow for at least one of an overhand grip style and an underhand grip style during use in a procedure. The handle further includes multiple user-operated mechanisms, including at least a first mechanism for deployment of the end effector from the retracted configuration to the expanded deployed configuration and a second mechanism for controlling of energy output by the end effector. The user inputs for the first and second mechanisms are positioned a sufficient distance to one another to allow for simultaneous one-handed operation of both user inputs during a procedure. Accordingly, the handle accommodates various styles of grip and provides a degree of comfort for the surgeon, thereby further improving execution of the procedure and overall outcome. Furthermore, the handle and/or the shaft may include markings (e.g., text, symbols, color-coding insignia, etc.) that provide a surgeon with a spatial orientation of the end effector while the end effector is in a nasal cavity. In particular, multiple markings may be provided on the handle and/or shaft and provide a visual indication of the spatial orientation of one or more portions of the first segment and second segment of the end effector when in the deployed configurations. Thus, during initial placement of the end effector, when in a retracted configuration and enclosed within the shaft, a surgeon can rely on the markings on the handle and/or shaft as a visual indication of the spatial orientation of the end effector (e.g., linear, axial, and/or depth position) prior to deployment to thereby ensure that, once deployed, the end effector, including both the first and second segments, are positioned in the intended locations within the nasal cavity.

Accordingly, the handheld device of the present invention provides a user-friendly, non-invasive means of treating rhinosinusitis conditions, including precise and focused application of RF thermal energy to the intended target sites for therapeutic modulation of the intended neural structures without causing collateral and unintended damage or disruption to other neural structures. Thus, the efficacy of a vidian neurectomy procedure can be achieved with the systems and methods of the present invention without the drawbacks discussed above. Most notably, the handheld device provides a surgeon with a user-friendly, non-invasive, and precise means for treating rhinorrhea and other symptoms of rhinosinusitis by targeting only those specific neural structures associated with such conditions, notably postganglionic parasympathetic nerves innervating nasal mucosa, thereby disrupting the parasympathetic nerve supply and interrupting parasympathetic tone. Accordingly, such treatment is effective at treating rhinosinusitis conditions while greatly reducing the risk of causing lateral damage or disruption to other nerve fibers, thereby reducing the likelihood of unintended complications and side effects.

One aspect of the invention provides a device for treating a condition within a nasal cavity of a patient. The device includes a multi-segment end effector for delivering energy to one or more target sites within the nasal cavity of the patient. The multi-segment end effector includes a proximal segment that is spaced apart from a distal segment.

In some embodiments, the proximal segment comprises a first set of flexible support elements arranged in a first configuration and a first set of electrodes provided by the first set of support elements and configured to deliver energy to tissue at a first target site. The distal segment comprises a second set of flexible support elements arranged in a second configuration and a second set of electrodes provided by the second set of support elements and configured to deliver energy to tissue at a second target site. Each of the proximal and distal segments is transformable between a retracted configuration and an expanded deployed configuration such that the first and second sets of flexible support elements are configured to position one or more of the respective first and second sets of electrodes at the first and second target sites when in the deployed configuration. When in the expanded deployed configuration, the first set of support elements comprises a first pair of struts, each comprising a loop shape and extending upward and a second pair of struts, each comprising a loop shape and extending downward. The second set of support elements, when in the expanded deployed configuration, comprises a second set of struts, each comprising a loop shape extending outward to form an open-ended circumferential shape. The first and second sets of support elements comprise deformable composite wires. The composite wires may include a shape memory material, such as nitinol, for example.

In some embodiments, the first and second sets of electrodes are configured to deliver radiofrequency (RF) energy to tissue at respective target sites within the nasal cavity, wherein the respective target sites are associated with parasympathetic nerve supply. For example, the first and second sets of electrodes may be configured to deliver RF energy at a level sufficient to therapeutically modulate postganglionic parasympathetic nerves innervating nasal mucosa at an innervation pathway within the nasal cavity of the patient. The innervation pathway may include a microforamina of a palatine bone of the patient. The condition to be treated by the device may include, but is not limited to, allergic rhinitis, non-allergic rhinitis, chronic rhinitis, acute rhinitis, chronic sinusitis, acute sinusitis, chronic rhinosinusitis, acute rhinosinusitis, and medical resistant rhinitis.

In some embodiments, the first segment of the multi-segment end effector has a first geometry to complement anatomy at a first location within the nasal cavity and the second segment of the multi-segment end effector has a second geometry to complement anatomy at a second location within the nasal cavity. Each of the first and second segments is transformable between a retracted configuration and an expanded deployed configuration such that the first set of flexible support elements of the first segment conforms to and complements a shape of a first anatomical structure at the first location when the first segment is in the deployed configuration and the second set of flexible support elements of the second segment conforms to and complements a shape of a second anatomical structure at the second location when the second segment is in the deployed configuration. The first and second anatomical structures may include, but are not limited to, inferior turbinate, middle turbinate, superior turbinate, inferior meatus, middle meatus, superior meatus, pterygopalatine region, pterygopalatine fossa, sphenopalatine foramen, accessory sphenopalatine foramen(ae), and sphenopalatine micro-foramen(ae).

In some embodiments, the first segment of the multi-segment end effector is configured in a deployed configuration to fit around at least a portion of a middle turbinate at an anterior position relative to the middle turbinate and the second segment of the multi-segment end effector is configured in a deployed configuration to contact a plurality of tissue locations in a cavity at a posterior position relative to the middle turbinate. For example, the first set of flexible support elements of the first segment conforms to and complements a shape of a lateral attachment and posterior-inferior edge of the middle turbinate when the first segment is in the deployed configuration and the second set of flexible support elements of the second segment contact a plurality of tissue locations in a cavity at a posterior position relative to the lateral attachment and posterior-inferior edge of middle turbinate when the second segment is in the deployed configuration. Accordingly, when in the deployed configuration, the first and second segments are configured to position one or more of respective first and second sets of electrodes at one or more target sites relative to the middle turbinate and the plurality of tissue locations in the cavity behind the middle turbinate. In turn, the first and second sets of electrodes are configured to deliver RF energy at a level sufficient to therapeutically modulate postganglionic parasympathetic nerves innervating nasal mucosa at an innervation pathway within the nasal cavity of the patient.

Another aspect of the invention provides a device for treating a condition within a nasal cavity of a patient. The device comprises an end effector transformable between a retracted configuration and an expanded deployed configuration, a shaft operably associated with the end effector, and a handle operably associated with the shaft. The handle includes a first mechanism for deployment of the end effector from the retracted configuration to the expanded deployed configuration and a second mechanism, separate from the first mechanism, for control of energy output by the end effector.

In some embodiments, the handle comprises an ergonomically-designed grip portion comprising a shape, size, and contour providing for ambidextrous use for both left and right handed use and conforming to hand anthropometrics to allow for at least one of an overhand grip style and an underhand grip style during use in a procedure. The user input for the first mechanism may be positioned on a top portion of the handle adjacent the grip portion and user input for the second mechanism is positioned on side portions of the handle adjacent the grip portion. The user inputs for the first and second mechanisms may be positioned a sufficient distance to one another to allow for simultaneous one-handed operation of both user inputs during a procedure.

In some embodiments, the first mechanism comprises a rack and pinion assembly providing movement of the end effector between the retracted and deployed configurations in response to input from a user-operated controller. The rack and pinion assembly may include a set of gears for receiving input from the user-operated controller and converting the input to linear motion of a rack member operably associated with at least one of the shaft and the end effector. The rack and pinion assembly may include a gearing ratio sufficient to balance a stroke length and retraction and deployment forces, thereby improving control over the deployment of the end effector.

In some embodiments, the user-operated controller comprises a slider mechanism operably associated with the rack and pinion rail assembly, wherein movement of the slider mechanism in a rearward direction towards a proximal end of the handle results in transitioning of the end effector to the deployed configuration and movement of the slider mechanism in a forward direction towards a distal end of the handle results in transitioning of the end effector to the retracted configuration.

In some embodiments, the user-operated controller comprises a scroll wheel mechanism operably associated with the rack and pinion rail assembly, wherein rotation of the wheel in a rearward direction towards a proximal end of the handle results in transitioning of the end effector to the deployed configuration and rotation of the wheel in a forward direction towards a distal end of the handle results in transitioning of the end effector to the retracted configuration.

In some embodiments, the second mechanism comprises a user-operated controller configured to be actuated between an active position and an inactive position to thereby control delivery of energy from the end effector. The user-operated controller may be multi-modal in that the user-operated controller may be actuated between multiple positions providing different functions/modes. For example, upon a single user input (i.e., single press of button associated within controller), the second mechanism may provide a baseline apposition/sensing check function prior to modulation. Upon pressing and holding the controller button for a pre-defined period of time, the energy output from the end effector may be activated. Further, upon double-tapping the controller button, energy output is deactivated.

In some embodiments, the handle may include a shape associated with the architecture of the end effector in the deployed configuration. For example, the handle may generally include a grip portion having a shape that provides a user with a physical confirmation of an orientation of portions of the end effector when in the deployed configuration. For example, the end effector may include a first segment that is spaced apart from a second segment, wherein each of the first and second segments is transformable between a retracted configuration and an expanded deployed configuration. The handle comprises a grip portion comprises a top, a bottom, sides, a proximal end, and a distal end, wherein at least one of the top, bottom, and sides of the grip portion of the handle is associated with architecture of at least one of the first and second segments of the end effector when in the deployed configuration. For example, the first segment may include a first set of flexible support elements and the second segment may include a second set of flexible support elements. When in the deployed configuration, the first set of support elements may include a first pair of struts, each comprising a loop shape and extending upward and second pair of struts, each comprising a loop shape and extending downward. The top of the grip portion, for example, may be associated with the upwardly extending first pair of struts and the bottom of the grip portion may be associated with the downwardly extending second pair of struts. When in the deployed configuration, the second set of support elements may include a second set of struts, each comprising a loop shape extending outward to form an open-ended circumferential shape. The distal end of the grip portion may be associated with the outwardly extending second set of struts.

In some embodiments, the handle and/or the shaft may include one or more markings that provide a user with a spatial orientation of the end effector while the end effector is in a nasal cavity. For example, one or more markings on the handle or shaft may provide a visual indication of the orientation of one or more portions of the end effector, specifically an indication of the spatial orientation of one or both of the first and second segments in the deployed configurations. The markings may include any visual mark, such as text, symbols, and color-coding insignia. In some embodiments, multiple markings may be provided to provide visual indication of one or more portions of the first and second segments when in deployed configurations. For example, a first marking on either or both of the handle and shaft may be associated with the upwardly extending first pair of struts of the first segment of the end effector and a second marking may be associated with the downwardly extending second pair of struts of the first segment of the end effector. As such, the first marking provides a user with a visual indication of the spatial orientation of the upwardly extending first pair of struts and the second marking provides a user with a visual indication of the spatial orientation of the downwardly extending second pair of struts while the first segment is in a nasal cavity in the deployed configuration.

Another aspect of the invention provides a method for treating a condition within a nasal cavity of a patient. The method includes advancing a device comprising a multi-segment end effector for delivering energy to one or more target sites within the nasal cavity of the patient. The multi-segment end effector comprises a proximal segment that is spaced apart from a distal segment. The method further includes delivering energy, via the proximal and distal segments, to tissue at the one or more target sites.

In some embodiments, the proximal segment comprises a first set of flexible support elements arranged in a first configuration and a first set of electrodes provided by the first set of support elements and configured to deliver energy to tissue at a first target site. The distal segment comprises a second set of flexible support elements arranged in a second configuration and a second set of electrodes provided by the second set of support elements and configured to deliver energy to tissue at a second target site. Each of the proximal and distal segments is transformable between a retracted configuration and an expanded deployed configuration such that the first and second sets of flexible support elements are configured to position one or more of the respective first and second sets of electrodes at the first and second target sites when in the deployed configuration. When in the expanded deployed configuration, the first set of support elements comprises a first pair of struts, each comprising a loop shape and extending upward and a second pair of struts, each comprising a loop shape and extending downward. The second set of support elements, when in the expanded deployed configuration, comprises a second set of struts, each comprising a loop shape extending outward to form an open-ended circumferential shape. The first and second sets of support elements comprise deformable composite wires and may include a shape memory material, such as nitinol.

In some embodiments the method further includes deploying the proximal and distal segments of the multi-segment end effector at respective first and second target sites to thereby position one or more of the respective first and second sets of electrodes at the first and second target sites. The delivering of energy via the proximal and distal segments comprises delivering radiofrequency (RF) energy, via one or more of the respective first and second sets of electrodes, at a level sufficient to therapeutically modulate postganglionic parasympathetic nerves innervating nasal mucosa at an innervation pathway within the nasal cavity of the patient.

In some embodiments, the first segment of the end effector has a first geometry to complement anatomy at a first location within the nasal cavity and the second segment has a second geometry to complement anatomy at a second location within the nasal cavity. Accordingly, the method may include deploying the first and second segments at the respective first and second locations within the nasal cavity and delivering energy, via the first and second segments, to tissue at the one or more target sites with respect to the first and second locations.

In some embodiments, the first set of flexible support elements of the first segment conforms to and complements a shape of a first anatomical structure at the first location when the first segment is in the deployed configuration and the second set of flexible support elements of the second segment conforms to and complements a shape of a second anatomical structure at the second location when the second segment is in the deployed configuration. The first and second anatomical structures may include, but are not limited to, inferior turbinate, medial turbinate, superior turbinate, inferior meatus, middle meatus, superior meatus, and sphenopalatine foramen.

In some embodiments, the first segment of the end effector is configured in a deployed configuration to fit around at least a portion of a middle turbinate at an anterior position relative to the middle turbinate and the second segment of the end effector is configured in a deployed configuration to contact a plurality of tissue locations in a cavity at a posterior position relative to the middle turbinate. For example, the first set of flexible support elements of the first segment conforms to and complements a shape of a lateral attachment of the middle turbinate at the anterior position when the first segment is in the deployed configuration and the second set of flexible support elements of the second segment conforms to and complements a shape of at least a second anatomical structure in the cavity posterior to the lateral attachment of the middle turbinate when the second segment is in the deployed configuration. Accordingly, when in the deployed configuration, the first and second segments are configured to position one or more of respective first and second sets of electrodes at one or more target sites relative to the middle turbinate and the plurality of tissue locations in the cavity behind the middle turbinate. In turn, the first and second sets of electrodes deliver RF energy at a level sufficient to therapeutically modulate postganglionic parasympathetic nerves innervating nasal mucosa at an innervation pathway within the nasal cavity of the patient.

Another aspect of the invention provides a method for treating a condition within a nasal cavity of a patient. The method includes providing a treatment device comprising an end effector transformable between a retracted configuration and an expanded deployed configuration, a shaft operably associated with the end effector, and a handle operably associated with the shaft. The handle comprises a first mechanism for deployment of the end effector from the retracted configuration to the expanded deployed configuration and a second mechanism, separate from the first mechanism, for control of energy output by the end effector. The method includes advancing the end effector to one or more target sites within the nasal cavity of the patient, the end effector configured for delivering energy to one or more target sites within the nasal cavity. The method further includes deploying, via user input with the first mechanism on the handle, the end effector at the one or more target sites and delivering energy from the end effector, via user input with the second mechanism, to tissue at the one or more target sites.

In some embodiments, the handle comprises a shape associated with the architecture of the end effector in the deployed configuration. For example, the handle may generally include a grip portion having a shape that provides a user with a physical confirmation of an orientation of portions of the end effector when in the deployed configuration. Accordingly, during advancement of the end effector to the one or more target sites within the nasal cavity, the method further includes positioning the end effector at the one or more target sites based, at least in part, on orientation of the handle.

In some embodiments, the handle and/or the shaft may include one or more markings that provide a user with a spatial orientation of the end effector while the end effector is in a nasal cavity. For example, one or more markings on the handle or shaft may provide a visual indication of the orientation of one or more portions of the end effector, specifically an indication of the spatial orientation of one or both of the first and second segments of the end effector in the deployed configurations. The markings may include any visual mark, such as text, symbols, and color-coding insignia. In some embodiments, multiple markings may be provided to provide visual indication of one or more portions of the first and second segments when in deployed configurations. Accordingly, during advancement of the end effector to the one or more target sites within the nasal cavity, the method further includes positioning the end effector at the one or more target sites based, at least in part, on orientation of the handle or the shaft and the one or more markings arranged about the handle or shaft.

Another aspect of the invention provides a device for treating a condition within a nasal cavity of a patient. The device includes a multi-segment end effector comprising at least a first retractable and expandable segment comprising a micro-electrode array arranged about a plurality of struts. The plurality of struts have a bilateral geometry conforming to and accommodating an anatomical structure within the nasal cavity when the first segment is in an expanded state. In particular, when in the expanded state, the plurality of struts contact multiple locations along multiple portions of the anatomical structure and electrodes of the micro-electrode array are configured to emit energy at a level sufficient to create multiple micro-lesions in tissue of the anatomical structure that interrupt neural signals to mucus producing and/or mucosal engorgement elements.

In some embodiments, the bilateral geometry comprises at least first strut that conforms to and accommodates a first side of the anatomical structure and at least a second strut that conforms to and accommodates a second side of the anatomical structure when the first segment is in the expanded state. When the first segment is in the expanded state, the first strut contacts multiple locations along the first side of the anatomical structure and a first set of electrodes of the micro-electrode array provided by the first strut is configured to emit energy at a level sufficient to create multiple respective micro-lesions in tissue along the first side of the anatomical structure. Similarly, when the first segment is in the expanded state, the second strut contacts multiple locations along the second side of the anatomical structure and a second set of electrodes of the micro-electrode array provided by the second strut are configured to emit energy at a level sufficient to create multiple respective micro-lesions in tissue along the second side of the anatomical structure. The anatomical structure may include, but is not limited to, an inferior turbinate, middle turbinate, superior turbinate, inferior meatus, middle meatus, superior meatus, pterygopalatine region, pterygopalatine fossa, sphenopalatine foramen, accessory sphenopalatine foramen(ae), and sphenopalatine micro-foramen(ae).

In some embodiments, each of the first and second struts has a loop shape and extends in an outward direction away from one another. The first and second struts comprise deformable composite wires, the composite wires comprising shape memory material. Each strut may include multiple electrodes of the electrode array positioned at separate and discrete portions of the strut. As such, when in the expanded state, each strut may position at least one associated electrode of the micro-electrode array into contact with tissue at a separate respective location on a respective side of the anatomical structure for delivery of energy thereto. The electrodes of the micro-electrode array are configured to be independently activated and controlled to thereby deliver energy independent of one another.

Another aspect of the invention provides a system for treating a condition within a nasal cavity of a patient. The system includes a device comprising a multi-segment end effector for delivering energy to one or more target sites within the nasal cavity of the patient and further sensing one or more properties of the one or more target sites. The multi-segment end effector includes a proximal segment that is spaced apart from a distal segment, wherein each of the proximal and distal segments has a specific geometry to complement anatomy at a respective location within the nasal cavity and associated with the one or more target sites. The system further includes a console unit operably associated with the device and configured to receive data from the device associated with the one or more properties of the one or more target sites and process data to provide information to an operator related to the one or more target sites.

The console unit is configured to provide information associated with at least one of: the identification and location of target and non-target neural structures at the one or more target sites prior to therapeutic modulation treatment thereof provided by at least one of the proximal and distal segments of the end effector; the identification and location of target and non-target anatomical structures at the one or more target sites prior to therapeutic modulation treatment thereof provided by at least one of the proximal and distal segments of the end effector; real-time feedback associated with efficacy of therapeutic modulation treatment on the one or more target neural and/or anatomic structures during therapeutic modulation treatment; and feedback associated with efficacy of therapeutic modulation treatment on the one or more target neural and/or anatomic structures after therapeutic modulation treatment.

In some embodiments, each of the proximal and distal segments of the end effector comprises flexible struts and a plurality of elements provided by the struts.

For example, a first subset of the of the plurality of elements may be configured to deliver non-therapeutic stimulating energy to tissue at the one or more target sites at a frequency for locating at least one of target neural structures, non-target neural structures, target anatomical structures, and non-target anatomical structures. A second subset of the plurality of elements may be configured to sense properties of at least one of the target neural structures, non-target neural structures, target anatomical structures, and non-target anatomical structures in response to the stimulating energy. The properties may include, but are not limited to, at least one of a physiological properties, bioelectric properties, and thermal properties. The bioelectric properties may include, but are not limited to, at least one of complex impedance, resistance, reactance, capacitance, inductance, permittivity, conductivity, nerve firing voltage, nerve firing current, depolarization, hyperpolarization, magnetic field, and induced electromotive force.

In some embodiments, the proximal segment of the end effector comprises a first set of flexible struts arranged in a first configuration and the distal segment of the end effector comprises a second set of flexible struts arranged in a second configuration. Each of the proximal and distal segments may be transformable between a retracted configuration and an expanded deployed configuration such that the first set of flexible struts conforms to and complements a shape of a first anatomical structure at a first location when the proximal segment is in the deployed configuration and the second set of flexible struts conforms to and complements a shape of a second anatomical structure at a second location when the distal segment is in the deployed configuration. The first and second anatomical structures may include, but are not limited to, an inferior turbinate, middle turbinate, superior turbinate, inferior meatus, middle meatus, superior meatus, pterygopalatine region, pterygopalatine fossa, sphenopalatine foramen, accessory sphenopalatine foramen(ae), and sphenopalatine micro-foramen(ae).

The first set of flexible struts and the second set of flexible struts may be configured to position one or more of the respective plurality of elements provided by each at respective one or more target sites when in the deployed configurations. For example, when in the expanded deployed configuration, the first set of flexible struts may include a first pair of struts, each comprising a loop shape and extending upward and a second pair of struts, each comprising a loop shape and extending downward. When in the expanded deployed configuration, the second set of flexible struts may include a second set of struts, each comprising a loop shape extending outward to form an open-ended circumferential shape. As such, the first and second sets of flexible struts may generally include deformable composite wires, wherein the composite wires comprise shape memory material.

In some embodiments, the console unit is configured to detect and/or map locations of at least one of the target neural structures, non-target neural structures, target anatomical structures, and non-target anatomical structures and control the delivery of therapeutic energy from at least one of the proximal and distal segments of the end effector in a modulation pattern based on the locations of at least one of the target neural structures, non-target neural structures, target anatomical structures, and non-target anatomical structures. At least some of the elements provided by at least one of the proximal and distal segments are configured to deliver energy based on the modulation pattern at a level sufficient to therapeutically modulate one or more nerves associated with the locations of the target neural and/or target anatomical structures while avoiding locations of the non-target neural and/or target anatomical structures. The at least some of the elements are configured to delivery energy based on the modulation pattern at a level insufficient to therapeutically modulate the non-target neural and/or non-target anatomical structures.

In some embodiments, the console unit comprises a controller configured to selectively control energy output from elements of the proximal and/or distal segments of the end effector, wherein some of the elements are configured to be independently activated and controlled to thereby deliver energy independent of one another. The controller may be configured to adjust energy output from elements of the proximal and/or distal segments of the end effector based, at least in part, on the real-time feedback associated with the effectiveness of therapeutic modulation treatment on the one or more target anatomic and/or neural structures during therapeutic modulation thereof.

Another aspect of the invention provides a method for treating a condition within a nasal cavity of a patient. The method includes providing a treatment device comprising a multi-segment end effector, including a proximal segment that is spaced apart from a distal segment, and a visual marker. The method further includes advancing, under image guidance, the proximal segment and the distal segment through a nasal cavity of a patient and past a middle turbinate and deploying the distal segment from a retracted configuration to an expanded configuration. The proximal segment is then aligned, under the image guidance and with reference to the visual marker, with respect to the middle turbinate. Upon alignment, the method includes deploying the proximal segment around the middle turbinate. The method further includes advancing the deployed proximal segment toward the middle turbinate to establish contact and secure the proximal segment to the middle turbinate.

The deployed proximal segment has a geometry to complement a shape of the middle turbinate and/or a lateral attachment of the middle turbinate, thereby ensuring that the deployed proximal segment is secured to the middle turbinate and/or lateral attachment of the middle turbinate. For example, in some embodiments, the proximal segment comprises a set of flexible support elements that conform to and complement a shape of the middle turbinate and/or the lateral attachment of the middle turbinate when the proximal segment is in the deployed expanded configuration.

The method may further include delivering energy, via the proximal segment, to the middle turbinate and/or a lateral attachment of the middle turbinate and/or a lateral wall of the nasal cavity to treat a condition. The condition may include, but is not limited to, allergic rhinitis, non-allergic rhinitis, chronic rhinitis, acute rhinitis, chronic sinusitis, acute sinusitis, chronic rhinosinusitis, acute rhinosinusitis, and medical resistant rhinitis, and a combination thereof. In some embodiments, delivering energy from the proximal segment includes delivering radiofrequency (RF) energy, via one or more electrodes provided by the proximal segment, to tissue of the lateral wall around the middle turbinate at one or more target sites, wherein the one or more target sites are associated with one or more neurogenic pathways. In some embodiments, RF energy is delivered, via the one or more electrodes provided by the proximal segment, at a level sufficient to disrupt one or more neurogenic pathways associated with the condition, such as neurogenic pathways that result in rhinorrhea and/or congestion. In other embodiments, RF energy is delivered, via the one or more electrodes provided by the proximal segment, at a level sufficient to therapeutically modulate one or more postganglionic parasympathetic nerves innervating nasal mucosa at a neurogenic pathway.

In some embodiments, the visual marker is provided by a shaft operably associated with the multi-segment end effector. The visual marker provides a visual indication of a spatial orientation of one or more portions of the proximal segment. The visual marker may include, for example, text, symbols, color-coding insignia, or the like. In some embodiments, the step of aligning the proximal segment with respect to the middle turbinate comprises positioning, under the image guidance, the shaft and associated visual marker relative to the middle turbinate, and/or a posterior lateral attachment of the middle turbinate and/or a lateral nasal wall.

Another aspect of the invention provides a system for treating a condition within a nasal cavity of a patient. The system includes a treatment device and an image guidance assembly for providing visual depictions of one or more portions of the treatment device to aid a user (i.e., surgeon or other medical professional) in carrying out a procedure for treating the condition with the nasal cavity of the patient.

The treatment device includes a multi-segment end effector comprising proximal segment that is spaced apart from a distal segment, a shaft operably associated with the multi-segment end effector, and a handle operably associated with the multi-segment end effector and the shaft. The shaft includes one or more visual markers for providing a user with a visual indication, under the image guidance, of a spatial orientation of at least the proximal segment while the multi-segment end effector is within in a nasal cavity of a patient. The handle includes a controller mechanism for providing independent, controlled deployment of each of the proximal and distal segments from a retracted configuration to an expanded configuration within the nasal cavity. The image guidance assembly provides a visual depiction of at least the shaft and visual marker relative to surrounding anatomy of the nasal cavity to thereby assist a user in deployment and positioning of at least the proximal segment within the nasal cavity.

In some embodiments, at least one visual marker is associated with a spatial orientation of a portion of the proximal segment when the proximal segment is in an expanded configuration. The visual marker may include, for example, text, symbols, color-coding insignia, or the like.

The proximal segment may include a geometry to complement a shape of the middle turbinate and/or a lateral attachment of the middle turbinate when in the expanded configuration, thereby ensuring that the deployed proximal segment may establish sufficient contact with, and be securely engaged to, the middle turbinate and/or the lateral attachment of the middle turbinate. For example, the proximal segment may include a set of flexible support elements that conform to and complement a shape of the middle turbinate and/or the lateral attachment of the middle turbinate when the proximal segment is in the expanded configuration. The distal segment may include a geometry to complement a shape of another anatomical structure within the nasal cavity when in an expanded configuration.

In some embodiments, the controller mechanism includes a rack and pinion assembly providing movement of the at least one of the proximal and distal segments between the retracted configuration and expanded configuration in response to user input from an associated user-operated controller. The rack and pinion assembly may include, for example, a set of gears for receiving user input from the user-operated controller and converting the user input to linear motion of a rack member operably associated with the multi-segment end effector.

In some embodiments, the controller mechanism may further include a detent feature positioned relative to the proximal and distal segments and configured to provide active feedback to a user indicative of deployment of at least one of the proximal and distal segments. The active feedback may be in the form haptic feedback provided by the controller mechanism. For example, the haptic feedback may include an increase or decrease in resistance associated with user input with the controller mechanism for corresponding movement of the at least one of the proximal and distal segments between retracted and expanded configurations, and/or configurations therebetween (i.e., a plurality of configurations between a fully retracted configuration and a fully expanded configuration).

In some embodiments, the controller mechanism may further include a friction-based feature configured to provide stable movement of at least one of the proximal and distal segments between the retracted and expanded configurations and further provide active feedback to a user indicative of deployment of at least one of the proximal and distal segments. The friction-based feature may include a lock mechanism providing constant friction between one or more portions of the rack and pinion assembly sufficient to maintain a position of at least one of the proximal and distal segments during deployment thereof. For example, the constant friction may be sufficient to hold either of the proximal or distal segments in a certain position as the segment transitions between retracted and expanded configurations regardless of whether the user maintains contact with the user-operated controller. In other words, a user does not need to maintain contact with the user-operated controller in order to ensure that the proximal or distal segment holds a certain position during deployment thereof. Rather, a user can simply interact with the user-operated controller to transition one of the proximal and distal segments to a desired configuration and the constant friction provided by the locking mechanism is sufficient to maintain the configuration of proximal or distal segment in the event that the user goes hands free (i.e., removes any contact with the user-operated controller). The constant friction is of a level sufficient to prevent undesired movement of the proximal or distal segments (i.e., unintended collapsing or expanding), while still allowing for a user to overcome such friction to move the proximal or distal segment to a desired configuration upon user input with the user-operated controller.

In some embodiments, the user-operated controller includes a slider mechanism operably associated with the rack and pinion rail assembly, wherein movement of the slider mechanism in a first direction results in transitioning of at least one of the proximal and distal segments to an expanded configuration and movement of the slider mechanism in a second opposite direction results in transitioning of at least one of the proximal and distal segments to the retracted configuration.

In other embodiments, the user-operated controller includes a scroll wheel mechanism operably associated with the rack and pinion rail assembly, wherein rotation of the wheel in a first direction results in transitioning of at least one of the proximal and distal segments to an expanded configuration and rotation of the wheel in a second opposite direction results in transitioning of at least one of the proximal and distal segments to the retracted configuration.

BRIEF DESCRIPTION OF THE DRAWINGS

FIGS. 1A and 1B are diagrammatic illustrations of a therapeutic neuromodulation system for treating a condition within a nasal cavity using a handheld device according to some embodiments of the present disclosure.

FIG. 13 is a flow diagram illustrating one embodiment of a method for treating a condition within a nasal cavity of a patient.

FIG. 15 is a flow diagram illustrating another embodiment of a method for treating a condition within a nasal cavity of a patient.

DETAILED DESCRIPTION

Figure 2:
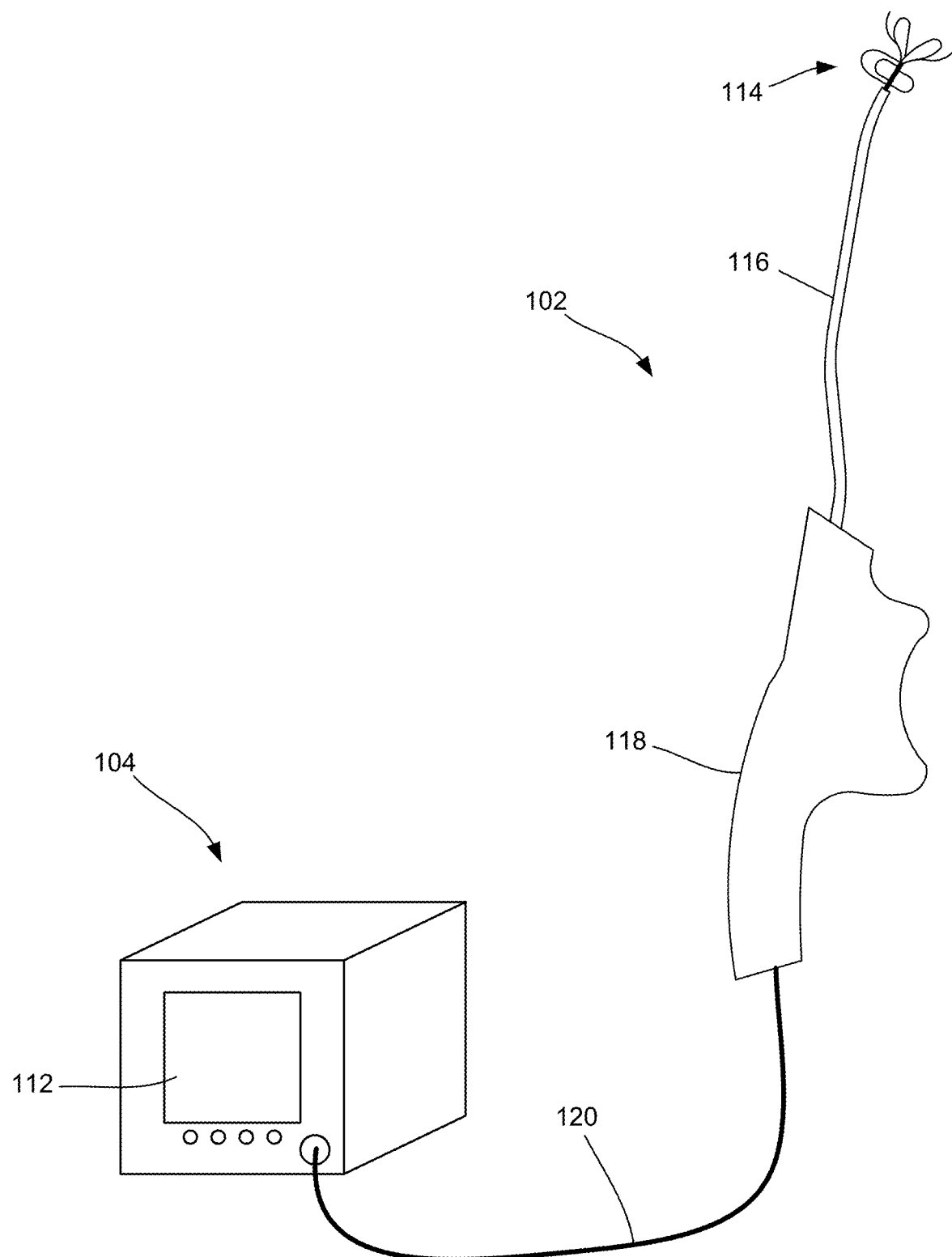
FIG. 2 is a diagrammatic illustration of the console coupled to the handheld neuromodulation device consistent with the present disclosure, further illustrating a multi-segment end effector of the handheld device for delivering energy, via proximal and distal segments, to tissue at the one or more target sites within the nasal cavity.

There are various conditions related to the nasal cavity which may impact breathing and other functions of the nose. One of the more common conditions is rhinitis, which is defined as inflammation of the membranes lining the nose. The symptoms of rhinitis include nasal blockage, obstruction, congestion, nasal discharge (e.g., rhinorrhea and/or posterior nasal drip), facial pain, facial pressure, and/or reduction or complete loss of smell and/or taste. Sinusitis is another common condition, which involves an inflammation or swelling of the tissue lining the sinuses, which can lead to subsequent. Rhinitis and sinusitis are frequently associated with one another, as sinusitis is often preceded by rhinitis. Accordingly, the term rhinosinusitis is often used to describe both conditions.

Depending on the duration and type of systems, rhinosinusitis can fall within different subtypes, including allergic rhinitis, non-allergic rhinitis, chronic rhinitis, acute rhinitis, recurrent rhinitis, chronic sinusitis, acute sinusitis, recurrent sinusitis, and medical resistant rhinitis and/or sinusitis, in addition to combinations of one or more of the preceding conditions. It should be noted that an acute rhinosinusitis condition is one in which symptoms last for less than twelve weeks, whereas a chronic rhinosinusitis condition refers to symptoms lasting longer than twelve weeks.

A recurrent rhinosinusitis condition refers to four or more episodes of an acute rhinosinusitis condition within a twelve-month period, with resolution of symptoms between each episode. There are numerous environmental and biological causes of rhinosinusitis. Non-allergic rhinosinusitis, for example, can be caused by environmental irritants, medications, foods, hormonal changes, and/or nasal septum deviation. Triggers of allergic rhinitis can include exposure to seasonal allergens, perennial allergens that occur any time of year, and/or occupational allergens. Accordingly, rhinosinusitis affects millions of people and is a leading cause for patients to seek medical care.

The present invention provides systems and methods for therapeutically modulating nerves in a nasal region of a patient for the effective treatment of rhinosinusitis conditions. Particularly, aspects of the present invention include systems and methods for performing an accurate, minimally invasive, and localized application of energy to one or more target sites within the nasal cavity to disrupt the parasympathetic motor sensory function associated with rhinosinusitis conditions, without causing collateral damage or disruption to other neural structures.

It should be noted that, although many of the embodiments are described with respect to devices, systems, and methods for therapeutically modulating nerves in the nasal region for the treatment of rhinitis, other applications and other embodiments in addition to those described herein are within the scope of the present disclosure. For example, at least some embodiments of the present disclosure may be useful for the treatment of other indications, such as the treatment of chronic sinusitis and epistaxis. In particular, the embodiments described herein may be configured to treat allergic rhinitis, non-allergic rhinitis, chronic rhinitis, acute rhinitis, chronic sinusitis, acute sinusitis, chronic rhinosinusitis, acute rhinosinusitis, and/or medical resistant rhinitis.

FIGS. 1A and 1B are diagrammatic illustrations of a therapeutic neuromodulation system 100 for treating a condition within a nasal cavity using a handheld device 102 according to some embodiments of the present disclosure. The system 100 generally includes a neuromodulation device 102 and a neuromodulation console 104 to which the device 102 is to be connected. FIG. 2 is a diagrammatic illustration of the console 104 coupled to the handheld neuromodulation device 102. As illustrated, the neuromodulation device 102 is a handheld device, which includes a retractable and expandable multi-segment end effector 114, a shaft 116 operably associated with the end effector 114 and a handle 118 operably associated with the shaft 116. The end effector 114 is configured to be advanced into the nasal cavity of a patient 12 and positioned at a location associated with one or more target sites to undergo therapeutic neuromodulation treatment. It should be noted that the terms "end effector" and "therapeutic assembly" may be used interchangeably throughout this disclosure.

For example, a surgeon or other medical professional performing a procedure can utilize the handle 118 to manipulate and advance the shaft 116 within the nasal cavity, wherein the shaft 116 is configured to locate at least a distal portion thereof intraluminally at a treatment or target site within a nasal region. The one or more target sites may generally be associated with postganglionic parasympathetic fibers that innervate the nasal mucosa. The target site may be a region, volume, or area in which the target nerves are located and may differ in size and shape depending upon the anatomy of the patient. Once positioned, the end effector 114 may be deployed and subsequently deliver energy to the one or more target sites to thereby therapeutically modulating nerves of interest, particularly nerves associated with a rhinosinusitis condition so as to treat such condition. For example, the end effector 114 may include at least one energy delivery element, such as an electrode, configured to therapeutically modulate the postganglionic parasympathetic nerves. For example, one or more electrodes may be provided by one or more portions of the end-effector 114, wherein the electrodes may be configured to apply electromagnetic neuromodulation energy (e.g., radiofrequency (RF) energy) to target sites. In other embodiments, the end effector 114 may include other energy delivery elements configured to provide therapeutic neuromodulation using various other modalities, such as cryotherapeutic cooling, ultrasound energy (e.g., high intensity focused ultrasound ("HIFU") energy), microwave energy (e.g., via a microwave antenna), direct heating, high and/or low power laser energy, mechanical vibration, and/or optical power.

In some embodiments, the end effector 114 may include one or more sensors (not shown), such as one or more temperature sensors (e.g., thermocouples, thermistors, etc.), impedance sensors, and/or other sensors. The sensors and/or the electrodes may be connected to one or more wires extending through the shaft 116 and configured to transmit signals to and from the sensors and/or convey energy to the electrodes.

As shown, the device 102 is operatively coupled to the console 104 via a wired connection, such as cable 120. It should be noted, however, that the device 102 and console 104 may be operatively coupled to one another via a wireless connection. The console 104 is configured to provide various functions for the neuromodulation device 102, which may include, but is not limited to, controlling, monitoring, supplying, and/or otherwise supporting operation of the neuromodulation device 102. For example, when the neuromodulation device 102 is configured for electrode-based, heat-element-based, and/or transducer-based treatment, the console 104 may include an energy generator 106 configured to generate RF energy (e.g., monopolar, bipolar, or multi-polar RF energy), pulsed electrical energy, microwave energy, optical energy, ultrasound energy (e.g., intraluminally-delivered ultrasound and/or HIFU), direct heat energy, radiation (e.g., infrared, visible, and/or gamma radiation), and/or another suitable type of energy.

In some embodiments, the console 104 may include a controller 107 communicatively coupled to the neuromodulation device 102. However, in the embodiments described herein, the controller 107 may generally be carried by and provided within the handle 118 of the neuromodulation device 102. The controller 107 is configured to initiate, terminate, and/or adjust operation of one or more electrodes provided by the end effector 114 directly and/or via the console 104. For example, the controller 107 can be configured to execute an automated control algorithm and/or to receive control instructions from an operator (e.g., surgeon or other medical professional or clinician). For example, the controller 107 and/or other components of the console 104 (e.g., processors, memory, etc.) can include a computer-readable medium carrying instructions, which when executed by the controller 107, causes the device 102 to perform certain functions (e.g., apply energy in a specific manner, detect impedance, detect temperature, detect nerve locations or anatomical structures, etc.). A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory.

The console 104 may further be configured to provide feedback to an operator before, during, and/or after a treatment procedure via evaluation/feedback algorithms 110. For example, the evaluation/feedback algorithms 110 can be configured to provide information associated with the temperature of the tissue at the treatment site, the location of nerves at the treatment site, and/or the effect of the therapeutic neuromodulation on the nerves at the treatment site. In certain embodiments, the evaluation/feedback algorithm 110 can include features to confirm efficacy of the treatment and/or enhance the desired performance of the system 100. For example, the evaluation/feedback algorithm 110, in conjunction with the controller 107, can be configured to monitor temperature at the treatment site during therapy and automatically shut off the energy delivery when the temperature reaches a predetermined maximum (e.g., when applying RF energy) or predetermined minimum (e.g., when applying cryotherapy). In other embodiments, the evaluation/feedback algorithm 110, in conjunction with the controller 107, can be configured to automatically terminate treatment after a predetermined maximum time, a predetermined maximum impedance rise of the targeted tissue (i.e., in comparison to a baseline impedance measurement), a predetermined maximum impedance of the targeted tissue), and/or other threshold values for biomarkers associated with autonomic function. This and other information associated with the operation of the system 100 can be communicated to the operator via a graphical user interface (GUI) 112 provided via a display on the console 104 and/or a separate display (not shown) communicatively coupled to the console 104, such as a tablet or monitor. The GUI 112 may generally provide operational instructions for the procedure, such as directing the operator to select which nasal cavity to treat, indicating when the device 102 is primed and ready to perform treatment, and further providing status of therapy during the procedure, including indicating when the treatment is complete.

For example, in some embodiments, the end effector 114 and/or other portions of the system 100 can be configured to detect various parameters of the heterogeneous tissue at the target site to determine the anatomy at the target site (e.g., tissue types, tissue locations, vasculature, bone structures, foramen, sinuses, etc.), locate nerves and/or other structures, and allow for neural mapping. For example, the end effector 114 may be configured to detect impedance, dielectric properties, temperature, and/or other properties that indicate the presence of neural fibers in the target region. As shown in FIG. 1, the console 104 may further include a monitoring system 108 configured to receive detected electrical and/or thermal measurements of tissue at the target site taken by the end effector 114, specifically sensed by appropriate sensors (e.g., temperature sensors and/or impedance sensors), and process this information to identify the presence of nerves, the location of nerves, and/or neural activity at the target site. The nerve monitoring system 108 can be operably coupled to the electrodes and/or other features of the end effector 102 via signal wires (e.g., copper wires) that extend through the cable 120 and through the length of the shaft 116. In other embodiments, the end effector 114 can be communicatively coupled to the nerve monitoring system 108 using other suitable communication means.

The nerve monitoring system 108 can determine neural locations and activity before therapeutic neuromodulation to determine precise treatment regions corresponding to the positions of the desired nerves, during treatment to determine the effect of the therapeutic neuromodulation, and/or after treatment to evaluate whether the therapeutic neuromodulation treated the target nerves to a desired degree. This information can be used to make various determinations related to the nerves proximate to the target site, such as whether the target site is suitable for neuromodulation. In addition, the nerve monitoring system 108 can also compare the detected neural locations and/or activity before and after therapeutic neuromodulation, and compare the change in neural activity to a predetermined threshold to assess whether the application of therapeutic neuromodulation was effective across the treatment site. For example, the nerve monitoring system 108 can further determine electroneurogram (ENG) signals based on recordings of electrical activity of neurons taken by the end effector 114 before and after therapeutic neuromodulation. Statistically meaningful (e.g., measurable or noticeable) decreases in the ENG signal(s) taken after neuromodulation can serve as an indicator that the nerves were sufficiently ablated. Additional features and functions of the nerve monitoring system 108, as well as other functions of the various components of the console 104, including the evaluation/feedback algorithms 110 for providing real-time feedback capabilities for ensuring optimal therapy for a given treatment is administered, are described in at least U.S. Publication No. 2016/0331459 and U.S. Publication No. 2018/0133460, the contents of each of which are incorporated by reference herein in their entireties.

As will be described in greater detail herein, the neuromodulation device 102 provides access to target sites deep within the nasal region, such as at the immediate entrance of parasympathetic fibers into the nasal cavity to therapeutically modulate autonomic activity within the nasal cavity. In certain embodiments, for example, the neuromodulation device 102 can position the end effector 114 into contact with target sites within nasal cavity associated with postganglionic parasympathetic fibers that innervate the nasal mucosa.

Figure 3A:
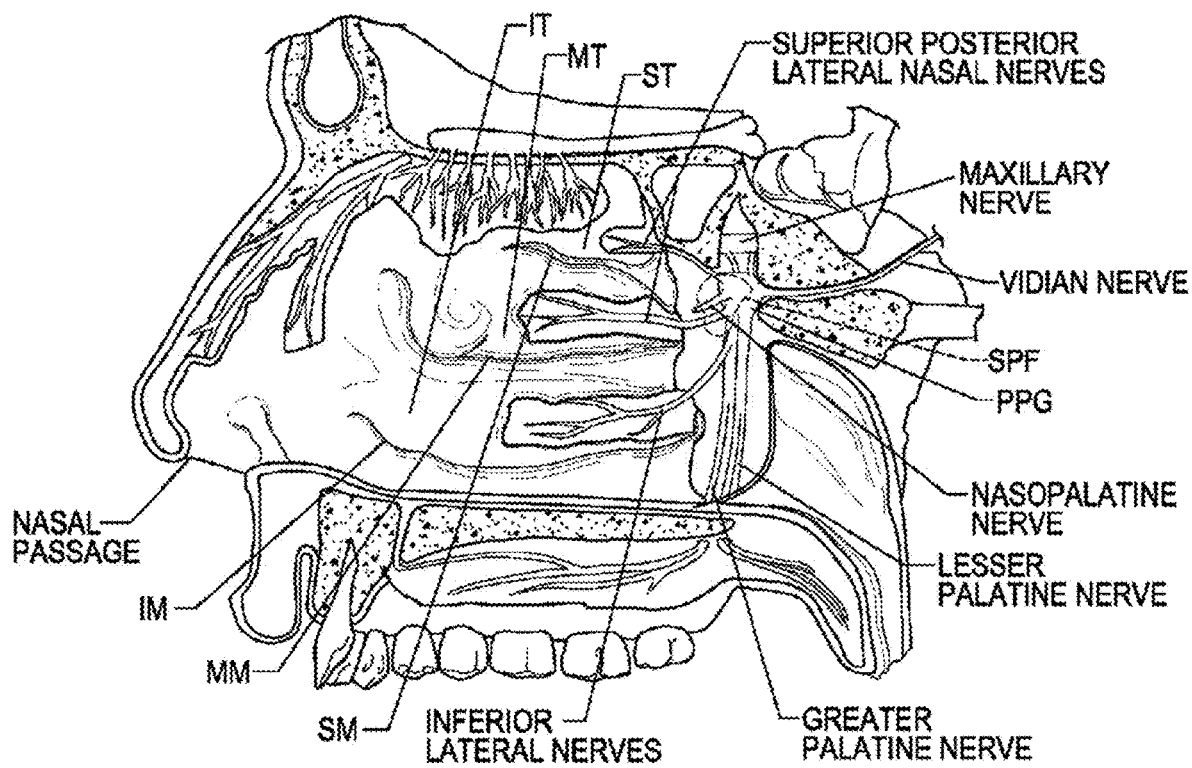
FIG. 3A is a cut-away side view illustrating the anatomy of a lateral nasal wall.
Figure 3B:
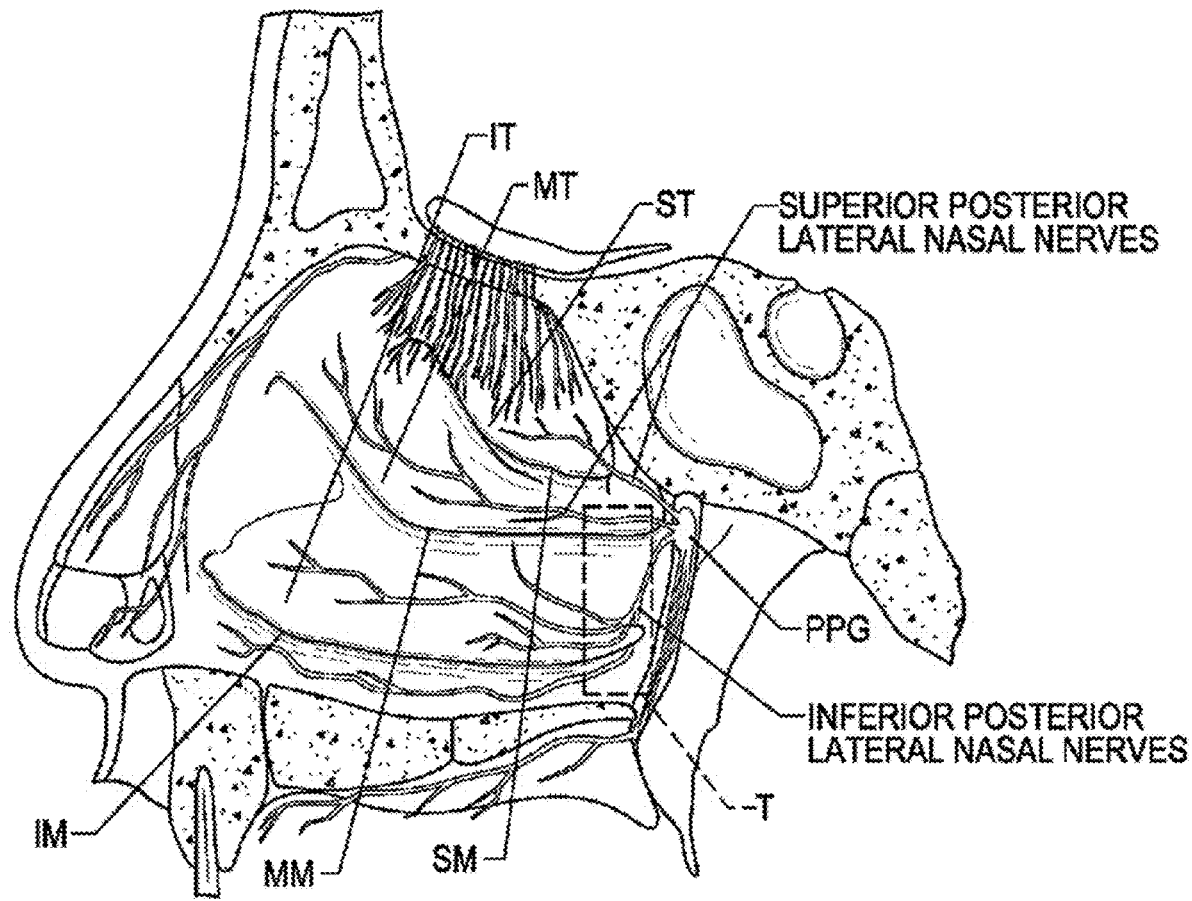
FIG. 3B is an enlarged side view of the nerves of the lateral nasal wall of FIG. 1A.

FIG. 3A is a cut-away side view illustrating the anatomy of a lateral nasal wall and FIG. 3B is an enlarged side view of the nerves of the lateral nasal wall of FIG. 1A. The sphenopalatine foramen (SPF) is an opening or conduit defined by the palatine bone and the sphenoid bone through which the sphenopalatine vessels and the posterior superior nasal nerves travel into the nasal cavity. More specifically, the orbital and sphenoidal processes of the perpendicular plate of the palatine bone define the sphenopalatine notch, which is converted into the SPF by the articulation with the surface of the body of the sphenoid bone.

The location of the SPF is highly variable within the posterior region of the lateral nasal cavity, which makes it difficult to visually locate the SPF. Typically, the SPF is located in the middle meatus (MM). However, anatomical variations also result in the SPF being located in the superior meatus (SM) or at the transition of the superior and middle meatuses. In certain individuals, for example, the inferior border of the SPF has been measured at about 19 mm above the horizontal plate of the palatine bone (i.e., the nasal sill), which is about 13 mm above the horizontal lamina of the inferior turbinate (IT) and the average distance from the nasal sill to the SPF is about 64.4 mm, resulting in an angle of approach from the nasal sill to the SPA of about 11.4°. However, studies to measure the precise location of the SPF are of limited practical application due to the wide variation of its location.

The anatomical variations of the SPF are expected to correspond to alterations of the autonomic and vascular pathways traversing into the nasal cavity. In general, it is thought that the posterior nasal nerves (also referred to as lateral posterior superior nasal nerves) branch from the pterygopalatine ganglion (PPG), which is also referred to as the sphenopalatine ganglion, through the SPF to enter the lateral nasal wall of the nasal cavity, and the sphenopalatine artery passes from the pterygopalatine fossa through the SPF on the lateral nasal wall. The sphenopalatine artery branches into two main portions: the posterior lateral nasal branch and the posterior septal branch. The main branch of the posterior lateral nasal artery travels inferiorly into the inferior turbinate IT (e.g., between about 1.0 mm and 1.5 mm from the posterior tip of the inferior turbinate IT), while another branch enters the middle turbinate MT and branches anteriorly and posteriorly.

Beyond the SPF, studies have shown that over 30% of human patients have one or more accessory foramen that also carries arteries and nerves into the nasal cavity. The accessory foramen are typically smaller than the SPF and positioned inferior to the SPF. For example, there can be one, two, three or more branches of the posterior nasal artery and posterior nasal nerves that extend through corresponding accessory foramen. The variability in location, size, and quantity associated with the accessory foramen and the associated branching arteries and nerves that travel through the accessory foramen gives rise to a great deal of uncertainty regarding the positions of the vasculature and nerves of the sphenopalatine region. Furthermore, the natural anatomy extending from the SPF often includes deep inferior and/or superior grooves that carry neural and arterial pathways, which make it difficult to locate arterial and neural branches. For example the grooves can extend more than 5 mm long, more than 2 mm wide, and more than 1 mm deep, thereby creating a path significant enough to carry both arteries and nerves. The variations caused by the grooves and the accessory foramen in the sphenopalatine region make locating and accessing the arteries and nerves (positioned posterior to the arteries) extremely difficult for surgeons.

Recent microanatomic dissection of the pterygopalatine fossa (PPF) have further evidenced the highly variable anatomy of the region surrounding the SPF, showing that a multiplicity of efferent rami that project from the pterygopalatine ganglion (PPG) to innervate the orbit and nasal mucosa via numerous groups of small nerve fascicles, rather than an individual postganglionic autonomic nerves (e.g., the posterior nasal nerve). Studies have shown that at least 87% of humans have microforamina and micro rami in the palatine bone.

Figure 3C:
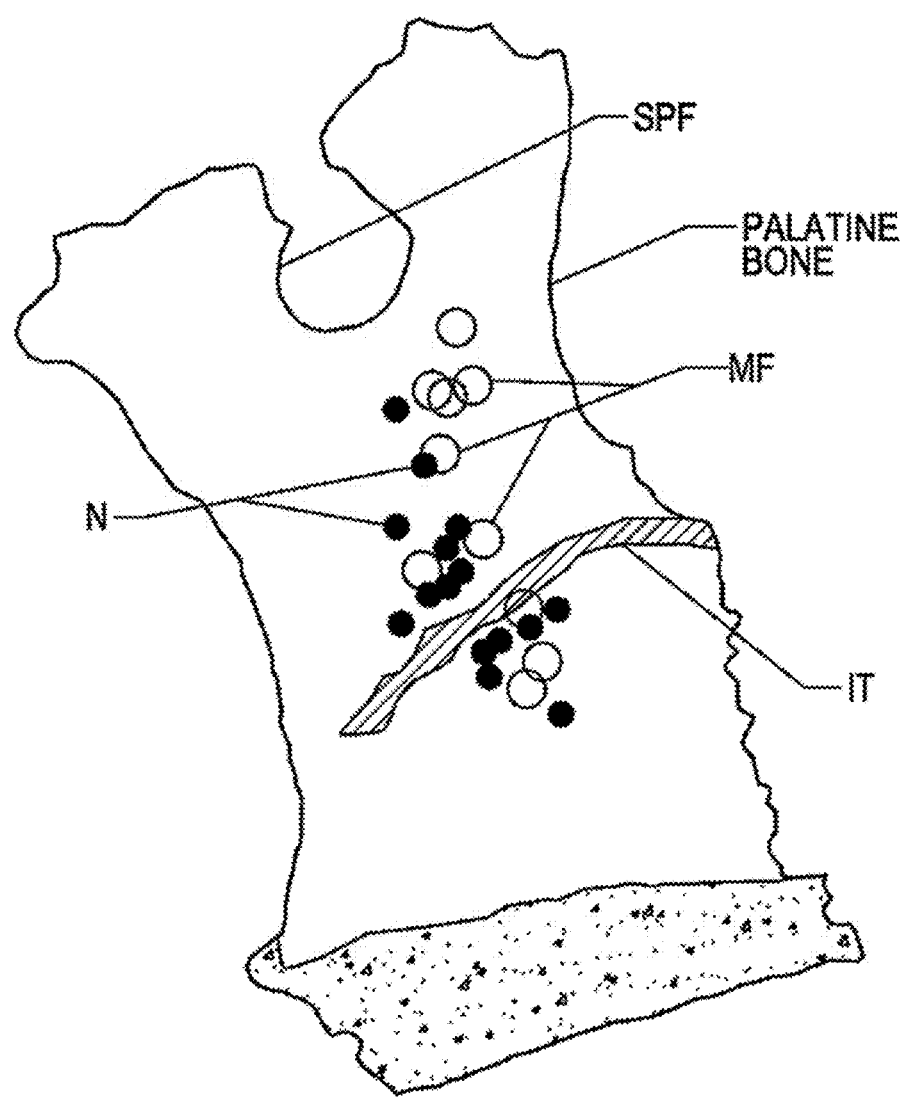
FIG. 3C is a front view of a left palatine bone illustrating geometry of microforamina in the left palatine bone.

FIG. 3C, for example, is a front view of a left palatine bone illustrating geometry of microforamina and micro rami in a left palatine bone. In FIG. 3C, the solid regions represent nerves traversing directly through the palatine bone, and the open circles represent nerves that were associated with distinct microforamina. As such, FIG. 3C illustrates that a medial portion of the palatine bone can include at least 25 accessory posterolateral nerves.

The respiratory portion of the nasal cavity mucosa is composed of a type of ciliated pseudostratified columnar epithelium with a basement membrane. Nasal secretions (e.g., mucus) are secreted by goblet cells, submucosal glands, and transudate from plasma. Nasal seromucous glands and blood vessels are highly regulated by parasympathetic innervation deriving from the vidian and other nerves. Parasympathetic (cholinergic) stimulation through acetylcholine and vasoactive intestinal peptide generally results in mucus production. Accordingly, the parasympathetic innervation of the mucosa is primarily responsible submucosal gland activation/hyper activation, venous engorgement (e.g., congestion), and increased blood flow to the blood vessels lining the nose. Accordingly, severing or modulating the parasympathetic pathways that innervate the mucosa are expected to reduce or eliminate the hyper activation of the submucosal glands and engorgement of vessels that cause symptoms associated with rhinosinusitis and other indications.

As previously described herein, postganglionic parasympathetic fibers that innervate the nasal mucosa (i.e., posterior superior nasal nerves) were thought to travel exclusively through the SPF as a sphenopalatine neurovascular bundle. The posterior nasal nerves are branches of the maxillary nerve that innervate the nasal cavity via a number of smaller medial and lateral branches extending through the mucosa of the superior and middle turbinates ST, MT (i.e., nasal conchae) and to the nasal septum. The nasopalatine nerve is generally the largest of the medial posterior superior nasal nerves, and it passes anteroinferiorly in a groove on the vomer to the floor of the nasal cavity. From here, the nasopalatine nerve passes through the incisive fossa of the hard palate and communicates with the greater palatine nerve to supply the mucosa of the hard palate. The posterior superior nasal nerves pass through the pterygopalatine ganglion PPG without synapsing and onto the maxillary nerve via its ganglionic branches.

Based on the understanding that the posterior nasal nerves exclusively traverse the SPF to innervate the nasal mucosa, surgeries have been performed to selectively sever the posterior nasal nerve as it exits the SPF. However, as discussed above, the sinonasal parasympathetic pathway actually comprises individual rami project from the pterygopalatine ganglion (PPG) to innervate the nasal mucosa via multiple small nerve fascicles (i.e., accessory posterolateral nerves), not a single branch extending through the SPF. These rami are transmitted through multiple fissures, accessory foramina, and microforamina throughout the palatine bone and may demonstrate anastomotic loops with both the SPF and other accessory nerves. Thus, if only the parasympathetic nerves traversing the SPF were severed, almost all patients (e.g., 90% of patients or more) would retain intact accessory secretomotor fibers to the posterolateral mucosa, which would result in the persistence of symptoms the neurectomy was meant to alieve.

Accordingly, embodiments of the present disclosure are configured to therapeutically modulate nerves at precise and focused treatment sites corresponding to the sites of rami extending through fissures, accessory foramina, and microforamina throughout the palatine bone (e.g., target region T shown in FIG. 3B). In certain embodiments, the targeted nerves are postganglionic parasympathetic nerves that go on to innervate the nasal mucosa. This selective neural treatment is also expected to decrease the rate of postoperative nasal crusting and dryness because it allows a clinician to titrate the degree of anterior denervation through judicious sparing of the rami orbitonasal. Furthermore, embodiments of the present disclosure are also expected to maintain at least some sympathetic tone by preserving a portion of the sympathetic contributions from the deep petrosal nerve and internal maxillary periarterial plexus, leading to improved outcomes with respect to nasal obstruction. In addition, embodiments of the present disclosure are configured to target a multitude of parasympathetic neural entry locations (e.g., accessory foramen, fissures, and microforamina) to the nasal region to provide for a complete resection of all anastomotic loops, thereby reducing the rate of long-term re-innervation.

Figure 4:
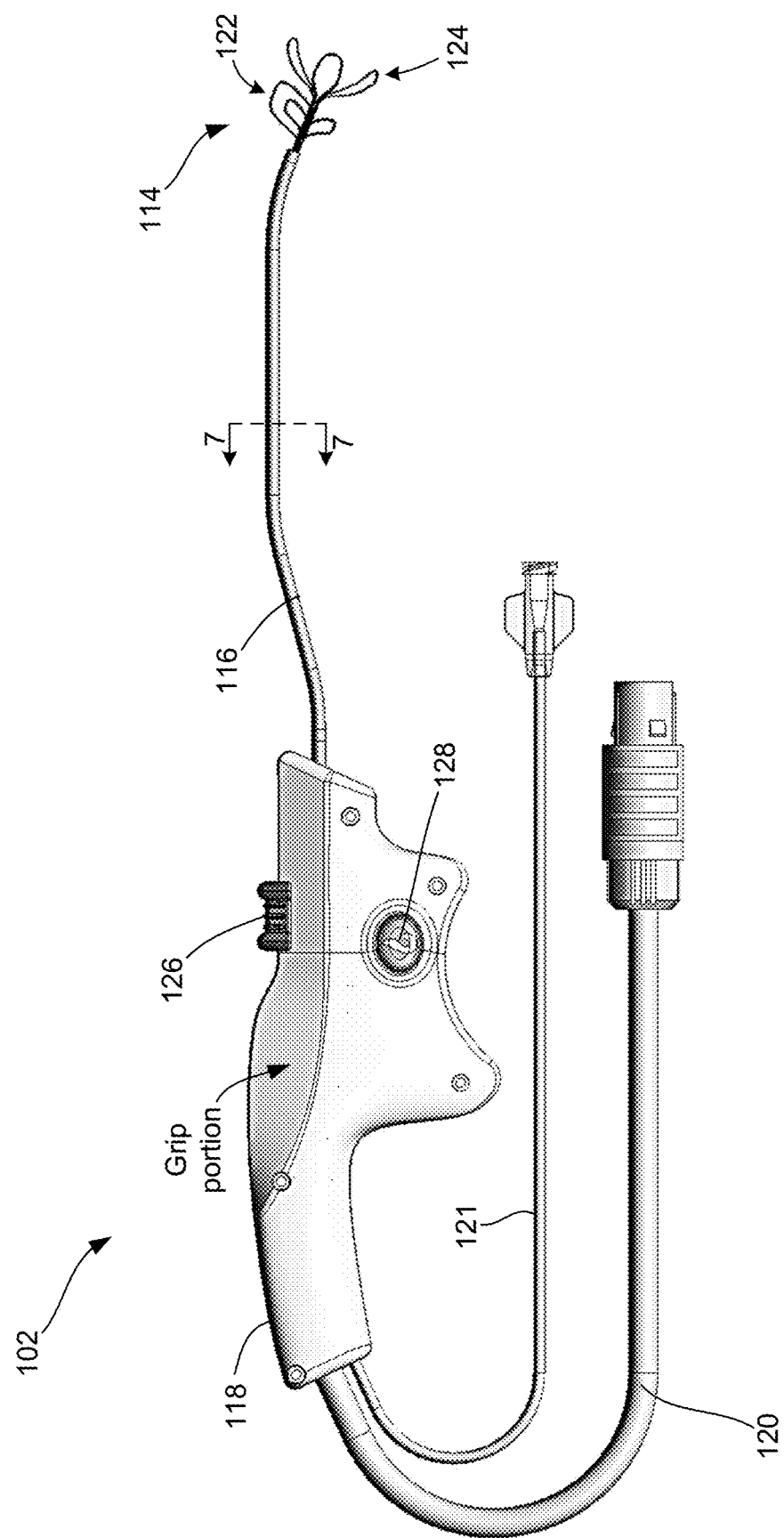
FIG. 4 is a side view of one embodiment of a handheld device for providing therapeutic nasal neuromodulation consistent with the present disclosure.

FIG. 4 is a side view of one embodiment of a handheld device 102 for providing therapeutic nasal neuromodulation consistent with the present disclosure. As illustrated, the device 102 includes a multi-segment end effector 114 transformable between a retracted configuration and an expanded deployed configuration, a shaft 116 operably associated with the end effector 114, and a handle 118 operably associated with the shaft 116. The multi-segment end effector 114 includes at least a first segment 122 and a second segment 124 spaced apart from one another. The first segment 122 is generally positioned closer to a distal end of the shaft 116, and is thus sometimes referred to herein as the proximal segment 122, while the second segment 124 is generally positioned further from the distal end of the shaft 116 and is thus sometimes referred to herein as the distal segment 124. Each of the first and second segments 122 and 124 is transformable between a retracted configuration, which includes a low-profile delivery state to facilitate intraluminal delivery of the end effector 114 to a treatment site within the nasal region, and a deployed configuration, which includes an expanded state, as shown in FIG. 4 and further illustrated in FIGS. 5A-5F. The handle 118 includes at least a first mechanism 126 for deployment of the multi-segment end effector 114, notably the first and second segments 122, 124, from the retracted configuration to the deployed configuration and a second mechanism 128, separate from the first mechanism 124, for control of energy output by either of the first and second segments 122, 124 of the end effector 114, specifically electrodes or other energy elements provided by first and/or second segments 122, 124. The handheld device 102 may further include an auxiliary line 121, which may provide a fluid connection between a fluid source, for example, and the shaft 116 such that fluid may be provided to a target site via the distal end of the shaft 116. In some embodiments, the auxiliary line 121 may provide a connection between a vacuum source and the shaft 116, such that the device 102 may include suction capabilities (via the distal end of the shaft 116).

Figure 5A:
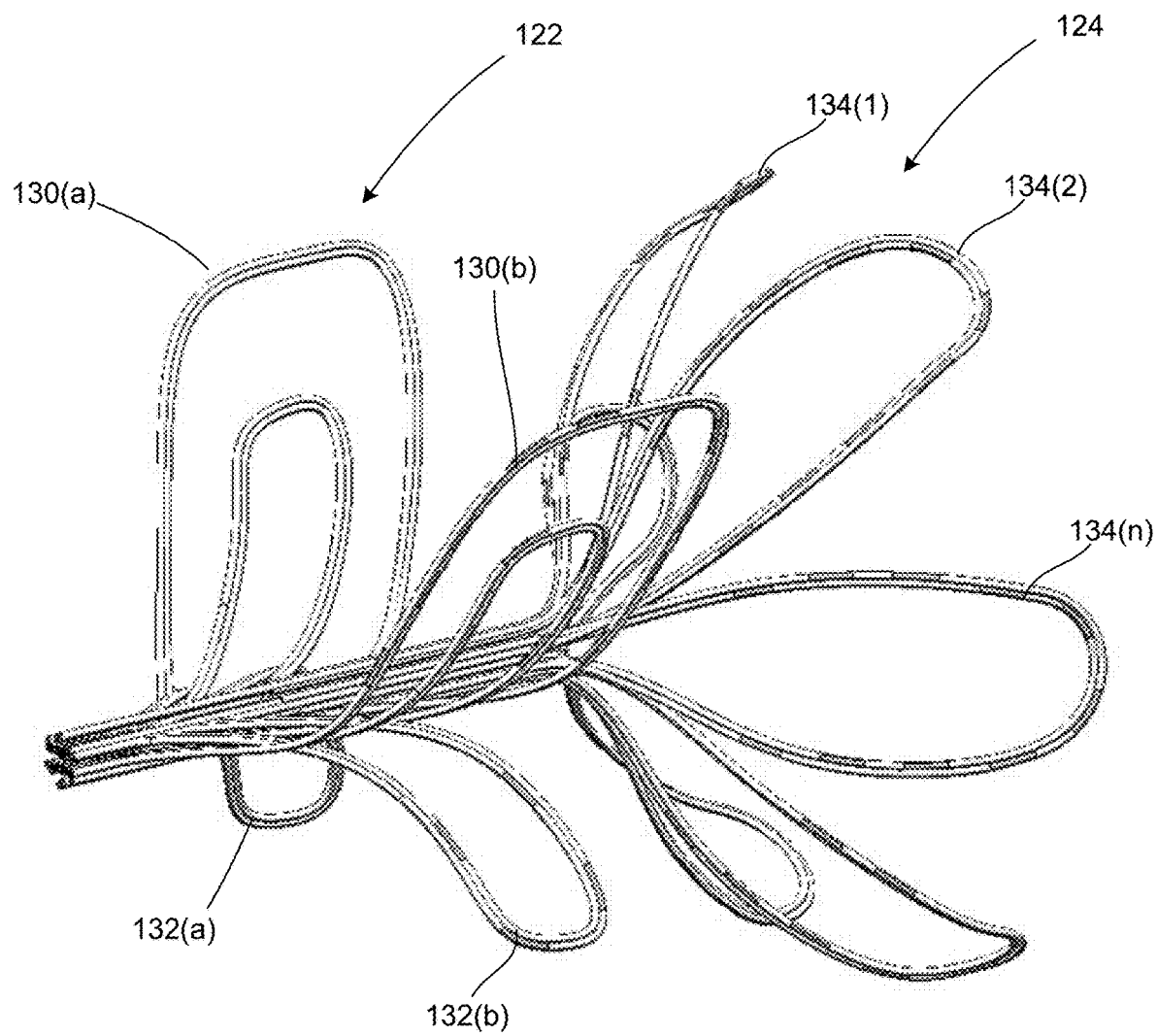
FIG. 5A is an enlarged, perspective view of the multi-segment end effector illustrating the first (proximal) segment and second (distal) segment.
Figure 5B:
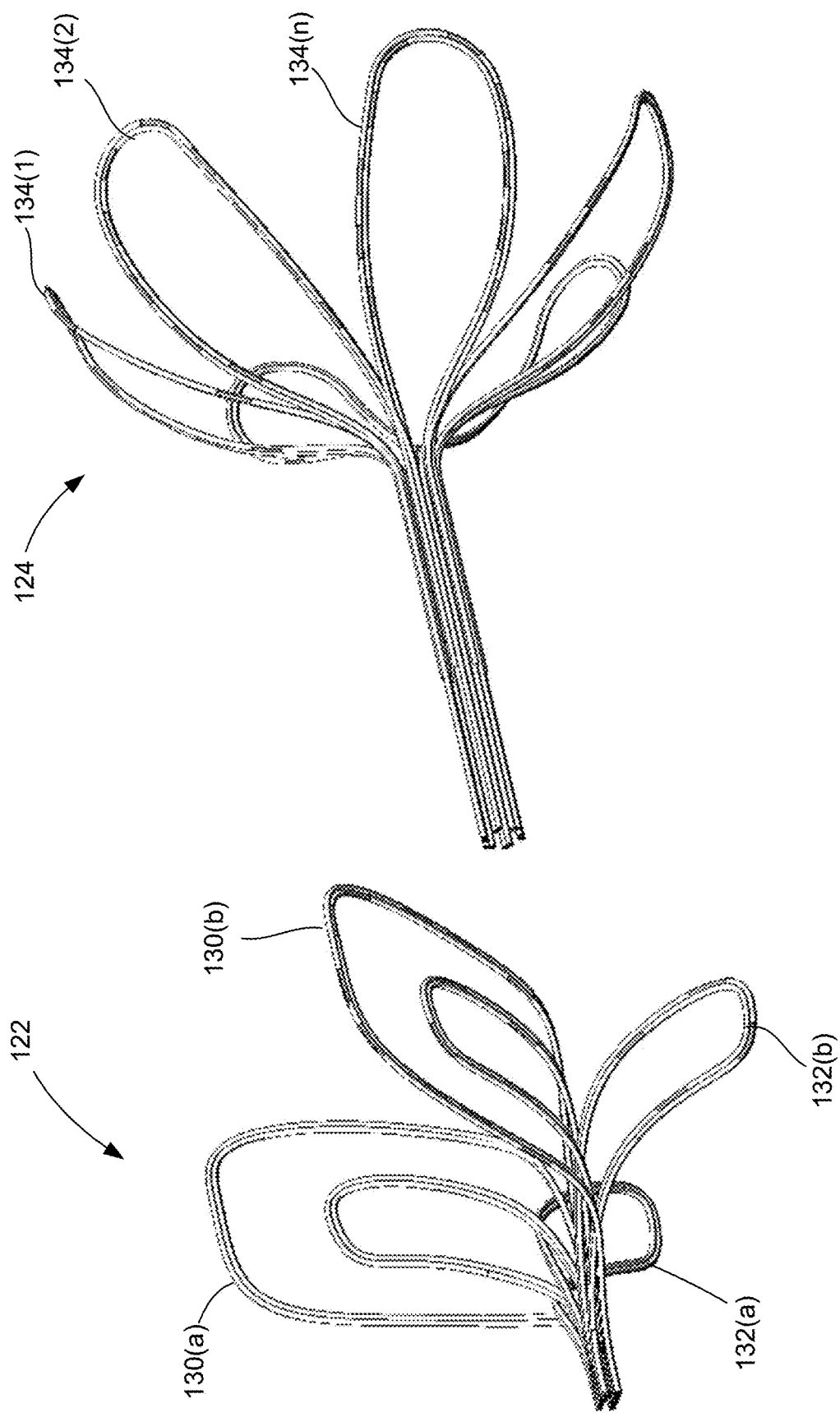
FIG. 5B is an exploded, perspective view of the multi-segment end effector.
Figure 5C:
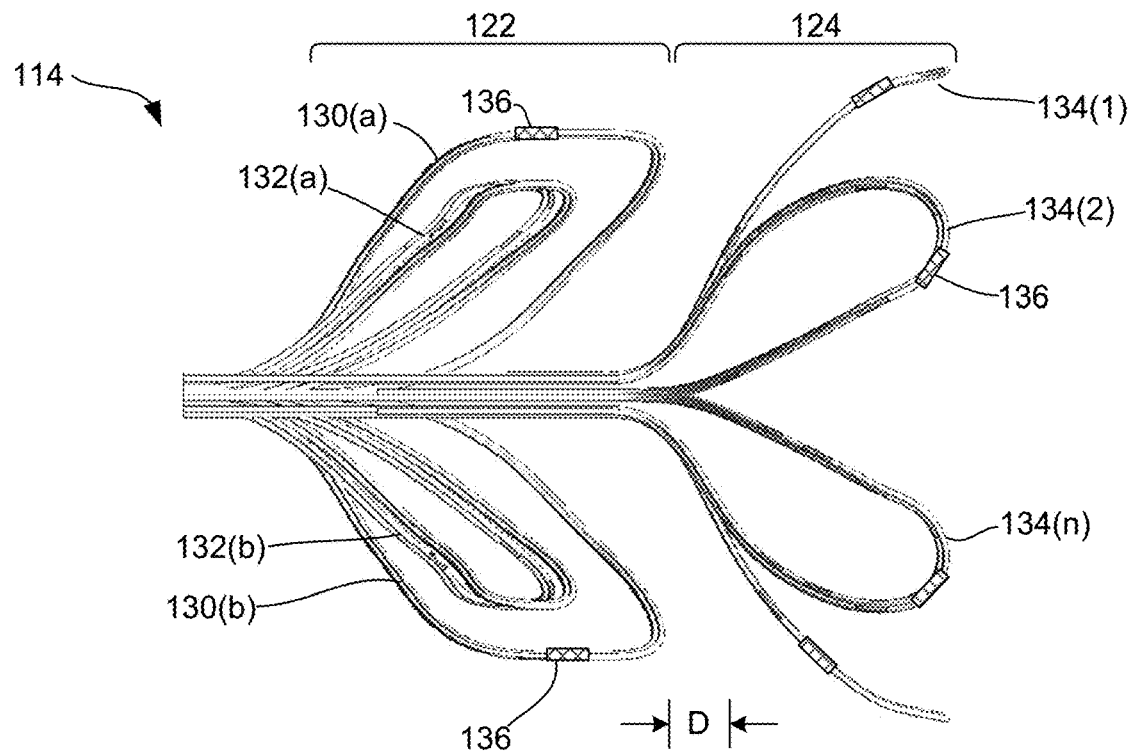
FIG. 5C is an enlarged, top view of the multi-segment end effector.
Figure 5D:
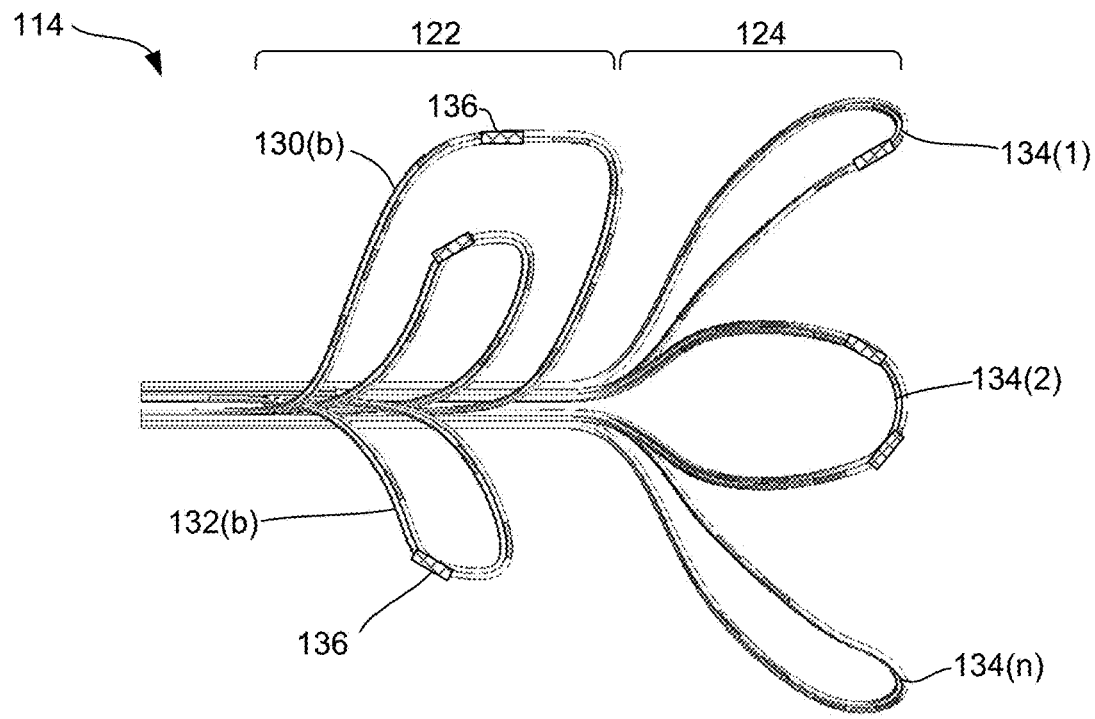
FIG. 5D is an enlarged, side view of the multi-segment end effector.
Figure 5E:
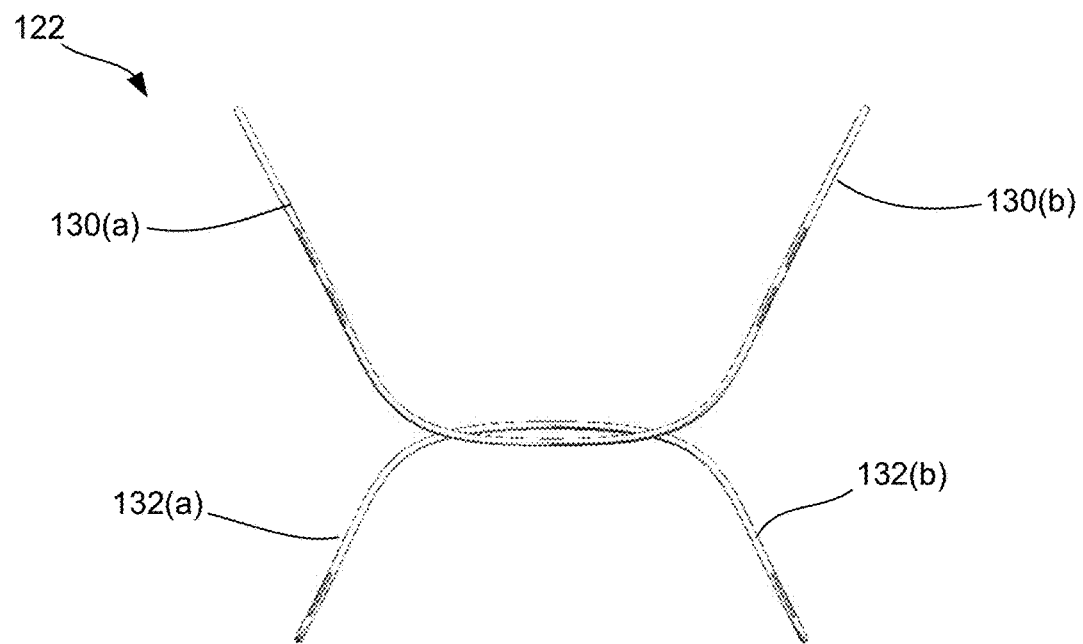
FIG. 5E is an enlarged, front (proximal facing) view of the first (proximal) segment of the multi-segment end effector.
Figure 5F:
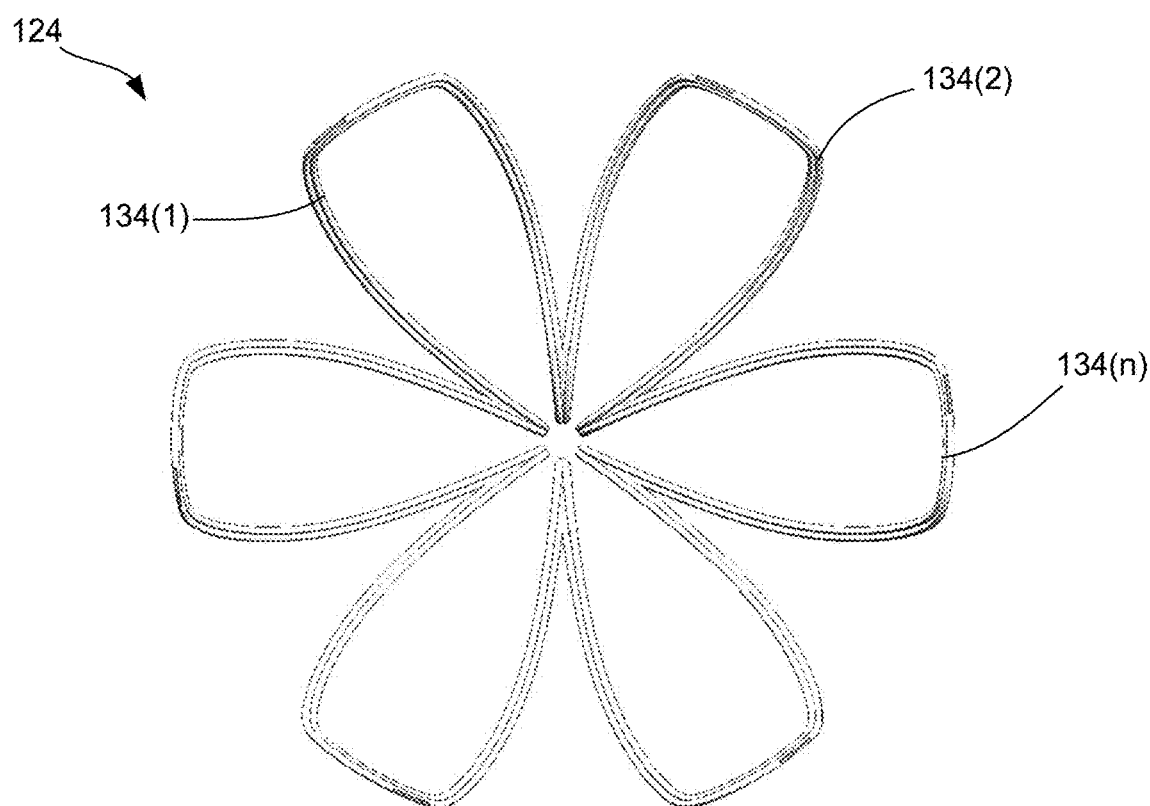
FIG. 5F is an enlarged, front (proximal facing) view of the second (distal) segment of the multi-segment end effector.

FIGS. 5A, 5B, 5C, 5D, 5E, and 5F are enlarged views of the multi-segment end effector 114, illustrating various views of the first and second segments 122, 124 in greater detail. FIG. 5A is an enlarged, perspective view of the multi-segment end effector 114. FIG. 5B is an exploded, perspective view of the multi-segment end effector 114. FIGS. 5C and 5D are enlarged, top and side views, respectively, of the multi-segment end effector 114. FIG. 5E is an enlarged, front (proximal facing) view of the first segment 122 of the multi-segment end effector 114. FIG. 5F is an enlarged, front (proximal facing) view of the second segment 124 of the multi-segment end effector 114.

As illustrated, the first segment 122 includes at least a first set of flexible support elements, generally in the form of wires, arranged in a first configuration, and the second segment 124 includes a second set of flexible support elements, also in the form of wires, arranged in a second configuration. The first and second sets of flexible support elements include composite wires having conductive and elastic properties. For example, in some embodiments, the composite wires include a shape memory material, such as nitinol. The flexible support elements may further include a highly lubricious coating, which may allow for desirable electrical insulation properties as well as desirable low friction surface finish. Each of the first and second segments 122, 124 is transformable between a retracted configuration and an expanded deployed configuration such that the first and second sets of flexible support elements are configured to position one or more electrodes provided on the respective segments (see electrodes 136 in FIGS. 5E and 5F) into contact with one or more target sites when in the deployed configuration.

As shown, when in the expanded deployed configuration, the first set of support elements of the first segment 122 includes at least a first pair of struts 130a, 130b, each comprising a loop (or leaflet) shape and extending in an upward direction and a second pair of struts 132a, 132b, each comprising a loop (or leaflet) shape and extending in a downward direction, generally in an opposite direction relative to at least the first pair of struts 130a, 130b. It should be noted that the terms upward and downward are used to describe the orientation of the first and second segments 122, 124 relative to one another. More specifically, the first pair of struts 130a, 130b generally extend in an outward inclination in a first direction relative to a longitudinal axis of the multi-segment end effector 114 and are spaced apart from one another. Similarly, the second pair of struts 132a, 132b extend in an outward inclination in a second direction substantially opposite the first direction relative to the longitudinal axis of the multi-segment end effector and spaced apart from one another.

The second set of support elements of the second segment 124, when in the expanded deployed configuration, includes a second set of struts 134(1), 134(2), 134(n) (approximately six struts), each comprising a loop shape extending outward to form an open-ended circumferential shape. As shown, the open-ended circumferential shape generally resembles a blooming flower, wherein each looped strut 134 may generally resemble a flower petal. It should be noted that the second set of struts 134 may include any number of individual struts and is not limited to six, as illustrated. For example, in some embodiments, the second segment 124 may include two, three, four, five, six, seven, eight, nine, ten, or more struts 134.

The first and second segments 122, 124, specifically struts 130, 132, and 134 include one or more energy delivery elements, such as a plurality of electrodes 136. It should be noted that any individual strut may include any number of electrodes 136 and is not limited to one electrode, as shown. In the expanded state, the struts 130, 132, and 134 can position any number of electrodes 136 against tissue at a target site within the nasal region (e.g., proximate to the palatine bone inferior to the SPF). The electrodes 136 can apply bipolar or multi-polar radiofrequency (RF) energy to the target site to therapeutically modulate postganglionic parasympathetic nerves that innervate the nasal mucosa proximate to the target site. In various embodiments, the electrodes 136 can be configured to apply pulsed RF energy with a desired duty cycle (e.g., 1 second on/0.5 seconds off) to regulate the temperature increase in the target tissue.

Figure 6:
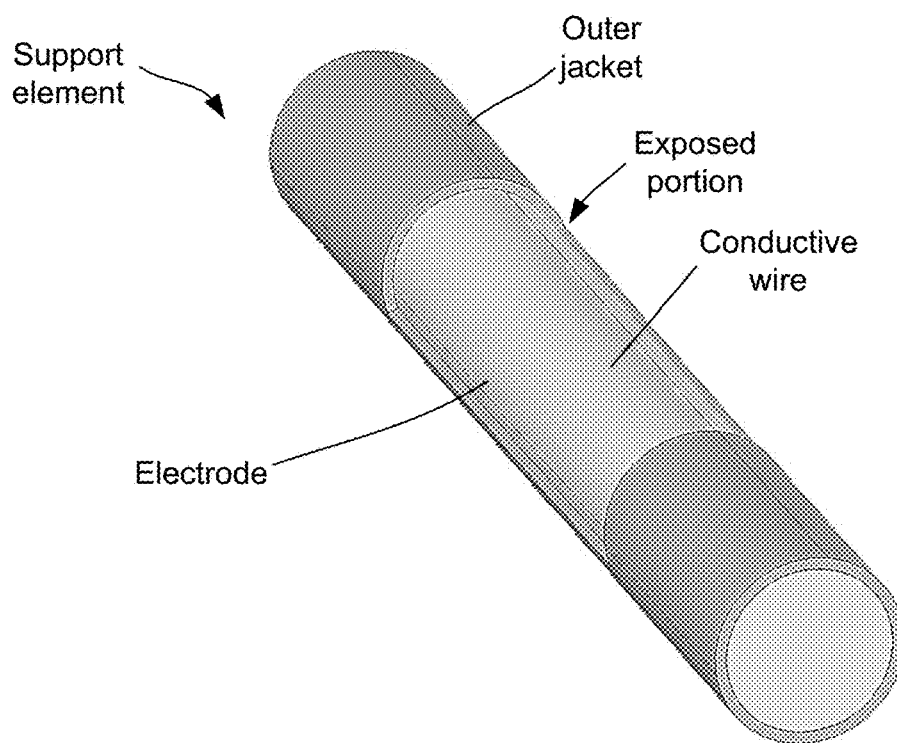
FIG. 6 is a perspective view, partly in section, of a portion of a support element illustrating an exposed conductive wire serving as an energy delivery element or electrode element.

The first and second segments 122, 124 and the associated struts 130, 132, and 134 can have sufficient rigidity to support the electrodes 136 and position or press the electrodes 136 against tissue at the target site. In addition, each of the expanded first and second segments 122, 124 can press against surrounding anatomical structures proximate to the target site (e.g., the turbinates, the palatine bone, etc.) and the individual struts 130, 132, 134 can at least partially conform to the shape of the adjacent anatomical structures to anchor the end effector 114 In addition, the expansion and conformability of the struts 130, 132, 134 can facilitate placing the electrodes 136 in contact with the surrounding tissue at the target site. The electrodes 136 can be made from platinum, iridium, gold, silver, stainless steel, platinum-iridium, cobalt chromium, iridium oxide, polyethylenedioxythiophene (PEDOT), titanium, titanium nitride, carbon, carbon nanotubes, platinum grey, Drawn Filled Tubing (DFT) with a silver core, and/or other suitable materials for delivery RF energy to target tissue. In some embodiments, such as illustrated in FIG. 6, a strut may include an outer jacket surrounding a conductive wire, wherein portions of the outer jacket are selectively absent along a length of the strut, thereby exposing the underlying conductive wire so as to act as an energy delivering element (i.e., an electrode) and/or sensing element, as described in greater detail herein.

In certain embodiments, each electrode 136 can be operated independently of the other electrodes 136. For example, each electrode can be individually activated and the polarity and amplitude of each electrode can be selected by an operator or a control algorithm (e.g., executed by the controller 107 previously described herein. The selective independent control of the electrodes 136 allows the end effector 114 to deliver RF energy to highly customized regions. For example, a select portion of the electrodes 136 can be activated to target neural fibers in a specific region while the other electrodes 136 remain inactive. In certain embodiments, for example, electrodes 136 may be activated across the portion of the second segment 124 that is adjacent to tissue at the target site, and the electrodes 136 that are not proximate to the target tissue can remain inactive to avoid applying energy to non-target tissue. Such configurations facilitate selective therapeutic modulation of nerves on the lateral nasal wall within one nostril without applying energy to structures in other portions of the nasal cavity.

The electrodes 136 are electrically coupled to an RF generator (e.g., the generator 106 of FIG. 1) via wires (not shown) that extend from the electrodes 136, through the shaft 116, and to the RF generator. When each of the electrodes 136 is independently controlled, each electrode 136 couples to a corresponding wire that extends through the shaft 116. In other embodiments, multiple electrodes 116 can be controlled together and, therefore, multiple electrodes 116 can be electrically coupled to the same wire extending through the shaft 116. As previously described, the RF generator and/or components operably coupled (e.g., a control module) thereto can include custom algorithms to control the activation of the electrodes 136. For example, the RF generator can deliver RF power at about 460-480 kHz (+ or −5 kHz) to the electrodes 136, and do so while activating the electrodes 136 in a predetermined pattern selected based on the position of the end effector 114 relative to the treatment site and/or the identified locations of the target nerves. The RF generator is able to provide bipolar low power (10 watts with maximum setting of 50 watts) RF energy delivery, and further provide multiplexing capabilities (across a maximum of 30 channels).

Once deployed, the first and second segments 122, 124 contact and conform to a shape of the respective locations, including conforming to and complementing shapes of one or more anatomical structures at the respective locations. In turn, the first and second segments 122, 124 become accurately positioned within the nasal cavity to subsequently deliver, via one or more electrodes 136, precise and focused application of RF thermal energy to the one or more target sites to thereby therapeutically modulate associated neural structures. More specifically, the first and second segments 122, 124 have shapes and sizes when in the expanded configuration that are specifically designed to place portions of the first and second segments 122, 124, and thus one or more electrodes associated therewith 136, into contact with target sites within nasal cavity associated with postganglionic parasympathetic fibers that innervate the nasal mucosa.

For example, the first set of flexible support elements of the first segment 122 conforms to and complements a shape of a first anatomical structure at the first location when the first segment 122 is in the deployed configuration and the second set of flexible support elements of the second segment 124 conforms to and complements a shape of a second anatomical structure at the second location when the second segment is in the deployed configuration. The first and second anatomical structures may include, but are not limited to, inferior turbinate, middle turbinate, superior turbinate, inferior meatus, middle meatus, superior meatus, pterygopalatine region, pterygopalatine fossa, sphenopalatine foramen, accessory sphenopalatine foramen(ae), and sphenopalatine micro-foramen(ae).

In some embodiments, the first segment 122 of the multi-segment end effector 114 is configured in a deployed configuration to fit around at least a portion of a middle turbinate at an anterior position relative to the middle turbinate and the second segment 124 of the multi-segment end effector is configured in a deployed configuration to contact a plurality of tissue locations in a cavity at a posterior position relative to the middle turbinate.

For example, the first set of flexible support elements of the first segment (i.e., struts 130 and 132) conforms to and complements a shape of a lateral attachment and posterior-inferior edge of the middle turbinate when the first segment 122 is in the deployed configuration and the second set of flexible support elements (i.e., struts 134) of the second segment 124 contact a plurality of tissue locations in a cavity at a posterior position relative to the lateral attachment and posterior-inferior edge of middle turbinate when the second segment 124 is in the deployed configuration. Accordingly, when in the deployed configuration, the first and second segments 122, 124 are configured to position one or more associated electrodes 136 at one or more target sites relative to either of the middle turbinate and the plurality of tissue locations in the cavity behind the middle turbinate. In turn, electrodes 136 are configured to deliver RF energy at a level sufficient to therapeutically modulate postganglionic parasympathetic nerves innervating nasal mucosa at an innervation pathway within the nasal cavity of the patient.

As illustrated in FIG. 5E, the first segment 122 comprises a bilateral geometry. In particular, the first segment 122 includes two identical sides, including a first side formed of struts 130*a*, 132*a* and a second side formed of struts 130*b*, 132*b*. This bilateral geometry allows at least one of the two sides to conform to and accommodate an anatomical structure within the nasal cavity when the first segment 122 is in an expanded state. For example, when in the expanded state, the plurality of struts 130*a*, 132*a* contact multiple locations along multiple portions of the anatomical structure and electrodes provided by the struts are configured to emit energy at a level sufficient to create multiple micro-lesions in tissue of the anatomical structure that interrupt neural signals to mucus producing and/or mucosal engorgement elements. In particular, struts 130*a*, 132*a* conform to and complement a shape of a lateral attachment and posterior-inferior edge of the middle turbinate when the first segment 122 is in the deployed configuration, thereby allowing for both sides of the anatomical structure to receive energy from the electrodes. By having this independence between first and second side (i.e., right and left side) configurations, the first segment 122 is a true bilateral device. By providing a bilateral geometry, the multi-segment end effector 114 does not require a repeat use configuration to treat the other side of the anatomical structure, as both sides of the structure are accounted at the same time due to the bilateral geometry. The resultant micro-lesion pattern can be repeatable and is predictable in both macro element (depth, volume, shape parameter, surface area) and can be controlled to establish low to high effects of each, as well as micro elements (the thresholding of effects within the range of the macro envelope can be controlled), as well be described in greater detail herein. The systems of the present invention are further able to establish gradients within allowing for control over neural effects without having widespread effect to other cellular bodies, as will be described in greater detail herein.

Figure 7:
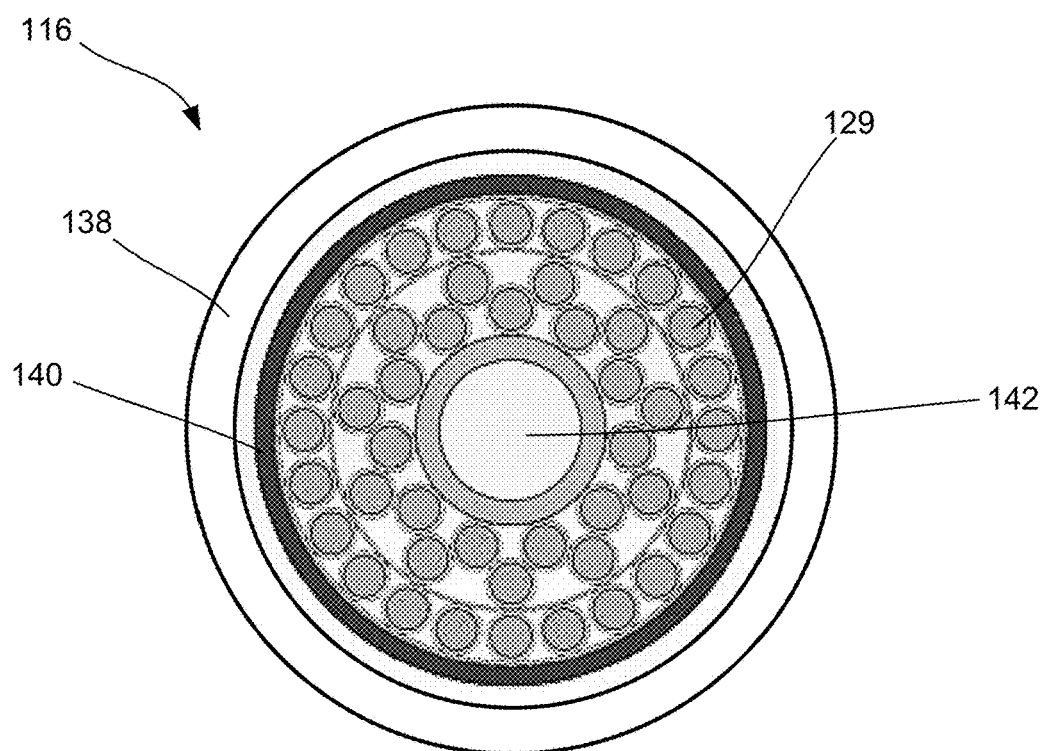
FIG. 7 is a cross-sectional view of a portion of the shaft of the handheld device taken along lines 7-7 of FIG. 4.

FIG. 7 is a cross-sectional view of a portion of the shaft 116 of the handheld device taken along lines 7-7 of FIG. 4. As illustrated, the shaft 116 may be constructed from multiple components so as to have the ability to constrain the end effector 114 in the retracted configuration (i.e., the low-profile delivery state) when the end effector 114 is retracted within the shaft 116, and to further provide an atraumatic, low profile and durable means to deliver the end effector 114 to the target site. The shaft 116 includes coaxial tubes which travel from the handle 118 to a distal end of the shaft 116. The shaft 116 assembly is low profile to ensure trans-nasal delivery of therapy. The shaft 116 includes an outer sheath 138, surrounding a hypotube 140, which is further assembled over electrode wires 129 which surround an inner lumen 142. The outer sheath 138 serves as the interface between the anatomy and the device 102. The outer sheath 138 may generally include a low friction PTFE liner to minimize friction between the outer sheath 138 and the hypotube 140 during deployment and retraction. In particular the outer sheath 138 may generally include an encapsulated braid along a length of the shaft 116 to provide flexibility while retaining kink resistance and further retaining column and/or tensile strength. For example, the outer sheath 138 may include a soft Pebax material, which is atraumatic and enables smooth delivery through the nasal passage. The outer sheath 138 may further include orientation/landmark markings on an exterior surface thereof, generally at the distal end, wherein the markings may provide a visual indication to an operator of the architecture and/or spatial orientation of first and/or second segments 122, 124 of the end effector 114 to assist in positioning and deployment of the end effector 114.

The hypotube 140 is assembled over the electrode wires starting within the handle 118 and travelling to the proximal end of the end effector 114. The hypotube 140 generally acts to protect the wires during delivery and is malleable to enable flexibility without kinking to thereby improve trackability. The hypotube 140 provides stiffness and enables torqueability of the device 102 to ensure accurate placement of the end effector 114. The hypotube 140 also provides a low friction exterior surface which enables low forces when the outer sheath 138 moves relative to the hypotube 140 during deployment and retraction or constraint. The shaft 116 may be pre-shaped in such a manner so as to complement the nasal cavity. For example, the hypotube 140 may be annealed to create a bent shaft 116 with a pre-set curve. The hypotube 140 may include a stainless-steel tubing, for example, which interfaces with a liner in the outer sheath 138 for low friction movement.

The inner lumen 142 may generally provide a channel for fluid extraction during a treatment procedure. For example, the inner lumen 142 extends from the distal end of the shaft 116 through the hypotube 140 and to atmosphere via a fluid line (line 121 of FIG. 4). The inner lumen 142 materials are chosen to resist forces of external components acting thereon during a procedure.

Figure 8:
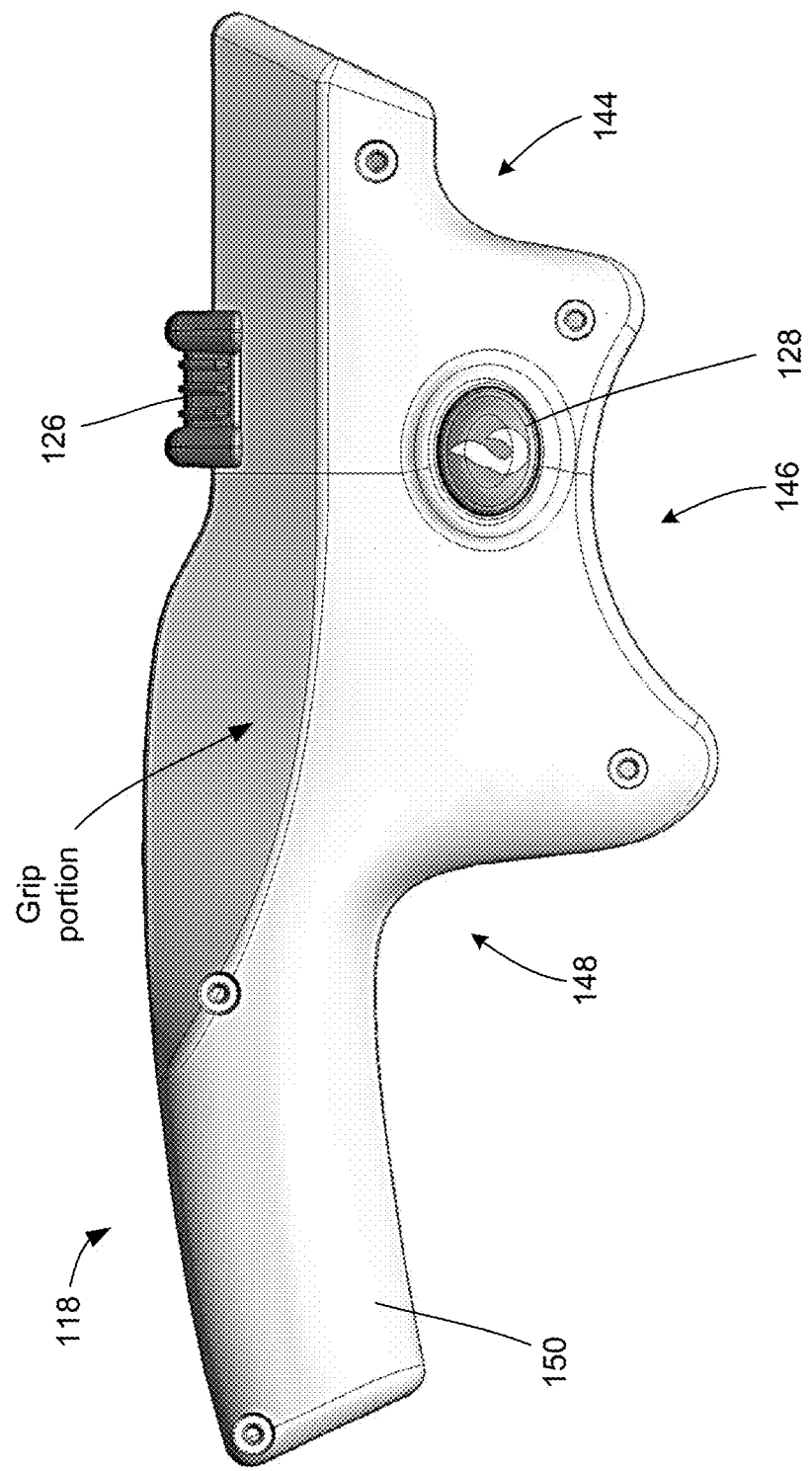
FIG. 8 is a side view of the handle of the handheld device.
Figure 9:
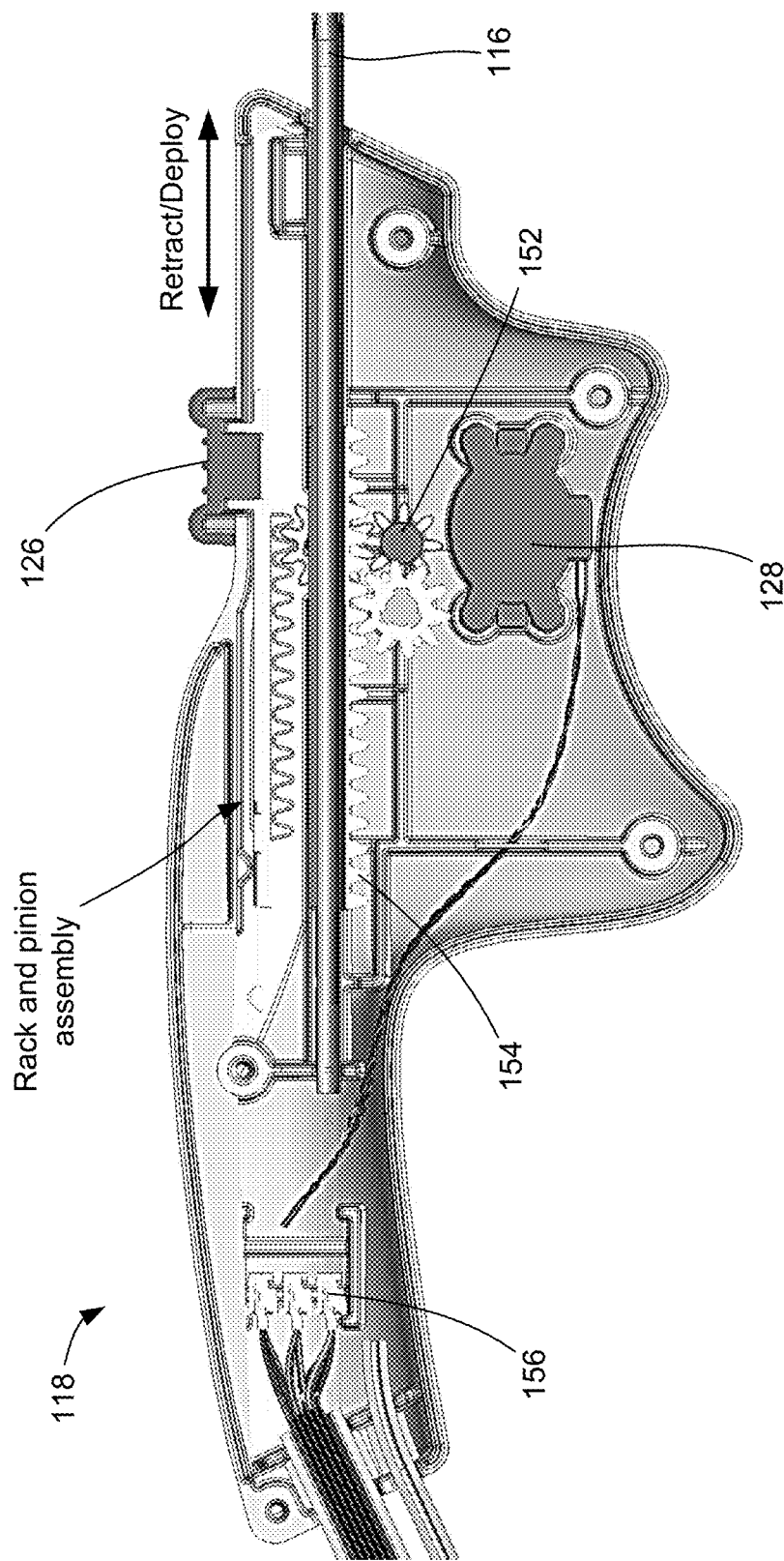
FIG. 9 is a side view of the handle illustrating internal components enclosed within.

FIG. 8 is a side view of the handle 118. FIG. 9 is a side view of the handle 118 illustrating internal components enclosed within. The handle 118 generally includes an ergonomically-designed grip portion which provides ambidextrous use for both left and right handed use and conforms to hand anthropometrics to allow for at least one of an overhand grip style and an underhand grip style during use in a procedure. For example, the handle 118 may include specific contours, including recesses 144, 146, and 148 which are designed to naturally receive one or more of an operator's fingers in either of an overhand grip or underhand grip style and provide a comfortable feel for the operator. For example, in an underhand grip, recess 144 may naturally receive an operator's index finger, recess 146 may naturally receive an operator's middle finger, and recess 148 may naturally receive an operator's ring and little (pinkie or pinky) fingers which wrap around the proximal protrusion 150 and the operator's thumb naturally rests on a top portion of the handle 118 in a location adjacent to the first mechanism 126. In an overhand grip, the operator's index finger may naturally rest on the top portion of the handle 118, adjacent to the first mechanism 126, while recess 144 may naturally receive the operator's middle finger, recess 146 may naturally receive a portion of the operator's middle and/or ring fingers, and recess 148 may naturally receive and rest within the space (sometimes referred to as the purlicue) between the operator's thumb and index finger.

As previously described, the handle includes multiple user-operated mechanisms, including at least a first mechanism 126 for deployment of the end effector 114 from the retracted configuration to the expanded deployed configuration and a second mechanism 128 for controlling of energy output by the end effector, notably energy delivery from one or more electrodes 136. As shown, the user inputs for the first and second mechanisms 126, 128 are positioned a sufficient distance to one another to allow for simultaneous one-handed operation of both user inputs during a procedure. For example, user input for the first mechanism 126 is positioned on a top portion of the handle 118 adjacent the grip portion and user input for the second mechanism 128 is positioned on side portions of the handle 118 adjacent the grip portion. As such, in an underhand grip style, the operator's thumb rests on the top portion of the handle adjacent to the first mechanism 126 and at least their middle finger is positioned adjacent to the second mechanism 128, each of the first and second mechanisms 126, 128 accessible and able to be actuated. In an overhand grip system, the operator's index finger rests on the top portion of the handle adjacent to the first mechanism 126 and at least their thumb is positioned adjacent to the second mechanism 128, each of the first and second mechanisms 126, 128 accessible and able to be actuated. Accordingly, the handle accommodates various styles of grip and provides a degree of comfort for the surgeon, thereby further improving execution of the procedure and overall outcome.

Referring to FIG. 9, the various components provided within the handle 118 are illustrated. As shown, the first mechanism 126 may generally include a rack and pinion assembly providing movement of the end effector 114 between the retracted and deployed configurations in response to input from a user-operated controller. The rack and pinion assembly generally includes a set of gears 152 for receiving input from the user-operated controller and converting the input to linear motion of a rack member 154 operably associated with at least one of the shaft 116 and the end effector 114. The rack and pinion assembly comprises a gearing ratio sufficient to balance a stroke length and retraction and deployment forces, thereby improving control over the deployment of the end effector. As shown, the rack member 154 may be coupled to a portion of the shaft 116, for example, such that movement of the rack member 154 in a direction towards a proximal end of the handle 118 results in corresponding movement of the shaft 116 while the end effector 114 remains stationary, thereby exposing the end effector 114 and allowing the end effector 114 to transition from the constrained, retracted configuration to the expanded, deployed configuration. Similarly, upon movement of the rack member 154 in a direction towards a distal end of the handle 118 results in corresponding movement of the shaft 116 while the end effector 114 remains stationary, thereby enclosing the end effector 114 within the shaft 116. It should be noted that, in other embodiments, the rack member 154 may be directly coupled to a portion of the end effector 114 such that movement of the rack member 154 results in corresponding movement of the end effector 114 while the shaft 116 remains stationary, thereby transitioning the end effector 114 between the retracted and deployed configurations.

The user-operated controller associated with the first mechanism 126 may include a slider mechanism operably associated with the rack and pinion rail assembly. Movement of the slider mechanism in a rearward direction towards a proximal end of the handle results in transitioning of the end effector 114 to the deployed configuration and movement of the slider mechanism in a forward direction towards a distal end of the handle results in transitioning of the end effector to the retracted configuration. In other embodiment, the user-operated controller associated with the first mechanism 126 may include a scroll wheel mechanism operably associated with the rack and pinion rail assembly. Rotation of the wheel in a rearward direction towards a proximal end of the handle results in transitioning of the end effector to the deployed configuration and rotation of the wheel in a forward direction towards a distal end of the handle results in transitioning of the end effector to the retracted configuration.

The user-operated controller associated with the first mechanism 126 may generally provide a high degree of precision and control over the deployment (and retraction) of the first and second segments 122, 124. For example, in some instances, the operator may wish to only deploy the second segment 124 during the procedure, while the first segment 122 remains in the retracted configuration. The user-operated controller allows for an operator to provide a sufficient degree of input (i.e., slide the slider mechanism or scroll the scroll wheel to a specific position) which results in only the second segment 124 transitioning from the retracted configuration to the deployed configuration (while the first segment 122 remains enclosed within the shaft 116 and in the retracted configuration). For example, in some embodiments, the end effector 114 may further include a detent feature, such as a catch or similar element, positioned between the first and second segments 122, 124 and configured to provide a surgeon with feedback, such as haptic or tactile feedback, during deployment of the end effector segments, alerting the surgeon when at least the second segment 124 is fully deployed. In particular, as the surgeon slides the slider mechanism or scrolls the scroll wheel during deployment of the second segment 124, the detect feature (provided between the first and second segments 122, 124) may then reach a portion of the shaft 116 and cause an increase in resistance on the slider mechanism or scroll wheel, thereby indicating to the surgeon that the second segment 124 has been deployed and the first segment 122 remains in the retracted configuration. Accordingly, the surgeon can position and orient the second segment 124 as they desire without concern over the first segment 122 as it remains in the retracted configuration. In turn, one the second segment 124 is positioned at the desired target site, the surgeon may then deploy the first segment 122 to perform the procedure. Yet still, in some instances, only the second segment 124 may be used to perform a procedure (i.e., deliver energy to one or more target sites in contact with the second segment 124) and, as such, the first segment 122 may never be deployed.

The second mechanism 128 may generally include a user-operated controller configured to be actuated between at least an active position and an inactive position to thereby control delivery of energy from the end effector 114, notable delivery of energy from the electrodes 136. The user-operated controller may be multi-modal in that the user-operated controller may be actuated between multiple positions providing different functions/modes. For example, upon a single user input (i.e., single press of button associated within controller), the second mechanism may provide a baseline apposition/sensing check function prior to modulation. Upon pressing and holding the controller button for a pre-defined period of time, the energy output from the end effector may be activated. Further, upon double-tapping the controller button, energy output is deactivated.

Figure 10:
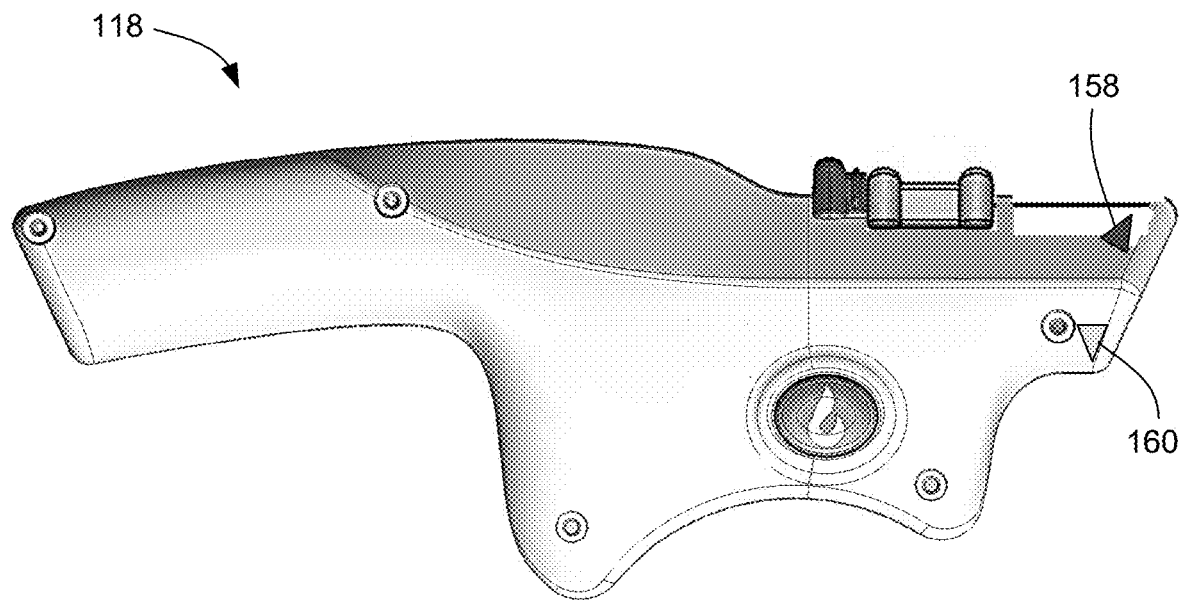
FIG. 10 is a side view of the handle illustrating multiple markings on a portion of the handle for providing a user with a spatial orientation of the end effector while the end effector is in a nasal cavity.
Figure 11:
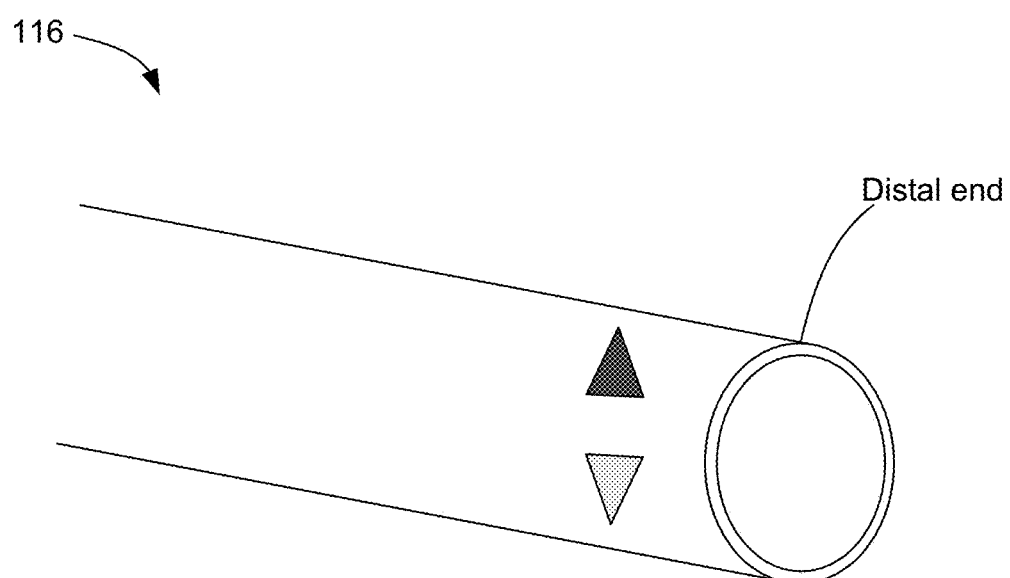
FIG. 11 is a perspective view of the shaft illustrating multiple markings on a distal portion thereof for providing a user with a spatial orientation of the end effector while the end effector is in a nasal cavity.

Furthermore, the handle and/or the shaft may include markings that provide a surgeon with a spatial orientation of the end effector while the end effector is in a nasal cavity. FIG. 10 is a side view of the handle 118 illustrating multiple markings on a distal end of the handle 118 and FIG. 11 is a perspective view of a portion of the shaft 116 illustrating multiple markings on a distal end thereof. In particular, multiple markings may be provided on the handle and/or shaft and provide a visual indication of the spatial orientation of one or more portions of the first segment and second segment of the end effector when in the deployed configurations. The markings may include, for example, text, symbols, color-coding insignia, or the like. Thus, during initial placement of the end effector, when in a retracted configuration and enclosed within the shaft, a surgeon can rely on the markings on the handle and/or shaft as a visual indication of the spatial orientation of the end effector (e.g., linear, axial, and/or depth position) prior to deployment to thereby ensure that, once deployed, the end effector, including both the first and second segments, are positioned in the intended locations within the nasal cavity.

For example, the handle and/or shaft may include markings associated with each of the first pair of struts 130a, 130b and each of the second pair of struts 132a, 132b, so as to provide an operator with a visual indication as to the resulting spatial orientation and architecture of at least the first segment 122 when initially navigating the nasal cavity and delivering the distal end of the shaft 116 to a target site, prior to deployment of the end effector 114. In other words, the markings provide an operator with an indication of the orientation of at least the first segment 122 of the end effector 114 prior to deploying the end effector 114, thereby ensuring accurate positioning at the desired location.

Figure 12:
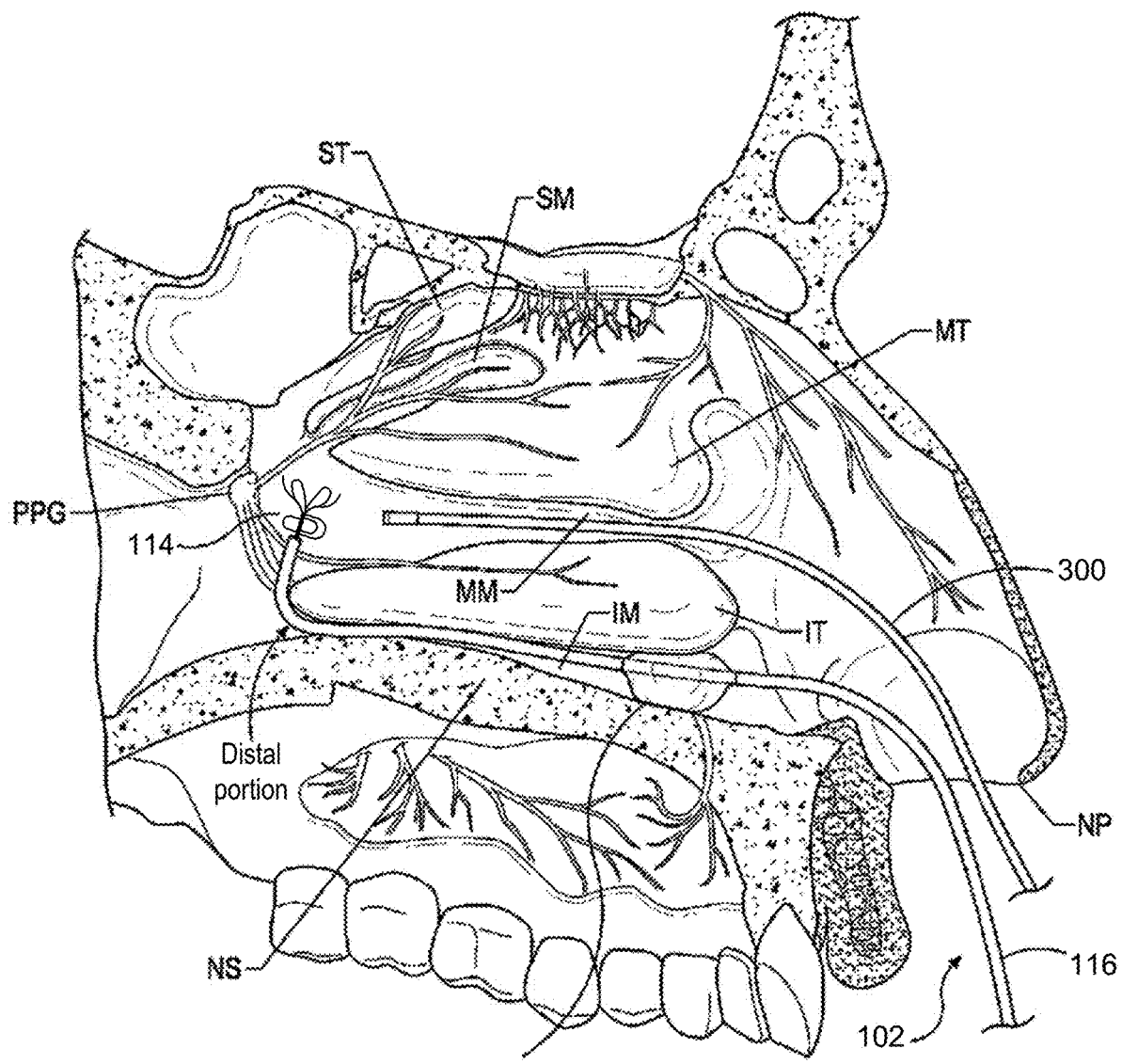
FIG. 12 is a partial cut-away side views illustrating one approach for delivering an end effector a target site within a nasal region in accordance with embodiments of the present disclosure.

FIG. 12 is a partial cut-away side view illustrating one approach for delivering an end effector 114 a target site within a nasal region in accordance with embodiments of the present disclosure. As shown, the distal portion of the shaft 116 extends into the nasal passage NP, through the inferior meatus IM between the inferior turbinate IT and the nasal sill NS, and around the posterior portion of the inferior turbinate IT where the end effector 114 is deployed at a treatment site. The treatment site can be located proximate to the access point or points of postganglionic parasympathetic nerves (e.g., branches of the posterior nasal nerve and/or other parasympathetic neural fibers that innervate the nasal mucosa) into the nasal cavity. In other embodiments, the target site can be elsewhere within the nasal cavity depending on the location of the target nerves.

In various embodiments, the distal portion of the shaft 116 may be guided into position at the target site via a guidewire (not shown) using an over-the-wire (OTW) or a rapid exchange (RX) technique. For example, the end effector 114 can include a channel for engaging the guidewire. Intraluminal delivery of the end effector 114 can include inserting the guide wire into an orifice in communication with the nasal cavity (e.g., the nasal passage or mouth), and moving the shaft 116 and/or the end effector 114 along the guide wire until the end effector 114 reaches a target site (e.g., inferior to the SPF).

Yet still, in further embodiments, the neuromodulation device 102 can be configured for delivery via a guide catheter or introducer sheath (not shown) with or without using a guide wire. The introducer sheath can first be inserted intraluminally to the target site in the nasal region, and the distal portion of the shaft 116 can then be inserted through the introducer sheath. At the target site, the end effector 114 can be deployed through a distal end opening of the introducer sheath or a side port of the introducer sheath. In certain embodiments, the introducer sheath can include a straight portion and a pre-shaped portion with a fixed curve (e.g., a 5 mm curve, a 4 mm curve, a 3 mm curve, etc.) that can be deployed intraluminally to access the target site. In this embodiment, the introducer sheath may have a side port proximal to or along the pre-shaped curved portion through which the end effector 114 can be deployed. In other embodiments, the introducer sheath may be made from a rigid material, such as a metal material coated with an insulative or dielectric material. In this embodiment, the introducer sheath may be substantially straight and used to deliver the end effector 114 to the target site via a substantially straight pathway, such as through the middle meatus MM (FIG. 3A).

Image guidance may be used to aid the surgeon's positioning and manipulation of the distal portion of the shaft 116, as well as the deployment and manipulation of the end effector 114, specifically the first and second segments 122 thereof. For example, an endoscope 100 and/or other visualization device can be positioned to visualize the target site, the positioning of the end effector 114 at the target site, and/or the end effector 114 during therapeutic neuromodulation. The endoscope 100 may be delivered proximate to the target site by extending through the nasal passage NP and through the middle meatus MM between the inferior and middle turbinates IT and MT. From the visualization location within the middle meatus MM, the endoscope 100 can be used to visualize the treatment site, surrounding regions of the nasal anatomy, and the end effector 114.

In some embodiments, the distal portion of the shaft 116 may be delivered via a working channel extending through an endoscope, and therefore the endoscope can provide direct in-line visualization of the target site and the end effector 114. In other embodiments, an endoscope is incorporated with the end effector 114 and/or the distal portion of the shaft 116 to provide in-line visualization of the end effector 114 and/or the surrounding nasal anatomy. In other embodiments, image guidance can be provided with various other guidance modalities, such as image filtering in the infrared (IR) spectrum to visualize the vasculature and/or other anatomical structures, computed tomography (CT), fluoroscopy, ultrasound, optical coherence tomography (OCT), and/or combinations thereof. Yet still, in some embodiments, image guidance components may be integrated with the neuromodulation device 102 to provide image guidance during positioning of the end effector 114.

Once positioned at the target site, the therapeutic modulation may be applied via the one or more electrodes 136 and/or other features of the end effector 114 to precise, localized regions of tissue to induce one or more desired therapeutic neuromodulating effects to disrupt parasympathetic motor sensory function. The end effector 114 can selectively target postganglionic parasympathetic fibers that innervate the nasal mucosa at a target or treatment site proximate to or at their entrance into the nasal region. For example, the end effector 114 can be positioned to apply therapeutic neuromodulation at least proximate to the SPF (FIG. 3A) to therapeutically modulate nerves entering the nasal region via the SPF. The end effector 114 can also be positioned to inferior to the SPF to apply therapeutic neuromodulation energy across accessory foramen and microforamina (e.g., in the palatine bone) through which smaller medial and lateral branches of the posterior superior lateral nasal nerve enter the nasal region. The purposeful application of the energy at the target site may achieve therapeutic neuromodulation along all or at least a portion of posterior nasal neural fibers entering the nasal region. The therapeutic neuromodulating effects are generally a function of, at least in part, power, time, and contact between the energy delivery elements and the adjacent tissue. For example, in certain embodiments therapeutic neuromodulation of autonomic neural fibers are produced by applying RF energy at a power of about 2-20 W (e.g., 5 W, 7 W, 10 W, etc.) for a time period of about 1-20 sections (e.g., 5-10 seconds, 8-10 seconds, 10-12 seconds, etc.).

The therapeutic neuromodulating effects may include partial or complete denervation via thermal ablation and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 90° C. (e.g., 70-75° C.) for non-ablative thermal alteration, or the target temperature may be about 100° C. or higher (e.g., 110° C., 120° C., etc.) for the ablative thermal alteration. Desired non-thermal neuromodulation effects may include altering the electrical signals transmitted in a nerve.

Sufficiently modulating at least a portion of the parasympathetic nerves is expected to slow or potentially block conduction of autonomic neural signals to the nasal mucosa to produce a prolonged or permanent reduction in nasal parasympathetic activity. This is expected to reduce or eliminate activation or hyperactivation of the submucosal glands and venous engorgement and, thereby, reduce or eliminate the symptoms of rhinosinusitis. Further, because the device 102 applies therapeutic neuromodulation to the multitude of branches of the posterior nasal nerves rather than a single large branch of the posterior nasal nerve branch entering the nasal cavity at the SPF, the device 102 provides a more complete disruption of the parasympathetic neural pathway that affects the nasal mucosa and results in rhinosinusitis. Accordingly, the device 102 is expected to have enhanced therapeutic effects for the treatment of rhinosinusitis and reduced re-innervation of the treated mucosa.

In other embodiments, the device 102 can be configured to therapeutically modulate nerves and/or other structures to treat different indications. For example, the device 102 can be used to therapeutically modulate nerves that innervate the para-nasal sinuses to treat chronic sinusitis. In further embodiments, the system 100 and the device 102 disclosed herein can be configured therapeutically modulate the vasculature within the nasal anatomy to treat other indications, such as epistaxis (i.e., excessive bleeding from the nose). For example, the system 100 and the device 102 devices described herein can be used to apply therapeutically effective energy to arteries (e.g., the sphenopalatine artery and its branches) as they enter the nasal cavity (e.g., via the SPF, accessory foramen, etc.) to partially or completely coagulate or ligate the arteries. In other embodiments, the system 100 and the device 102 can be configured to partially or completely coagulate or ligate veins and/or other vessels. For such embodiments in which the end effector 114 ligates or coagulates the vasculature, the system 100 and device 102 would be modified to deliver energy at significantly higher power (e.g., about 100 W) and/or longer times (e.g., 1 minute or longer) than would be required for therapeutic neuromodulation.

FIG. 13 is a flow diagram illustrating one embodiment of a method 400 for treating a condition within a nasal cavity of a patient. The method 400 includes advancing a multi-segment end effector within the nasal cavity of the patient (operation 410) wherein the multi-segment end effector includes a first segment spaced apart from a second segment. The multi-segment end effector is retractable and expandable such that, once delivered to the one more target sites within the nasal cavity, the first and second segments can expand to a specific shape and/or size corresponding to anatomical structures within the nasal cavity and associated with the target sites. The method 400 further includes deploying the first and second segments at respective first and second locations within the nasal cavity (operation 420). In particular, each of the first and second flexible segments includes a specific geometry when in a deployed configuration to complement anatomy of respective locations within the nasal cavity. Accordingly, once deployed, the first and second segments contact and conform to a shape of the respective locations, including conforming to and complementing shapes of one or more anatomical structures at the respective locations. The method 400 further includes delivering energy, via the first and second segments, to tissue at one or more target sites with respect to the first and second locations (operation 430). In particular, the first and second segments become accurately positioned within the nasal cavity to subsequently deliver, via one or more electrodes, precise and focused application of RF thermal energy to the one or more target sites to thereby therapeutically modulate associated neural structures. The first and second segments have shapes and sizes when in the expanded configuration that are specifically designed to place portions of the first and second segments, and thus one or more electrodes associated therewith, into contact with target sites within nasal cavity associated with postganglionic parasympathetic fibers that innervate the nasal mucosa.

Figure 14:
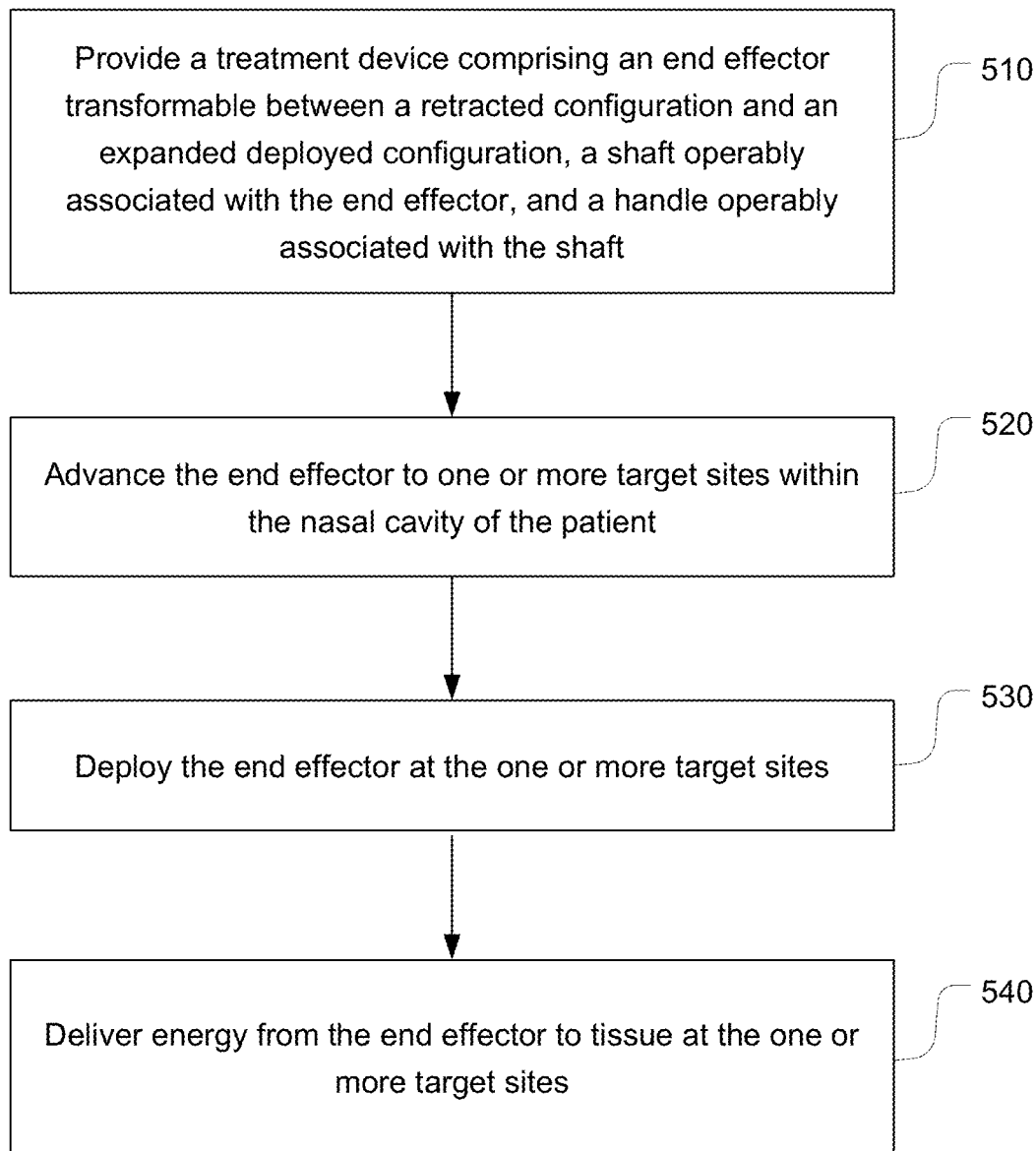
FIG. 14 is a flow diagram illustrating another embodiment of a method for treating a condition within a nasal cavity of a patient.

FIG. 14 is a flow diagram illustrating another embodiment of a method 500 for treating a condition within a nasal cavity of a patient. The method 500 includes providing a treatment device comprising an end effector transformable between a retracted configuration and an expanded deployed configuration, a shaft operably associated with the end effector, and a handle operably associated with the shaft (operation 510). The method 500 further includes advancing the end effector to one or more target sites within the nasal cavity of the patient (operation 520). The shaft may include a pre-defined shape (i.e., bent or angled at a specific orientation) so as to assist the operation for placement of the end effector at the target sites. The handle includes an ergonomically-designed grip portion which provides ambidextrous use for both left and right handed use and conforms to hand anthropometrics to allow for at least one of an overhand grip style and an underhand grip style during use in a procedure.

The handle and/or the shaft may include markings (e.g., text, symbols, color-coding insignia, etc.) that provide a surgeon with a spatial orientation of the end effector while the end effector is in a nasal cavity. In particular, multiple markings may be provided on the handle and/or shaft and provide a visual indication of the spatial orientation of one or more portions of the first segment and second segment of the end effector when in the deployed configurations. Thus, during initial placement of the end effector, when in a retracted configuration and enclosed within the shaft, a surgeon can rely on the markings on the handle and/or shaft as a visual indication of the spatial orientation of the end effector (e.g., linear, axial, and/or depth position) prior to deployment to thereby ensure that, once deployed, the end effector, including both the first and second segments, are positioned in the intended locations within the nasal cavity.

The method 500 further includes deploying the end effector at the one or more target sites (operation 530) and delivering energy from the end effector to tissue at the one or more target sites (operation 540). The handle includes multiple user-operated mechanisms, including at least a first mechanism for deployment of the end effector from the retracted configuration to the expanded deployed configuration and a second mechanism for controlling of energy output by the end effector. The user inputs for the first and second mechanisms are positioned a sufficient distance to one another to allow for simultaneous one-handed operation of both user inputs during a procedure. Accordingly, the handle accommodates various styles of grip and provides a degree of comfort for the surgeon, thereby further improving execution of the procedure and overall outcome.

FIG. 15 is a flow diagram illustrating another embodiment of a method 600 for treating a condition within a nasal cavity of a patient. The method 600 includes providing a treatment device comprising a multi-segment end effector, including a proximal segment that is spaced apart from a distal segment, and a visual marker (operation 610). As previously described herein, the visual marker may be provided by a shaft, for example, operably associated with the multi-segment end effector. The visual marker may be in the form of text, symbols, color-coding insignia, or the like, that generally provides a user (i.e., a surgeon or other medical professional) with a visual indication of a spatial orientation of one or more portions of the proximal segment while the multi-segment end effector is in a nasal cavity.

The method 600 further includes advancing, under image guidance, the proximal segment and the distal segment through a nasal cavity of a patient and past a middle turbinate (operation 620) and deploying the distal segment from a retracted configuration to an expanded configuration (operation 630). The image guidance may be in the form of an endoscope and/or other visualization device that can be positioned to so as to provide visualization to the user of one or more locations within the nasal cavity and to further provide visualization of the multi-segment end effector and other portions of the treatment device (i.e., at least a distal portion of the shaft with a visual marker) during advancement into the nasal cavity to assist the user in placement of the multi-segment end effector.

Upon deploying the distal segment to an expanded configuration, the method 600 further includes aligning, under the image guidance and with reference to the visual marker, the proximal segment with respect to the middle turbinate (operation 640). The visual marker may be provided on the shaft, for example, and provide a visual indication of the spatial orientation of one or more portions of the proximal segment when in the deployed configuration. For example, the deployed proximal segment may include a geometry to complement a shape of the middle turbinate. More specifically, the proximal segment may include a set of flexible support elements that conform to and complement a shape of the middle turbinate when the proximal segment is in the deployed expanded configuration. The visual marker, provided by the shaft, provides a visual indication of the spatial orientation of one or more portions of the proximal segment, including, for example, a spatial orientation of the set of flexible support elements when in a deployed expanded configuration. Accordingly, aligning the proximal segment with respect to the middle turbinate includes the user positioning, under the image guidance, the shaft and associated visual marker relative to the middle turbinate.

Thus, during initial placement of at least the proximal segment when it is in a retracted configuration, a surgeon can rely on the markings on the shaft as a visual indication of the spatial orientation (e.g., linear, axial, and/or depth position) of one or more portions of the proximal segment prior to its deployment, thereby ensuring that, once deployed, the proximal segment is positioned in the intended location within the nasal cavity.

The method 600 further includes deploying the proximal segment around the middle turbinate and advancing the deployed proximal segment toward the middle turbinate to establish contact and secure the proximal segment to the middle turbinate (operation 650). Again, the set of flexible support elements of the proximal segment are able to conform to and complement a shape of the middle turbinate when the proximal segment is in the deployed expanded configuration, thereby ensuring that the deployed proximal segment is secured to the middle turbinate.

It should be noted that the treatment device further includes a handle operably associated with the multi-segment end effector and the shaft. The handle generally includes a controller mechanism for providing independent, controlled deployment of each of the proximal and distal segments from a retracted configuration to an expanded configuration within the nasal cavity. In particular, in some embodiments, the controller mechanism includes a rack and pinion assembly providing movement of the at least one of the proximal and distal segments between the retracted configuration and expanded configuration in response to user input from an associated user-operated controller. The rack and pinion assembly may include, for example, a set of gears for receiving user input from the user-operated controller and converting the user input to linear motion of a rack member operably associated with the multi-segment end effector.

The controller mechanism may further include a detent feature positioned relative to the proximal and distal segments and configured to provide active feedback to a user indicative of deployment of at least one of the proximal and distal segments. The active feedback may be in the form haptic feedback provided by the controller mechanism. For example, the haptic feedback may include an increase or decrease in resistance associated with user input with the controller mechanism for corresponding movement of the at least one of the proximal and distal segments between retracted and expanded configurations, and/or configurations therebetween (i.e., a plurality of configurations between a fully retracted configuration and a fully expanded configuration). For example, upon deploying the distal segment, the controller mechanism, as a result of interaction with the detent, may provide haptic feedback, in the form of a vibration or other motion (e.g., click(s) or change in resistance), to the user via the user-operated controller. The haptic feedback may indicate to the user that the distal segment is fully deployed and any further input with the user-operated controller will result in deployment of the proximal segment. The controller mechanism may further provide specific haptic feedback during deployment of a given segment, such as deployment of the proximal segment. For example, the haptic feedback may be in the form of an increase or decrease in resistance upon the user-operated controller, for example, which corresponds to the degree to which the proximal segment is deployed.

In some embodiments, the controller mechanism may further include a friction-based feature configured to provide stable movement of at least one of the proximal and distal segments between the retracted and expanded configurations and further provide active feedback to a user indicative of deployment of at least one of the proximal and distal segments. The friction-based feature may include, for example, a lock mechanism configured to provide constant friction between one or more portions of the rack and pinion assembly sufficient to maintain a position of at least one of the proximal and distal segments during deployment thereof.

For example, the constant friction may be sufficient to hold either of the proximal or distal segments in a certain position as the segment transitions between retracted and expanded configurations regardless of whether the user maintains contact with the user-operated controller. In other words, a user does not need to maintain contact with the user-operated controller in order to ensure that the proximal or distal segment holds a certain position during deployment thereof. Rather, a user can simply interact with the user-operated controller to transition one of the proximal and distal segments to a desired configuration and the constant friction provided by the locking mechanism is sufficient to maintain the configuration of proximal or distal segment in the event that the user goes hands free (i.e., removes any contact with the user-operated controller). The constant friction is of a level sufficient to prevent undesired movement of the proximal or distal segments (i.e., unintended collapsing or expanding), while still allowing for a user to overcome such friction to move the proximal or distal segment to a desired configuration upon user input with the user-operated controller.

In some embodiments, the user-operated controller includes a slider mechanism operably associated with the rack and pinion rail assembly, wherein movement of the slider mechanism in a first direction results in transitioning of at least one of the proximal and distal segments to an expanded configuration and movement of the slider mechanism in a second opposite direction results in transitioning of at least one of the proximal and distal segments to the retracted configuration. In other embodiments, the user-operated controller includes a scroll wheel mechanism operably associated with the rack and pinion rail assembly, wherein rotation of the wheel in a first direction results in transitioning of at least one of the proximal and distal segments to an expanded configuration and rotation of the wheel in a second opposite direction results in transitioning of at least one of the proximal and distal segments to the retracted configuration. As such, during deployment of the proximal segment, the slider mechanism or scroll wheel may provide increased resistance to a user as the user transitions the proximal segment from a fully retracted configuration to a fully deployed configuration.

Accordingly, during deployment of either of the distal and proximal segments, the controller mechanism provides active feedback to the user, wherein such active feedback can be indicative of which segment is being actively controlled and/or the extent of deployment of either of the distal or proximal segments, thereby improving user control over the deployment of either of the distal and proximal segments.

Upon securing the proximal segment to the middle turbinate, the method 600 further includes delivering energy, via the proximal segment, to the middle turbinate to treat a condition (operation 660). The condition may include, but is not limited to, allergic rhinitis, non-allergic rhinitis, chronic rhinitis, acute rhinitis, chronic sinusitis, acute sinusitis, chronic rhinosinusitis, acute rhinosinusitis, and medical resistant rhinitis, and a combination thereof. In some embodiments, delivering energy from the proximal segment includes delivering radiofrequency (RF) energy, via one or more electrodes provided by the proximal segment, to tissue of the middle turbinate at one or more target sites, wherein the one or more target sites are associated with parasympathetic nerve supply. In some embodiments, RF energy is delivered, via the one or more electrodes provided by the proximal segment, at a level sufficient to therapeutically modulate postganglionic parasympathetic nerves innervating nasal mucosa at an innervation pathway within the nasal cavity of the patient.

Accordingly, the handheld device of the present invention provides a user-friendly, non-invasive means of treating rhinosinusitis conditions, including precise and focused application of RF thermal energy to the intended target sites for therapeutic modulation of the intended neural structures without causing collateral and unintended damage or disruption to other neural structures. Thus, the efficacy of a vidian neurectomy procedure can be achieved with the systems and methods of the present invention without the drawbacks discussed above. Most notably, the handheld device provides a surgeon with a user-friendly, non-invasive, and precise means for treating rhinorrhea and other symptoms of rhinosinusitis by targeting only those specific neural structures associated with such conditions, notably postganglionic parasympathetic nerves innervating nasal mucosa, thereby disrupting the parasympathetic nerve supply and interrupting parasympathetic tone. Accordingly, such treatment is effective at treating rhinosinusitis conditions while greatly reducing the risk of causing lateral damage or disruption to other nerve fibers, thereby reducing the likelihood of unintended complications and side effects.

Neuromodulation Monitoring, Feedback, and Mapping Capabilities

As previously described, the system 100 includes a console 104 to which the device 102 is to be connected. The console 104 is configured to provide various functions for the neuromodulation device 102, which may include, but is not limited to, controlling, monitoring, supplying, and/or otherwise supporting operation of the neuromodulation device 102. The console 104 can further be configured to generate a selected form and/or magnitude of energy for delivery to tissue or nerves at the target site via the end effector 114, and therefore the console 104 may have different configurations depending on the treatment modality of the device 102. For example, when device 102 is configured for electrode-based, heat-element-based, and/or transducer-based treatment, the console 104 includes an energy generator 106 configured to generate RF energy (e.g., monopolar, bipolar, or multi-polar RF energy), pulsed electrical energy, microwave energy, optical energy, ultrasound energy (e.g., intraluminally-delivered ultrasound and/or HIFU), direct heat energy, radiation (e.g., infrared, visible, and/or gamma radiation), and/or another suitable type of energy. When the device 102 is configured for cryotherapeutic treatment, the console 104 can include a refrigerant reservoir (not shown), and can be configured to supply the device 102 with refrigerant. Similarly, when the device 102 is configured for chemical-based treatment (e.g., drug infusion), the console 104 can include a chemical reservoir (not shown) and can be configured to supply the device 102 with one or more chemicals.

In some embodiments, the console 104 may include a controller 107 communicatively coupled to the neuromodulation device 102. However, in the embodiments described herein, the controller 107 may generally be carried by and provided within the handle 118 of the neuromodulation device 102. The controller 107 is configured to initiate, terminate, and/or adjust operation of one or more electrodes provided by the end effector 114 directly and/or via the console 104. For example, the controller 107 can be configured to execute an automated control algorithm and/or to receive control instructions from an operator (e.g., surgeon or other medical professional or clinician). For example, the controller 107 and/or other components of the console 104 (e.g., processors, memory, etc.) can include a computer-readable medium carrying instructions, which when executed by the controller 107, causes the device 102 to perform certain functions (e.g., apply energy in a specific manner, detect impedance, detect temperature, detect nerve locations or anatomical structures, perform nerve mapping, etc.). A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory.

The console 104 may further be configured to provide feedback to an operator before, during, and/or after a treatment procedure via mapping/evaluation/feedback algorithms 110. For example, the mapping/evaluation/feedback algorithms 110 can be configured to provide information associated with the location of nerves at the treatment site, the location of other anatomical structures (e.g., vessels) at the treatment site, the temperature at the treatment site during monitoring and modulation, and/or the effect of the therapeutic neuromodulation on the nerves at the treatment site. In certain embodiments, the mapping/evaluation/feedback algorithm 110 can include features to confirm efficacy of the treatment and/or enhance the desired performance of the system 100. For example, the mapping/evaluation/feedback algorithm 110, in conjunction with the controller 107 and the end effector 114, can be configured to monitor neural activity and/or temperature at the treatment site during therapy and automatically shut off the energy delivery when the neural activity and/or temperature reaches a predetermined threshold (e.g., a threshold reduction in neural activity, a threshold maximum temperature when applying RF energy, or a threshold minimum temperature when applying cryotherapy). In other embodiments, the mapping/evaluation/feedback algorithm 110, in conjunction with the controller 107, can be configured to automatically terminate treatment after a predetermined maximum time, a predetermined maximum impedance or resistance rise of the targeted tissue (i.e., in comparison to a baseline impedance measurement), a predetermined maximum impedance of the targeted tissue), and/or other threshold values for biomarkers associated with autonomic function. This and other information associated with the operation of the system 100 can be communicated to the operator via a display 112 (e.g., a monitor, touchscreen, user interface, etc.) on the console 104 and/or a separate display (not shown) communicatively coupled to the console 104.

In various embodiments, the end effector 114 and/or other portions of the system 100 can be configured to detect various bioelectric-parameters of the tissue at the target site, and this information can be used by the mapping/evaluation/feedback algorithms 110 to determine the anatomy at the target site (e.g., tissue types, tissue locations, vasculature, bone structures, foramen, sinuses, etc.), locate neural structures, differentiate between different types of neural structures, map the anatomical and/or neural structure at the target site, and/or identify neuromodulation patterns of the end effector 114 with respect to the patient's anatomy. For example, the end effector 114 can be used to detect resistance, complex electrical impedance, dielectric properties, temperature, and/or other properties that indicate the presence of neural fibers and/or other anatomical structures in the target region. In certain embodiments, the end effector 114, together with the mapping/evaluation/feedback algorithms 110, can be used to determine resistance (rather than impedance) of the tissue (i.e., the load) to more accurately identify the characteristics of the tissue. The mapping/evaluation/feedback algorithms 110 can determine resistance of the tissue by detecting the actual power and current of the load (e.g., via the electrodes 136).

In some embodiments, the system 100 provides resistance measurements with a high degree of accuracy and a very high degree of precision, such as precision measurements to the hundredths of an Ohm (e.g., 0.01Ω) for the range of 1-50Ω. The high degree of resistance detection accuracy provided by the system 100 allows for the detection sub-microscale structures, including the firing of neural structures, differences between neural structures and other anatomical structures (e.g., blood vessels), and event different types of neural structures. This information can be analyzed by the mapping/evaluation/feedback algorithms and/or the controller 107 and communicated to the operator via a high resolution spatial grid (e.g., on the display 112) and/or other type of display to identify neural structures and other anatomy at the treatment site and/or indicate predicted neuromodulation regions based on the ablation pattern with respect to the mapped anatomy.

As previously described, in certain embodiments, each electrode 136 can be operated independently of the other electrodes 136. For example, each electrode can be individually activated and the polarity and amplitude of each electrode can be selected by an operator or a control algorithm executed by the controller 107. The selective independent control of the electrodes 136 allows the end effector 114 to detect information and deliver RF energy to highly customized regions. For example, a select portion of the electrodes 136 can be activated to target specific neural fibers in a specific region while the other electrodes 136 remain inactive. In certain embodiments, for example, electrodes 136 may be activated across the portion of the second segment 124 that is adjacent to tissue at the target site, and the electrodes 136 that are not proximate to the target tissue can remain inactive to avoid applying energy to non-target tissue. In addition, the electrodes 136 can be individually activated to stimulate or therapeutically modulate certain regions in a specific pattern at different times (e.g., via multiplexing), which facilitates detection of anatomical parameters across a zone of interest and/or regulated therapeutic neuromodulation.

The electrodes 136 can be electrically coupled to the energy generator 106 via wires (not shown) that extend from the electrodes 136, through the shaft 116, and to the energy generator 106. When each of the electrodes 136 is independently controlled, each electrode 136 couples to a corresponding wire that extends through the shaft 116. This allows each electrode 136 to be independently activated for stimulation or neuromodulation to provide precise ablation patterns and/or individually detected via the console 104 to provide information specific to each electrode 136 for neural or anatomical detection and mapping. In other embodiments, multiple electrodes 136 can be controlled together and, therefore, multiple electrodes 136 can be electrically coupled to the same wire extending through the shaft 116. The energy generator 16 and/or components (e.g., a control module) operably coupled thereto can include custom algorithms to control the activation of the electrodes 136. For example, the RF generator can deliver RF power at about 200-100 W to the electrodes 136, and do so while activating the electrodes 136 in a predetermined pattern selected based on the position of the end effector 114 relative to the treatment site and/or the identified locations of the target nerves. In other embodiments, the energy generator 106 delivers power at lower levels (e.g., less than 1 W, 1-5 W, 5-15 W, 15-50 W, 50-150 W, etc.) for stimulation and/or higher power levels. For example, the energy generator 106 can be configured to delivery stimulating energy pulses of 1-3 W via the electrodes 136 to stimulate specific targets in the tissue.

As previously described, the end effector 114 can further include one or more temperature sensors disposed on the flexible first and second segments 122, 124 and/or other portions of the end effector 114 and electrically coupled to the console 104 via wires (not shown) that extend through the shaft 116. In various embodiments, the temperature sensors can be positioned proximate to the electrodes 136 to detect the temperature at the interface between tissue at the target site and the electrodes 136. In other embodiments, the temperature sensors can penetrate the tissue at the target site (e.g., a penetrating thermocouple) to detect the temperature at a depth within the tissue. The temperature measurements can provide the operator or the system with feedback regarding the effect of the therapeutic neuromodulation on the tissue. For example, in certain embodiments the operator may wish to prevent or reduce damage to the tissue at the treatment site (e.g., the nasal mucosa), and therefore the temperature sensors can be used to determine if the tissue temperature reaches a predetermined threshold for irreversible tissue damage. Once the threshold is reached, the application of therapeutic neuromodulation energy can be terminated to allow the tissue to remain intact and avoid significant tissue sloughing during wound healing. In certain embodiments, the energy delivery can automatically terminate based on the mapping/evaluation/feedback algorithm 110 stored on the console 104 operably coupled to the temperature sensors.

In certain embodiments, the system 100 can determine the locations and/or morphology of neural structures and/or other anatomical structures before therapy such that the therapeutic neuromodulation can be applied to precise regions including target neural structures, while avoiding negative effects on non-target structures, such as blood vessels. As described in further detail below, the system 100 can detect various bioelectrical parameters in an interest zone (e.g., within in the nasal cavity) to determine the location and morphology of various neural structures (e.g., different types of neural structures, neuronal directionality, etc.) and/or other tissue (e.g., glandular structures, vessels, bony regions, etc.). In some embodiments, the system 100 is configured to measure bioelectric potential. To do so, one or more of the electrodes 136 is placed in contact with an epithelial surface at a region of interest (e.g., a treatment site). Electrical stimuli (e.g., constant or pulsed currents at one or more frequencies) are applied to the tissue by one or more electrodes 136 at or near the treatment site, and the voltage and/or current differences at various different frequencies between various pairs of electrodes 136 of the end effector 114 may be measured to produce a spectral profile or map of the detected bioelectric potential, which can be used to identify different types of tissues (e.g., vessels, neural structures, and/or other types of tissue) in the region of interest. For example, current (i.e., direct or alternating current) can be applied to a pair of electrodes 136 adjacent to each other and the resultant voltages and/or currents between other pairs of adjacent electrodes 136 are measured. It will be appreciated that the current injection electrodes 136 and measurement electrodes 136 need not be adjacent, and that modifying the spacing between the two current injection electrodes 136 can affect the depth of the recorded signals. For example, closely-spaced current injection electrodes 136 provided recorded signals associated with tissue deeper from the surface of the tissue than further spaced apart current injection electrodes 136 that provide recorded signals associated with tissue at shallower depths. Recordings from electrode pairs with different spacings may be merged to provide additional information on depth and localization of anatomical structures.

Further, complex impedance and/or resistance measurements of the tissue at the region of interest can be detected directly from current-voltage data provided by the bioelectric potential measurements while differing levels of frequency currents are applied to the tissue (e.g., via the end effector 114), and this information can be used to map the neural and anatomical structures by the use of frequency differentiation reconstruction. Applying the stimuli at different frequencies will target different stratified layers or cellular bodies or clusters. At high signal frequencies (e.g., electrical injection or stimulation), for example, cell membranes of the neural structures do not impede current flow, and the current passes directly through the cell membranes. In this case, the resultant measurement (e.g., impedance, resistance, capacitance, and/or induction) is a function of the intracellular and extracellular tissue and liquids. At low signal frequencies, the membranes impede current flow to provide different defining characteristics of the tissues, such as the shapes of the cells or cell spacing. The stimulation frequencies can be in the megahertz range, in the kilohertz range (e.g., 400-500 kHz, 450-480 kHz, etc.), and/or other frequencies attuned to the tissue being stimulated and the characteristics of the device being used. The detected complex impedance or resistances levels from the zone of interest can be displayed to the user (e.g., via the display 112) to visualize certain structures based on the stimulus frequency.

Further, the inherent morphology and composition of the anatomical structures in the nasal region react differently to different frequencies and, therefore, specific frequencies can be selected to identify very specific structures. For example, the morphology or composition of targeted structures for anatomical mapping may depend on whether the cells of tissue or other structure are membranonic, stratified, and/or annular. In various embodiments, the applied stimulation signals can have predetermined frequencies attuned to specific neural structures, such as the level of myelination and/or morphology of the myelination. For example, second axonal parasympathetic structures are poorly myelinated than sympathetic nerves or other structures and, therefore, will have a distinguishable response (e.g., complex impedance, resistance, etc.) with respect to a selected frequency than sympathetic nerves. Accordingly, applying signals with different frequencies to the target site can distinguish the targeted parasympathetic nerves from the non-targeted sensory nerves, and therefore provide highly specific target sites for neural mapping before or after therapy and/or neural evaluation post-therapy. In some embodiments, the neural and/or anatomical mapping includes measuring data at a region of interest with at least two different frequencies to identify certain anatomical structures such that the measurements are taken first based on a response to an injection signal having a first frequency and then again based on an injection signal having a second frequency different from the first. For example, there are two frequencies at which hypertrophied (i.e., disease-state characteristics) sub-mucosal targets have a different electrical conductivity or permittivity compared to "normal" (i.e., healthy) tissue. Complex conductivity may be determined based on one or more measured physiological parameters (e.g., complex impedance, resistance, dielectric measurements, dipole measurements, etc.) and/or observance of one or more confidently known attributes or signatures. Furthermore, the system 100 can also apply neuromodulation energy via the electrodes 136 at one or more predetermined frequencies attuned to a target neural structure to provide highly targeted ablation of the selected neural structure associated with the frequency(ies). This highly targeted neuromodulation also reduces the collateral effects of neuromodulation therapy to non-target sites/structures (e.g., blood vessels) because the targeted signal (having a frequency tuned to a target neural structure) will not have the same modulating effects on the non-target structures.

Accordingly, bioelectric properties, such as complex impedance and resistance, can be used by the system 100 before, during, and/or after neuromodulation therapy to guide one or more treatment parameters. For example, before, during, and/or after treatment, impedance or resistance measurements may be used to confirm and/or detect contact between one or more electrodes 136 and the adjacent tissue. The impedance or resistance measurements can also be used to detect whether the electrodes 136 are placed appropriately with respect to the targeted tissue type by determining whether the recorded spectra have a shape consistent with the expected tissue types and/or whether serially collected spectra were reproducible. In some embodiments, impedance or resistance measurements may be used to identify a boundary for the treatment zone (e.g., specific neural structures that are to be disrupted), anatomical landmarks, anatomical structures to avoid (e.g., vascular structures or neural structures that should not be disrupted), and other aspects of delivering energy to tissue.

The bioelectric information can be used to produce a spectral profile or map of the different anatomical features tissues at the target site, and the anatomical mapping can be visualized in a 3D or 2D image via the display 112 and/or other user interface to guide the selection of a suitable treatment site. This neural and anatomical mapping allows the system 100 to accurately detect and therapeutically modulate the postganglionic parasympathetic neural fibers that innervate the mucosa at the numerous neural entrance points into the nasal cavity. Further, because there are not any clear anatomical markers denoting the location of the SPF, accessory foramen, and microforamina, the neural mapping allows the operator to identify and therapeutically modulate nerves that would otherwise be unidentifiable without intricate dissection of the mucosa. In addition, anatomical mapping also allows the clinician to identify certain structures that the clinician may wish to avoid during therapeutic neural modulation (e.g., certain arteries). The neural and anatomical bioelectric properties detected by the system 100 can also be used during and after treatment to determine the real-time effect of the therapeutic neuromodulation on the treatment site. For example, the mapping/evaluation/feedback algorithms 110 can also compare the detected neural locations and/or activity before and after therapeutic neuromodulation, and compare the change in neural activity to a predetermined threshold to assess whether the application of therapeutic neuromodulation was effective across the treatment site.

In various embodiments, the system 100 can also be configured to map the expected therapeutic modulation patterns of the electrodes 136 at specific temperatures and, in certain embodiments, take into account tissue properties based on the anatomical mapping of the target site. For example, the system 100 can be configured to map the ablation pattern of a specific electrode ablation pattern at the 45° C. isotherm, the 55° C. isotherm, the 65° C. isotherm, and/or other temperature/ranges (e.g., temperatures ranging from 45° C. to 70° C. or higher) depending on the target site and/or structure.

The system 100 may provide, via the display 112, three-dimensional views of such projected ablation patterns of the electrodes 136 of the end effector 114. The ablation pattern mapping may define a region of influence that each electrode 136 has on the surrounding tissue. The region of influence may correspond to the region of tissue that would be exposed to therapeutically modulating energy based on a defined electrode activation pattern (i.e., one, two, three, four, or more electrodes on any given strut of the first and second segments 122, 124). In other words, the ablation pattern mapping can be used to illustrate the ablation pattern of any number of electrodes 136, any geometry of the electrode layout, and/or any ablation activation protocol (e.g., pulsed activation, multi-polar/sequential activation, etc.).

In some embodiments, the ablation pattern may be configured such that each electrode 136 has a region of influence surrounding only the individual electrode 136 (i.e., a "dot" pattern). In other embodiments, the ablation pattern may be such that two or more electrodes 136 may link together to form a sub-grouped regions of influence that define peanut-like or linear shapes between two or more electrodes 136. In further embodiments, the ablation pattern can result in a more expansive or contiguous pattern in which the region of influence extends along multiple electrodes 136 (e.g., along each strut). In still further embodiments, the ablation pattern may result in different regions of influence depending upon the electrode activation pattern, phase angle, target temperature, pulse duration, device structure, and/or other treatment parameters. The three-dimensional views of the ablation patterns can be output to the display 112 and/or other user interfaces to allow the clinician to visualize the changing regions of influence based on different durations of energy application, different electrode activation sequences (e.g., multiplexing), different pulse sequences, different temperature isotherms, and/or other treatment parameters. This information can be used to determine the appropriate ablation algorithm for a patient's specific anatomy. In other embodiments, the three-dimensional visualization of the regions of influence can be used to illustrate the regions from which the electrodes 136 detect data when measuring bio-electrical properties for anatomical mapping. In this embodiment, the three dimensional visualization can be used to determine which electrode activation pattern should be used to determine the desired properties (e.g., impedance, resistance, etc.) in the desired area. In certain embodiments, it may be better to use dot assessments, whereas in other embodiments it may be more appropriate to detect information from linear or larger contiguous regions.

In some embodiments, the mapped ablation pattern is superimposed on the anatomical mapping to identify what structures (e.g., neural structures, vessels, etc.) will be therapeutically modulated or otherwise affected by the therapy. An image may be provided to the surgeon which includes a digital illustration of a predicted or planned neuromodulation zone in relation to previously identified anatomical structures in a zone of interest. For example, the illustration may show numerous neural structures and, based on the predicted neuromodulation zone, identifies which neural structures are expected to be therapeutically modulated. The expected therapeutically modulated neural structures may be shaded to differentiate them from the non-affected neural structures. In other embodiments, the expected therapeutically modulated neural structures can be differentiated from the non-affected neural structures using different colors and/or other indicators. In further embodiments, the predicted neuromodulation zone and surrounding anatomy (based on anatomical mapping) can be shown in a three dimensional view (and/or include different visualization features (e.g., color-coding to identify certain anatomical structures, bioelectric properties of the target tissue, etc.). The combined predicted ablation pattern and anatomical mapping can be output to the display 112 and/or other user interfaces to allow the clinician to select the appropriate ablation algorithm for a patient's specific anatomy.

The imaging provided by the system 100 allows the clinician to visualize the ablation pattern before therapy and adjust the ablation pattern to target specific anatomical structures while avoiding others to prevent collateral effects. For example, the clinician can select a treatment pattern to avoid blood vessels, thereby reducing exposure of the vessel to the therapeutic neuromodulation energy. This reduces the risk of damaging or rupturing vessels and, therefore, prevents immediate or latent bleeding. Further, the selective energy application provided by the neural mapping reduces collateral effects of the therapeutic neuromodulation, such as tissue sloughing off during wound healing (e.g., 1-3 weeks post ablation), thereby reducing the aspiration risk associated with the neuromodulation procedure.

The system 100 can be further configured to apply neuromodulation energy (via the electrodes 136) at specific frequencies attuned to the target neural structure and, therefore, specifically target desired neural structures over non-target structures. For example, the specific neuromodulation frequencies can correspond to the frequencies identified as corresponding to the target structure during neural mapping. As described above, the inherent morphology and composition of the anatomical structures react differently to different frequencies. Thus, frequency-tuned neuromodulation energy tailored to a target structure does not have the same modulating effects on non-target structures. More specifically, applying the neuromodulation energy at the target-specific frequency causes ionic agitation in the target neural structure, leading to differentials in osmotic potentials of the targeted neural structures and dynamic changes in neuronal membronic potentials (resulting from the difference in intracellular and extra-cellular fluidic pressure). This causes degeneration, possibly resulting in vacuolar degeneration and, eventually, necrosis at the target neural structure, but is not expected to functionally affect at least some non-target structures (e.g., blood vessels). Accordingly, the system 100 can use the neural-structure specific frequencies to both (1) identify the locations of target neural structures to plan electrode ablation configurations (e.g., electrode geometry and/or activation pattern) that specifically focus the neuromodulation on the target neural structure; and (2) apply the neuromodulation energy at the characteristic neural frequencies to selectively ablate the neural structures responsive to the characteristic neural frequencies. For example, the end effector 114 of the system 100 may selectively stimulate and/or modulate parasympathetic fibers, sympathetic fibers, sensory fibers, alpha/beta/delta fibers, C-fibers, anoxic terminals of one or more of the foregoing, insulated over non-insulated fibers (regions with fibers), and/or other neural structures. In some embodiments, the system 100 may also selectively target specific cells or cellular regions during anatomical mapping and/or therapeutic modulation, such as smooth muscle cells, sub-mucosal glands, goblet cells, stratified cellular regions within the nasal mucosa. Therefore, the system 100 provides highly selective neuromodulation therapy specific to targeted neural structures, and reduces the collateral effects of neuromodulation therapy to non-target structures (e.g., blood vessels).

The present disclosure provides a method of anatomical mapping and therapeutic neuromodulation. The method includes expanding an end effector (i.e., end effector 114) at a zone of interest ("interest zone"), such as in a portion of the nasal cavity. For example, the end effector 114 can be expanded such that at least some of the electrodes 136 are placed in contact with mucosal tissue at the interest zone. The expanded device can then take bioelectric measurements via the electrodes 136 and/or other sensors to ensure that the desired electrodes are in proper contact with the tissue at the interest zone. In some embodiments, for example, the system 100 detects the impedance and/or resistance across pairs of the electrodes 136 to confirm that the desired electrodes have appropriate surface contact with the tissue and that all of the electrodes are 136 functioning properly.

The method continues by optionally applying an electrical stimulus to the tissue, and detecting bioelectric properties of the tissue to establish baseline norms of the tissue. For example, the method can include measuring resistance, complex impedance, current, voltage, nerve firing rate, neuromagnetic field, muscular activation, and/or other parameters that are indicative of the location and/or function of neural structures and/or other anatomical structures (e.g., glandular structures, blood vessels, etc.). In some embodiments, the electrodes 136 send one or more stimulation signals (e.g., pulsed signals or constant signals) to the interest zone to stimulate neural activity and initiate action potentials. The stimulation signal can have a frequency attuned to a specific target structure (e.g., a specific neural structure, a glandular structure, a vessel) that allows for identification of the location of the specific target structure. The specific frequency of the stimulation signal is a function of the host permeability and, therefore, applying the unique frequency alters the tissue attenuation and the depth into the tissue the RF energy will penetrate. For example, lower frequencies typically penetrate deeper into the tissue than higher frequencies.

Pairs of the non-stimulating electrodes 136 of the end effector 114 can then detect one or more bioelectric properties of the tissue that occur in response to the stimulus, such as impedance or resistance. For example, an array of electrodes (e.g., the electrodes 136) can be selectively paired together in a desired pattern (e.g., multiplexing the electrodes 136) to detect the bioelectric properties at desired depths and/or across desired regions to provide a high level of spatial awareness at the interest zone. In certain embodiments, the electrodes 136 can be paired together in a time-sequenced manner according to an algorithm (e.g., provided by the mapping/evaluation/feedback algorithms 110). In various embodiments, stimuli can be injected into the tissue at two or more different frequencies, and the resultant bioelectric responses (e.g., action potentials) in response to each of the injected frequencies can be detected via various pairs of the electrodes 136. For example, an anatomical or neural mapping algorithm can cause the end effector 114 to deliver pulsed RF energy at specific frequencies between different pairs of the electrodes 136 and the resultant bioelectric response can be recorded in a time sequenced rotation until the desired interest zone is adequately mapped (i.e., "multiplexing"). For example, the end effector 114 can deliver stimulation energy at a first frequency via adjacent pairs of the electrodes 136 for a predetermined time period (e.g., 1-50 milliseconds), and the resultant bioelectric activity (e.g., resistance) can be detected via one or more other pairs of electrodes 136 (e.g., spaced apart from each other to reach varying depths within the tissue). The end effector 114 can then apply stimulation energy at a second frequency different from the first frequency, and the resultant bioelectric activity can be detected via the other electrodes. This can continue when the interest zone has been adequately mapped at the desired frequencies. As described in further detail below, in some embodiments the baseline tissue bioelectric properties (e.g., nerve firing rate) are detected using static detection methods (without the injection of a stimulation signal).

After detecting the baseline bioelectric properties, the information can be used to map anatomical structures and/or functions at the interest zone. For example, the bioelectric properties detected by the electrodes 136 can be amazed via the mapping/evaluation/feedback algorithms 110, and an anatomical map can be output to a user via the display 112. In some embodiments, complex impedance, dielectric, or resistance measurements can be used to map parasympathetic nerves and, optionally, identify neural structures in a diseased state of hyperactivity. The bioelectric properties can also be used to map other non-target structures and the general anatomy, such as blood vessels, bone, and/or glandular structures. The anatomical locations can be provided to a user (e.g., on the display 112) as a two-dimensional map (e.g., illustrating relative intensities, illustrating specific sites of potential target structures) and/or as a three-dimensional image. This information can be used to differentiate structures on a submicron, cellular level and identify very specific target structures (e.g., hyperactive parasympathetic nerves). The method can also predict the ablation patterns of the end effector 114 based on different electrode neuromodulation protocol and, optionally, superimpose the predicted neuromodulation patterns onto the mapped anatomy to indicate to the user which anatomical structures will be affected by a specific neuromodulation protocol. For example, when the predicted neuromodulation pattern is displayed in relation to the mapped anatomy, a clinician can determine whether target structures will be appropriately ablated and whether non-target structures (e.g., blood vessels) will be undesirably exposed to the therapeutic neuromodulation energy. Thus, the method can be used for planning neuromodulation therapy to locate very specific target structures, avoid non-target structures, and select electrode neuromodulation protocols.

Once the target structure is located and a desired electrode neuromodulation protocol has been selected, the method continues by applying therapeutic neuromodulation to the target structure. The neuromodulation energy can be applied to the tissue in a highly targeted manner that forms microlesions to selectively modulate the target structure, while avoiding non-targeted blood vessels and allowing the surrounding tissue structure to remain healthy for effective wound healing. In some embodiments, the neuromodulation energy can be applied in a pulsed manner, allowing the tissue to cool between modulation pulses to ensure appropriate modulation without undesirably affecting non-target tissue. In some embodiments, the neuromodulation algorithm can deliver pulsed RF energy between different pairs of the electrodes 136 in a time sequenced rotation until neuromodulation is predicted to be complete (i.e., "multiplexing"). For example, the end effector 114 can deliver neuromodulation energy (e.g., having a power of 5-10 W (e.g., 7 W, 8 W, 9 W) and a current of about 50-100 mA) via adjacent pairs of the electrodes 136 until at least one of the following conditions is met: (a) load resistance reaches a predefined maximum resistance (e.g., 350Ω); (b) a thermocouple temperature associated with the electrode pair reaches a predefined maximum temperature (e.g., 80° C.); or (c) a predetermined time period has elapsed (e.g., 10 seconds). After the predetermined conditions are met, the end effector 114 can move to the next pair of electrodes in the sequence, and the neuromodulation algorithm can terminate when all of the load resistances of the individual pairs of electrodes is at or above a predetermined threshold (e.g., 100Ω). In various embodiments, the RF energy can be applied at a predetermined frequency (e.g., 450-500 kHz) and is expected to initiate ionic agitation of the specific target structure, while avoiding functional disruption of non-target structures.

During and/or after neuromodulation therapy, the method continues by detecting and, optionally, mapping the post-therapy bioelectric properties of the target site. This can be performed in a similar manner as described above. The post-therapy evaluation can indicate if the target structures (e.g., hyperactive parasympathetic nerves) were adequately modulated or ablated. If the target structures are not adequately modulated (i.e., if neural activity is still detected in the target structure and/or the neural activity has not decreased), the method can continue by again applying therapeutic neuromodulation to the target. If the target structures were adequately ablated, the neuromodulation procedure can be completed.

Detection of Anatomical Structures and Function

Various embodiments of the present technology can include features that measure bio-electric, dielectric, and/or other properties of tissue at target sites to determine the presence, location, and/or activity of neural structures and other anatomical structures and, optionally, map the locations of the detected neural structures and/or other anatomical structures. For example, the present technology can be used to detect glandular structures and, optionally, their mucoserous functions and/or other functions. The present technology can also be configured to detect vascular structures (e.g., arteries) and, optionally, their arterial functions, volumetric pressures, and/or other functions. The mapping features discussed below can be incorporated into any the system 100 and/or any other devices disclosed herein to provide an accurate depiction of nerves at the target site.

Neural and/or anatomical detection can occur (a) before the application of a therapeutic neuromodulation energy to determine the presence or location of neural structures and other anatomical structures (e.g., blood vessels, glands, etc.) at the target site and/or record baseline levels of neural activity; (b) during therapeutic neuromodulation to determine the real-time effect of the energy application on the neural fibers at the treatment site; and/or (c) after therapeutic neuromodulation to confirm the efficacy of the treatment on the targeted structures (e.g., nerves glands, etc.). This allows for the identification of very specific anatomical structures (even to the micro-scale or cellular level) and, therefore, provides for highly targeted neuromodulation. This enhances the efficacy and efficiency of the neuromodulation therapy. In addition, the anatomical mapping reduces the collateral effects of neuromodulation therapy to non-target sites. Accordingly, the targeted neuromodulation inhibits damage or rupture of blood vessels (i.e., inhibits undesired bleeding) and collateral damage to tissue that may be of concern during wound healing (e.g., when damage tissue sloughs off of the wall of the nasal wall).

In certain embodiments, the systems disclosed herein can use bioelectric measurements, such as impedance, resistance, voltage, current density, and/or other parameters (e.g., temperature) to determine the anatomy, in particular the neural, glandular, and vascular anatomy, at the target site. The bioelectric properties can be detected after the transmission of a stimulus (e.g., an electrical stimulus, such as RF energy delivered via the electrodes 136; i.e., "dynamic" detection) and/or without the transmission of a stimulus (i.e., "static" detection).

Dynamic measurements include various embodiments to excite and/or detect primary or secondary effects of neural activation and/or propagation. Such dynamic embodiments involve the heightened states of neural activation and propagation and use this dynamic measurement for nerve location and functional identification relative to the neighboring tissue types. For example, a method of dynamic detection can include: (1) delivering stimulation energy to a treatment site via a treatment device (e.g., the end effector 114) to excite parasympathetic nerves at the treatment site; (2) measuring one or more physiological parameters (e.g., resistance, impedance, etc.) at the treatment site via a measuring/sensing array of the treatment device (e.g., the electrodes 136); (4) based on the measurements, identifying the relative presence and position of parasympathetic nerves at the treatment site; and (5) delivering ablation energy to the identified parasympathetic nerves to block the detected para-sympathetic nerves.

Static measurements include various embodiments associated with specific native properties of the stratified or cellular composition at or near the treatment site. The static embodiments are directed to inherent biologic and electrical properties of tissue types at or near the treatment site, the stratified or cellular compositions at or near the treatment site, and contrasting both foregoing measurements with tissue types adjacent the treatment site (and that are not targeted for neuromodulation). This information can be used to localize specific targets (e.g., parasympathetic fibers) and non-targets (e.g., vessels, sensory nerves, etc.). For example, a method of static detection can include: (1) before ablation, utilizing a measuring/sensing array of a treatment device (e.g., the electrodes 136) to determine one or more baseline physiological parameters; (2) geometrically identifying inherent tissue properties within a region of interest based on the measured physiological parameters (e.g., resistance, impedance, etc.); (3) delivering ablation energy to one or more nerves within the region of via treatment device interest; (4) during the delivery of the ablation energy, determining one or more mid-procedure physiological parameters via the measuring/sensing array; and (5) after the delivery of ablation energy, determining one or more post-procedure physiological parameters via the measurement/sensing array to determine the effectiveness of the delivery of the ablation energy on blocking the nerves that received the ablation energy.

After the initial static and/or dynamic detection of bioelectric properties, the location of anatomical features can be used to determine where the treatment site(s) should be with respect to various anatomical structures for therapeutically effective neuromodulation of the targeted parasympathetic nasal nerves. The bioelectric and other physiological properties described herein can be detected via electrodes (e.g., the electrodes 136 of the end effector 114), and the electrode pairings on a device (e.g., end effector 114) can be selected to obtain the bioelectric data at specific zones or regions and at specific depths of the targeted regions. The specific properties detected at or surrounding target neuromodulation sites and associated methods for obtaining these properties are described below. These specific detection and mapping methods discussed below are described with reference to the system 100, although the methods can be implemented on other suitable systems and devices that provide for anatomical identification, anatomical mapping and/or neuromodulation therapy.

Neural Identification and Mapping

In many neuromodulation procedures, it is beneficial to identify the portions of the nerves that fall within a zone and/or region of influence (referred to as the "interest zone") of the energy delivered by a neuromodulation device 102, as well as the relative three-dimensional position of the neural structures relative to the neuromodulation device 102. Characterizing the portions of the neural structures within the interest zone and/or determining the relative positions of the neural structures within the interest zone enables the clinician to (1) selectively activate target neural structures over non-target structures (e.g., blood vessels), and (2) sub-select specific targeted neural structures (e.g., parasympathetic nerves) over non-target neural structures (e.g., sensory nerves, subgroups of neural structures, neural structures having certain compositions or morphologies). The target structures (e.g., parasympathetic nerves) and non-target structures (e.g., blood vessels, sensory nerves, etc.) can be identified based on the inherent signatures of specific structures, which are defined by the unique morphological compositions of the structures and the bioelectrical properties associated with these morphological compositions. For example, unique, discrete frequencies can be associated with morphological compositions and, therefore, be used to identify certain structures. The target and non-target structures can also be identified based on relative bioelectrical activation of the structures to sub-select specific neuronal structures. Further, target and non-target structures can be identified by the differing detected responses of the structures to a tailored injected stimuli. For example, the systems described herein can detect the magnitude of response of structures and the difference in the responses of anatomical structures with respect to differing stimuli (e.g., stimuli injected at different frequencies).

At least for purposes of this disclosure, a nerve can include the following portions that are defined based on their respective orientations relative to the interest zone: terminating neural structures (e.g., terminating axonal structures), branching neural structures (e.g., branching axonal structures), and travelling neural structures (e.g., travelling axonal structures). For example, terminating neural structures enter the zone but do not exit. As such, terminating neural structures are terminal points for neuronal signaling and activation. Branching neural structures are nerves that enter the interest zone and increase number of nerves exiting the interest zone. Branching neural structures are typically associated with a reduction in relative geometry of nerve bundle. Travelling neural structures are nerves that enter the interest zone and exit the zone with no substantially no change in geometry or numerical value.

The system 100 can be used to detect voltage, current, complex impedance, resistance, permittivity, and/or conductivity, which are tied to the compound action potentials of nerves, to determine and/or map the relative positions and proportionalities of nerves in the interest zone. Neuronal cross-sectional area ("CSA") is expected to be due to the increase in axonic structures. Each axon is a standard size. Larger nerves (in cross-sectional dimension) have a larger number of axons than nerves having smaller cross-sectional dimensions. The compound action responses from the larger nerves, in both static and dynamic assessments, are greater than smaller nerves. This is at least in part because the compound action potential is the cumulative action response from each of the axons. When using static analysis, for example, the system 100 can directly measure and map impedance or resistance of nerves and, based on the determined impedance or resistance, determine the location of nerves and/or relative size of the nerves. In dynamic analysis, the system 100 can be used to apply a stimulus to the interest zone and detect the dynamic response of the neural structures to the stimulus. Using this information, the system 100 can determine and/or map impedance or resistance in the interest zone to provide information related to the neural positions or relative nerve sizes. Neural impedance mapping can be illustrated by showing the varying complex impedance levels at a specific location at differing cross-sectional depths. In other embodiments, neural impedance or resistance can be mapped in a three-dimensional display.

Identifying the portions and/or relative positions of the nerves within the interest zone can inform and/or guide selection of one or more treatment parameters (e.g., electrode ablation patterns, electrode activation plans, etc.) of the system 100 for improving treatment efficiency and efficacy. For example, during neural monitoring and mapping, the system 100 can identify the directionality of the nerves based at least in part on the length of the neural structure extending along the interest zone, relative sizing of the neural structures, and/or the direction of the action potentials. This information can then be used by the system 100 or the clinician to automatically or manually adjust treatment parameters (e.g., selective electrode activation, bipolar and/or multipolar activation, and/or electrode positioning) to target specific nerves or regions of nerves. For example, the system 100 can selectively activate specific electrodes 136, electrode combinations (e.g., asymmetric or symmetric), and/or adjust the bi-polar or multi-polar electrode configuration. In some embodiments, the system 100 can adjust or select the waveform, phase angle, and/or other energy delivery parameters based on the nerve portion/position mapping and/or the nerve proportionality mapping. In some embodiments, structure and/or properties of the electrodes 136 themselves (e.g., material, surface roughening, coatings, cross-sectional area, perimeter, penetrating, penetration depth, surface-mounted, etc.) may be selected based on the nerve portion and proportionality mapping.

In various embodiments, treatment parameters and/or energy delivery parameters can be adjusted to target on-axis or near axis travelling neural structures and/or avoid the activation of traveling neural structures that are at least generally perpendicular to the end effector 114. Greater portions of the on-axis or near axis travelling neural structures are exposed and susceptible to the neuromodulation energy provided by the end effector 114 than a perpendicular travelling neural structure, which may only be exposed to therapeutic energy at a discrete cross-section. Therefore, the end effector 114 is more likely to have a greater effect on the on-axis or near axis travelling neural structures. The identification of the neural structure positions (e.g., via complex impedance or resistance mapping) can also allow targeted energy delivery to travelling neural structures rather than branching neural structures (typically downstream of the travelling neural structures) because the travelling neural structures are closer to the nerve origin and, therefore, more of the nerve is affected by therapeutic neuromodulation, thereby resulting in a more efficient treatment and/or a higher efficacy of treatment. Similarly, the identification of neural structure positions can be used to target travelling and branching neural structures over terminal neural structures. In some embodiments, the treatment parameters can be adjusted based on the detected neural positions to provide a selective regional effect. For example, a clinician can target downstream portions of the neural structures if only wanting to influence partial effects on very specific anatomical structures or positions.

In various embodiments, neural locations and/or relative positions of nerves can be determined by detecting the nerve-firing voltage and/or current over time. An array of the electrodes 136 can be positioned in contact with tissue at the interest zone, and the electrodes 136 can measure the voltage and/or current associated with nerve-firing. This information can optionally be mapped (e.g., on a display 112) to identify the location of nerves in a hyper state (i.e., excessive parasympathetic tone). Rhinitis is at least in part the result of over-firing nerves because this hyper state drives the hyper-mucosal production and hyper-mucosal secretion. Therefore, detection of nerve firing rate via voltage and current measurements can be used to locate the portions of the interest region that include hyper-parasympathetic neural function (i.e., nerves in the diseased state). This allows the clinician to locate specific nerves (i.e., nerves with excessive parasympathetic tone) before neuromodulation therapy, rather than simply targeting all parasympathetic nerves (including non-diseased state parasympathetic nerves) to ensure that the correct tissue is treated during neuromodulation therapy. Further, nerve firing rate can be detected during or after neuromodulation therapy so that the clinician can monitor changes in nerve firing rate to validate treatment efficacy. For example, recording decreases or elimination of nerve firing rate after neuromodulation therapy can indicate that the therapy was effective in therapeutically treating the hyper/diseased nerves.

In various embodiments, the system 100 can detect neural activity using dynamic activation by injecting a stimulus signal (i.e., a signal that temporarily activates nerves) via one or more of the electrodes 136 to induce an action potential, and other pairs of electrodes 136 can detect bioelectric properties of the neural response. Detecting neural structures using dynamic activation involves detecting the locations of action potentials within the interest zone by measuring the discharge rate in neurons and the associated processes. The ability to numerically measure, profile, map, and/or image fast neuronal depolarization for generating an accurate index of activity is a factor in measuring the rate of discharge in neurons and their processes. The action potential causes a rapid increase in the voltage across nerve fiber and the electrical impulse then spreads along the fiber. As an action potential occurs, the conductance of a neural cell membrane changes, becoming about 40 times larger than it is when the cell is at rest. During the action potential or neuronal depolarization, the membrane resistance diminishes by about 80 times, thereby allowing an applied current to enter the intracellular space as well. Over a population of neurons, this leads to a net decrease in the resistance during coherent neuronal activity, such as chronic para-sympathetic responses, as the intracellular space will provide additional conductive ions. The magnitude of such fast changes has been estimated to have local resistivity changes with recording near DC is 2.8-3.7% for peripheral nerve bundles (e.g., including the nerves in the nasal cavity).

Detecting neural structures using dynamic activation includes detecting the locations of action potentials within the interest zone by measuring the discharge rate in neurons and the associated processes. The basis of each this discharge is the action potential, during which there is a depolarization of the neuronal membrane of up to 110 mV or more, lasting approximately 2 milliseconds, and due to the transfer of micromolar quantities of ions (e.g., sodium and potassium) across the cellular membrane. The complex impedance or resistance change due to the neuronal membrane falls from 1000 to 25 Ωcm. The introduction of a stimulus and subsequent measurement of the neural response can attenuate noise and improve signal to noise ratios to precisely focus on the response region to improve neural detection, measurement, and mapping.

In some embodiments, the difference in measurements of physiological parameters (e.g., complex impedance, resistance, voltage) over time, which can reduce errors, can be used to create a neural profiles, spectrums, or maps. For example, the sensitivity of the system 100 can be improved because this process provides repeated averaging to a stimulus. As a result, the mapping function outputs can be a unit-less ratio between the reference and test collated data at a single frequency and/or multiple frequencies and/or multiple amplitudes. Additional considerations may include multiple frequency evaluation methods that consequently expand the parameter assessments, such as resistivity, admittivity, center frequency, or ratio of extra- to intracellular resistivity.

In some embodiments, the system 100 may also be configured to indirectly measure the electrical activity of neural structures to quantify the metabolic recovery processes that accompany action potential activity and act to restore ionic gradients to normal. These are related to an accumulation of ions in the extracellular space. The indirect measurement of electrical activity can be approximately a thousand times larger (in the order of millimolar), and thus are easier to measure and can enhance the accuracy of the measured electrical properties used to generate the neural maps.

The system 100 can perform dynamic neural detection by detecting nerve-firing voltage and/or current and, optionally, nerve firing rate over time, in response to an external stimulation of the nerves. For example, an array of the electrodes 136 can be positioned in contact with tissue at the interest zone, one or more of the electrodes 136 can be activated to inject a signal into the tissue that stimulates the nerves, and other electrodes 136 of the electrode array can measure the neural voltage and/or current due to nerve firing in response to the stimulus. This information can optionally be mapped (e.g., on a display 112) to identify the location of nerves and, in certain embodiments, identify parasympathetic nerves in a hyper state (e.g., indicative of Rhinitis or other diseased state). The dynamic detection of neural activity (voltage, current, firing rate, etc.) can be performed before neuromodulation therapy to detect target nerve locations to select the target site and treatment parameters to ensure that the correct tissue is treated during neuromodulation therapy. Further, dynamic detection of neural activity can be performed during or after neuromodulation therapy to allow the clinician to monitor changes in neural activity to validate treatment efficacy. For example, recording decreases or elimination of neural activity after neuromodulation therapy can indicate that the therapy was effective in therapeutically treating the hyper/diseased nerves.

In some embodiments, a stimulating signal can be delivered to the vicinity of the targeted nerve via one or more penetrating electrodes (e.g., microneedles that penetrate tissue) associated with the end effector 114 and/or a separate device. The stimulating signal generates an action potential, which causes smooth muscle cells or other cells to contract. The location and strength of this contraction can be detected via the penetrating electrode(s) and, thereby, indicate to the clinician the distance to the nerve and/or the location of the nerve relative to the stimulating needle electrode. In some embodiments, the stimulating electrical signal may have a voltage of typically 1-2 mA or greater and a pulse width of typically 100-200 microseconds or greater. Shorter pulses of stimulation result in better discrimination of the detected contraction, but may require more current. The greater the distance between the electrode and the targeted nerve, the more energy is required to stimulate. The stimulation and detection of contraction strength and/or location enables identification of how close or far the electrodes are from the nerve, and therefore can be used to localize the nerve spatially. In some embodiments, varying pulse widths may be used to measure the distance to the nerve. As the needle becomes closer to the nerve, the pulse duration required to elicit a response becomes less and less.

To localize nerves via muscle contraction detection, the system 100 can vary pulse-width or amplitude to vary the energy (Energy=pulse-width*amplitude) of the stimulus delivered to the tissue via the penetrating electrode(s). By varying the stimulus energy and monitoring muscle contraction via the penetrating electrodes and/or other type of sensor, the system 100 can estimate the distance to the nerve. If a large amount of energy is required to stimulate the nerve/contract the muscle, the stimulating/penetrating electrode is far from the nerve. As the stimulating/penetrating electrode, moves closer to the nerve, the amount of energy required to induce muscle contraction will drop. For example, an array of penetrating electrodes can be positioned in the tissue at the interest zone and one or more of the electrodes can be activated to apply stimulus at different energy levels until they induce muscle contraction. Using an iterative process, localize the nerve (e.g., via the mapping/evaluation/feedback algorithm 110).

In some embodiments, the system 100 can measure the muscular activation from the nerve stimulus (e.g., via the electrodes 136) to determine neural positioning for neural mapping, without the use of penetrating electrodes. In this embodiment, the treatment device targets the smooth muscle cells' varicosities surrounding the submucosal glands and the vascular supply, and then the compound muscle action potential. This can be used to summate voltage response from the individual muscle fiber action potentials. The shortest latency is the time from stimulus artifact to onset of the response. The corresponding amplitude is measured from baseline to negative peak and measured in millivolts (mV). Nerve latencies (mean±SD) in adults typically range about 2-6 milliseconds, and more typically from about 3.4±0.8 to about 4.0±0.5 milliseconds. A comparative assessment may then be made which compares the outputs at each time interval (especially pre- and post-energy delivery) in addition to a group evaluation using the alternative nasal cavity. This is expected to provide an accurate assessment of the absolute value of the performance of the neural functioning because muscular action/activation may be used to infer neural action/activation and muscle action/activation is a secondary effect or by-product whilst the neural function is the absolute performance measure.

In some embodiments, the system 100 can record a neuromagnetic field outside of the nerves to determine the internal current of the nerves without physical disruption of the nerve membrane. Without being bound by theory, the contribution to the magnetic field from the current inside the membrane is two orders of magnitude larger than that from the external current, and that the contribution from current within the membrane is substantially negligible. Electrical stimulation of the nerve in tandem with measurements of the magnetic compound action fields ("CAFs") can yield sequential positions of the current dipoles such that the location of the conduction change can be estimated (e.g., via the least-squares method). Visual representation (e.g., via the display 112) using magnetic contour maps can show normal or non-normal neural characteristics (e.g., normal can be equated with a characteristic quadrupolar pattern propagating along the nerve), and therefore indicate which nerves are in a diseases, hyperactive state and suitable targets for neuromodulation.

During magnetic field detection, an array of the electrodes 136 can be positioned in contact with tissue at the interest zone and, optionally, one or more of the electrodes 136 can be activated to inject an electrical stimulus into the tissue. As the nerves in the interest zone fire (either in response to a stimulus or in the absence of it), the nerve generates a magnetic field (e.g., similar to a current carrying wire), and therefore changing magnetic fields are indicative of the nerve nerve-firing rate. The changing magnetic field caused by neural firing can induce a current detected by nearby sensor wire (e.g., the sensor 314) and/or wires associated with the nearby electrodes 136. By measuring this current, the magnetic field strength can be determined. The magnetic fields can optionally be mapped (e.g., on a display 112) to identify the location of nerves and select target nerves (nerves with excessive parasympathetic tone) before neuromodulation therapy to ensure that the desired nerves are treated during neuromodulation therapy. Further, the magnetic field information can be used during or after neuromodulation therapy so that the clinician can monitor changes in nerve firing rate to validate treatment efficacy.

In other embodiments, the neuromagnetic field is measured with a Hall Probe or other suitable device, which can be integrated into the end effector 114 and/or part of a separate device delivered to the interest zone. Alternatively, rather than measuring the voltage in the second wire, the changing magnetic field can be measured in the original wire (i.e. the nerve) using a Hall probe. A current going through the Hall probe will be deflected in the semi-conductor. This will cause a voltage difference between the top and bottom portions, which can be measured. In some aspects of this embodiments, three orthogonal planes are utilized.

In some embodiments, the system 100 can be used to induce electromotive force ("EMF") in a wire (i.e., a frequency-selective circuit, such as a tunable/LC circuit) that is tunable to resonant frequency of a nerve. In this embodiment, the nerve can be considered to be a current carrying wire, and the firing action potential is a changing voltage. This causes a changing current which, in turn, causes a changing magnetic flux (i.e., the magnetic field that is perpendicular to the wire). Under Faraday's Law of Induction/Faraday's Principle, the changing magnetic flux induces EMF (including a changing voltage) in a nearby sensor wire (e.g., integrated into the end effector 114, the sensor 314, and/or other structure), and the changing voltage can be measured via the system 100.

In further embodiments, the sensor wire (e.g., the sensor 314) is an inductor and, therefore, provides an increase of the magnetic linkage between the nerve (i.e., first wire) and the sensor wire (i.e., second wire), with more turns for increasing effect. (e.g., V2,rms=V1,rms (N2/N1)). Due to the changing magnetic field, a voltage is induced in the sensor wire, and this voltage can be measured and used to estimate current changes in the nerve. Certain materials can be selected to enhance the efficiency of the EMF detection. For example, the sensor wire can include a soft iron core or other high permeability material for the inductor.

During induced EMF detection, the end effector 114 and/or other device including a sensor wire is positioned in contact with tissue at the interest zone and, optionally, one or more of the electrodes 136 can be activated to inject an electrical stimulus into the tissue. As the nerves in the interest zone fire (either in response to a stimulus or in the absence of it), the nerve generates a magnetic field (e.g., similar to a current carrying wire) that induces a current in the sensor wire (e.g., the sensor 314). This information can be used to determine neural location and/or map the nerves (e.g., on a display 112) to identify the location of nerves and select target nerves (nerves with excessive parasympathetic tone) before neuromodulation therapy to ensure that the desired nerves are treated during neuromodulation therapy. EMF information can also be used during or after neuromodulation therapy so that the clinician can monitor changes in nerve firing rate to validate treatment efficacy.

In some embodiments, the system 100 can detect magnetic fields and/or EMF generated at a selected frequency that corresponds to a particular type of nerve. The frequency and, by extension, the associated nerve type of the detected signal can be selected based on an external resonant circuit. Resonance occurs on the external circuit when it is matched to the frequency of the magnetic field of the particular nerve type and that nerve is firing. In manner, the system 100 can be used to locate a particular sub-group/type of nerves.

In some embodiments, the system 100 can include a variable capacitor frequency-selective circuit to identify the location and/or map specific nerves (e.g., parasympathetic nerve, sensory nerve, nerve fiber type, nerve subgroup, etc.). The variable capacitor frequency-selective circuit can be defined by the sensor 314 and/or other feature of the end effector 114. Nerves have different resonant frequencies based on their function and structure. Accordingly, the system 100 can include a tunable LC circuit with a variable capacitor (C) and/or variable inductor (L) that can be selectively tuned to the resonant frequency of desired nerve types. This allows for the detection of neural activity only associated with the selected nerve type and its associated resonant frequency. Tuning can be achieved by moving the core in and out of the inductor. For example, tunable LC circuits can tune the inductor by: (i) changing the number of coils around the core; (ii) changing the cross-sectional area of the coils around the core; (iii) changing the length of the coil; and/or (iv) changing the permeability of the core material (e.g., changing from air to a core material). Systems including such a tunable LC circuit provide a high degree of dissemination and differentiation not only as to the activation of a nerve signal, but also with respect to the nerve type that is activated and the frequency at which the nerve is firing.

Anatomical Mapping

In various embodiments, the system 100 is further configured to provide minimally-invasive anatomical mapping that uses focused energy current/voltage stimuli from a spatially localized source (e.g., the electrodes 136) to cause a change in the conductivity of the of the tissue at the interest zone and detect resultant biopotential and/or bioelectrical measurements (e.g., via the electrodes 136). The current density in the tissue changes in response to changes of voltage applied by the electrodes 136, which creates a change in the electric current that can be measured with the end effector 114 and/or other portions of the system 100. The results of the bioelectrical and/or biopotential measurements can be used to predict or estimate relative absorption profilometry to predict or estimate the tissue structures in the interest zone. More specifically, each cellular construct has unique conductivity and absorption profiles that can be indicative of a type of tissue or structure, such as bone, soft tissue, vessels, nerves, types of nerves, and/or certain neural structures. For example, different frequencies decay differently through different types of tissue. Accordingly, by detecting the absorption current in a region, the system 100 can determine the underlying structure and, in some instances, to a sub-microscale, cellular level that allows for highly specialized target localization and mapping. This highly specific target identification and mapping enhances the efficacy and efficiency of neuromodulation therapy, while also enhancing the safety profile of the system 100 to reduce collateral effects on non-target structures.

To detect electrical and dielectric tissue properties (e.g., resistance, complex impedance, conductivity, and/or, permittivity as a function of frequency), the electrodes 136 and/or another electrode array is placed on tissue at an interest region, and an internal or external source (e.g., the generator 106) applies stimuli (current/voltage) to the tissue. The electrical properties of the tissue between the source and the receiver electrodes 136 are measured, as well as the current and/or voltage at the individual receiver electrodes 136. These individual measurements can then be converted into an electrical map/image/profile of the tissue and visualized for the user on the display 112 to identify anatomical features of interest and, in certain embodiments, the location of firing nerves. For example, the anatomical mapping can be provided as a color-coded or gray-scale three-dimensional or two-dimensional map showing differing intensities of certain bioelectric properties (e.g., resistance, impedance, etc.), or the information can be processed to map the actual anatomical structures for the clinician. This information can also be used during neuromodulation therapy to monitor treatment progression with respect to the anatomy, and after neuromodulation therapy to validate successful treatment. In addition, the anatomical mapping provided by the bioelectrical and/or biopotential measurements can be used to track the changes to non-target tissue (e.g., vessels) due to neuromodulation therapy to avoid negative collateral effects. For example, a clinician can identify when the therapy begins to ligate a vessel and/or damage tissue, and modify the therapy to avoid bleeding, detrimental tissue ablation, and/or other negative collateral effects.

Furthermore, the threshold frequency of electric current used to identify specific targets can subsequently be used when applying therapeutic neuromodulation energy. For example, the neuromodulation energy can be applied at the specific threshold frequencies of electric current that are target neuronal-specific and differentiated from other non-targets (e.g., blood vessels, non-target nerves, etc.). Applying ablation energy at the target-specific frequency results in an electric field that creates ionic agitation in the target neural structure, which leads to differentials in osmotic potentials of the targeted neural structures. These osmotic potential differentials cause dynamic changes in neuronal membronic potentials (resulting from the difference in intra-cellular and extra-cellular fluidic pressure) that lead to vacuolar degeneration of the targeted neural structures and, eventually, necrosis. Using the highly targeted threshold neuromodulation energy to initiate the degeneration allows the system 100 to delivery therapeutic neuromodulation to the specific target, while surrounding blood vessels and other non-target structures are functionally maintained.

In some embodiments, the system 100 can further be configured to detect bioelectrical properties of tissue by non-invasively recording resistance changes during neuronal depolarization to map neural activity with electrical impedance, resistance, bio-impedance, conductivity, permittivity, and/or other bioelectrical measurements. Without being bound by theory, when a nerve depolarizes, the cell membrane resistance decreases (e.g., by approximately 80×) so that current will pass through open ion channels and into the intracellular space. Otherwise the current remains in the extracellular space. For non-invasive resistance measurements, tissue can be stimulated by applying a current of less than 100 Hz, such as applying a constant current square wave at 1 Hz with an amplitude less than 25% (e.g., 10%) of the threshold for stimulating neuronal activity, and thereby preventing or reducing the likelihood that the current does not cross into the intracellular space or stimulating at 2 Hz. In either case, the resistance and/or complex impedance is recorded by recording the voltage changes. A complex impedance or resistance map or profile of the area can then be generated.

For impedance/conductivity/permittivity detection, the electrodes 136 and/or another electrode array are placed on tissue at an interest region, and an internal or external source (e.g., the generator 106) applies stimuli to the tissue, and the current and/or voltage at the individual receiver electrodes 136 is measured. The stimuli can be applied at different frequencies to isolate different types of nerves. These individual measurements can then be converted into an electrical map/image/profile of the tissue and visualized for the user on the display 112 to identify anatomical features of interest. The neural mapping can also be used during neuromodulation therapy to select specific nerves for therapy, monitor treatment progression with respect to the nerves and other anatomy, and validate successful treatment.

In some embodiments of the neural and/or anatomical detection methods described above, the procedure can include comparing the mid-procedure physiological parameter(s) to the baseline physiological parameter(s) and/or other, previously-acquired mid-procedure physiological parameter(s) (within the same energy delivery phase). Such a comparison can be used to analyze state changes in the treated tissue. The mid-procedure physiological parameter(s) may also be compared to one or more predetermined thresholds, for example, to indicate when to stop delivering treatment energy. In some embodiments of the present technology, the measured baseline, mid-, and post-procedure parameters include a complex impedance. In some embodiments of the present technology, the post-procedure physiological parameters are measured after a pre-determined time period to allow the dissipation of the electric field effects (ionic agitation and/or thermal thresholds), thus facilitating accurate assessment of the treatment.

In some embodiments, the anatomical mapping methods described above can be used to differentiate the depth of soft tissues within the nasal mucosa. The depth of mucosa on the turbinates is great whilst the depth off the turbinate is shallow and, therefore, identifying the tissue depth in the present technology also identifies positions within the nasal mucosa and where precisely to target. Further, by providing the micro-scale spatial impedance mapping of epithelial tissues as described above, the inherent unique signatures of stratified layers or cellular bodies can be used as identifying the region of interest. For example, different regions have larger or small populations of specific structures, such as submucosal glands, so target regions can be identified via the identification of these structures.

In some embodiments, the system 100 includes additional features that can be used to detect anatomical structures and map anatomical features. For example, the system 100 can include an ultrasound probe for identification of neural structures and/or other anatomical structures. Higher frequency ultrasound provides higher resolution, but less depth of penetration. Accordingly, the frequency can be varied to achieve the appropriate depth and resolution for neural/anatomical localization. Functional identification may rely on the spatial pulse length ("SPL") (wavelength multiplied by number of cycles in a pulse). Axial resolution (SPL/2) may also be determined to locate nerves.

In some embodiments, the system 100 can further be configured to emit stimuli with selective parameters that suppress rather than fully stimulate neural activity. for example, in embodiments where the strength-duration relationship for extracellular neural stimulation is selected and controlled, a state exists where the extracellular current can hyperpolarize cells, resulting in suppression rather than stimulation spiking behavior (i.e., a full action potential is not achieved). Both models of ion channels, HH and RGC, suggest that it is possible to hyperpolarize cells with appropriately designed burst extracellular stimuli, rather than extending the stimuli. This phenomenon could be used to suppress rather than stimulate neural activity during any of the embodiments of neural detection and/or modulation described herein.

In various embodiments, the system 100 could apply the anatomical mapping techniques disclosed herein to locate or detect the targeted vasculature and surrounding anatomy before, during, and/or after treatment.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A device for treating a condition within a nasal cavity of a patient, the device comprising:
   a shaft comprising a multi-segment end effector for delivering energy to one or more target sites within the nasal cavity of the patient, the multi-segment end effector comprising:
      a first segment comprising a plurality of first support structures that each comprise one or more electrodes, the plurality of first support structures configured in a deployed configuration to extend in a first direction perpendicular to the shaft and form a concave shape, and a plurality of second support structures that each comprise one or more electrodes, the plurality of second support structures configured in a deployed configuration to extend in a second, opposing direction relative to the shaft and form a concave shape; and
      a second segment configured in a deployed configuration to comprise a plurality of electrodes.

2. The device of claim 1, wherein the plurality of first support structures comprises at least a first pair of support elements that cooperatively form the concave shape relative to the shaft in the first direction when in the deployed configuration and the plurality of second support structures comprises at least a second pair of support elements the cooperatively form the concave shape relative to the shaft in the second direction.

3. The device of claim 1, wherein the second segment comprises a plurality of third support structures that each comprise one or more of the plurality of electrodes, the plurality of third support structures configured in the deployed configuration to extend in a third direction relative to the shaft and cooperatively form an open-ended circumferential shape.

4. The device of claim 1, wherein the plurality of first and second support structures and the second segment comprise deformable composite wires, said composite wires comprising shape memory material.

5. The device of claim 1, wherein the electrodes are configured to deliver radiofrequency (RF) energy.

6. A method for treating a condition within a nasal cavity of a patient, the method comprising:

advancing a device comprising a shaft comprising a multi-segment end effector for delivering energy to one or more target sites within the nasal cavity of the patient, the multi-segment end effector comprising:
- a first segment comprising a plurality of first support structures that each comprise one or more electrodes, the plurality of first support structures configured in a deployed configuration to extend in a first direction perpendicular to the shaft and form a concave shape, and a plurality of second support structures that each comprise one or more electrodes, the plurality of second support structures configured in a deployed configuration to extend in a second, opposing direction relative to the shaft and form a concave shape; and
- a second segment configured in a deployed configuration to comprise a plurality of electrodes;

deploying the first segment at a location relative to a lateral attachment and posterior-inferior edge of middle turbinate and deploying the second segment within a cavity at a posterior position behind the middle turbinate; and delivering energy, via electrodes of the first and second segments, to tissue at one or more target sites with respect to the lateral attachment and posterior-inferior edge of middle turbinate and the plurality of tissue locations in the cavity posterior to the middle turbinate.

7. The method of claim 6, wherein the plurality of first support structures comprises at least a first pair of support elements that cooperatively form the concave shape relative to the shaft in the first direction when in the deployed configuration and the plurality of second support structures comprises at least a second pair of support elements the cooperatively form the concave shape relative to the shaft in the second direction.

8. The method of claim 6, wherein the second segment comprises a plurality of third support structures that each comprise one or more of the plurality of electrodes, the plurality of third support structures configured in the deployed configuration to extend in a third direction relative to the shaft and cooperatively form an open-ended circumferential shape.

9. The method of claim 6, wherein the plurality of first and second support structures and the second segment comprise deformable composite wires, said composite wires comprising shape memory material.

10. The method of claim 6, wherein the electrodes deliver radiofrequency (RF) energy.

* * * * *